(12) United States Patent
Woehr et al.

(10) Patent No.: US 11,850,377 B2
(45) Date of Patent: Dec. 26, 2023

(54) CATHETER ASSEMBLIES AND RELATED METHODS

(71) Applicant: B. Braun Melsungen AG, Melsungen (DE)

(72) Inventors: Kevin Woehr, Felsberg (DE); Chee Mun Phang, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 110 days.

(21) Appl. No.: 16/716,890

(22) Filed: Dec. 17, 2019

(65) Prior Publication Data
US 2020/0188634 A1 Jun. 18, 2020

Related U.S. Application Data

(60) Provisional application No. 62/882,141, filed on Aug. 2, 2019, provisional application No. 62/866,765, filed (Continued)

(30) Foreign Application Priority Data

Dec. 16, 2019 (CN) .......................... 201922254020.2

(51) Int. Cl.
*A61M 25/00* (2006.01)
*A61M 25/06* (2006.01)
*A61M 39/24* (2006.01)

(52) U.S. Cl.
CPC .... *A61M 25/0097* (2013.01); *A61M 25/0014* (2013.01); *A61M 25/0606* (2013.01); *A61M 25/0625* (2013.01); *A61M 2039/2433* (2013.01)

(58) Field of Classification Search
CPC ...... A61M 25/0606; A61M 2039/2433; A61M 2039/064; A61M 2039/0653;
(Continued)

(56) References Cited

U.S. PATENT DOCUMENTS

| 4,387,879 A | 6/1983 | Tauschinski |
|---|---|---|
| 4,424,833 A | 1/1984 | Spector et al. |

(Continued)

FOREIGN PATENT DOCUMENTS

| CN | 101610809 A | 12/2009 |
|---|---|---|
| CN | 101808692 A | 8/2010 |

(Continued)

OTHER PUBLICATIONS

First Examination Report on related foreign application (IN Application No. 201817000337) from the Indian Patent Office dated May 18, 2021.
(Continued)

*Primary Examiner* — Katherine H Schwiker
*Assistant Examiner* — Robert F Allen
(74) *Attorney, Agent, or Firm* — KOS IP LAW LLP

(57) ABSTRACT

Needle devices having a component that provides the function of fixing a valve in a standard diameter sized catheter hub, the valve and/or the component provide or provides a proximally directed axial force for returning the valve opener from a distal position within the catheter hub to a proximal position within the catheter hub when a male Luer is disconnected from the catheter hub. Various components can be located inside a single hub body catheter hub that can restrict fluid flow, allow actuation to permit fluid flow, prevent needlestick injuries, and combinations thereof.

47 Claims, 22 Drawing Sheets

Related U.S. Application Data on Jun. 26, 2019, provisional application No. 62/780,830, filed on Dec. 17, 2018.

(58) Field of Classification Search
CPC .... A61M 2039/066; A61M 2039/0666; A61M 25/0097; A61M 25/0014; A61M 25/0625; A61M 25/625; A61M 39/0693; A61M 39/24

See application file for complete search history.

(56) References Cited

U.S. PATENT DOCUMENTS

| | | |
|---|---|---|
| 4,436,519 A | 3/1984 | O'Neill |
| 4,512,766 A | 4/1985 | Vailancourt |
| 4,673,393 A | 6/1987 | Suzuki et al. |
| 4,683,916 A | 8/1987 | Raines |
| 4,842,591 A | 6/1989 | Luther |
| 4,874,377 A | 10/1989 | Newgard et al. |
| 4,909,798 A | 3/1990 | Fleischhacker et al. |
| 4,917,668 A | 4/1990 | Haindl |
| 5,053,014 A | 10/1991 | Van Heugten |
| 5,062,836 A | 11/1991 | Wendell |
| 5,064,416 A | 11/1991 | Newgard et al. |
| 5,085,645 A | 2/1992 | Purdy et al. |
| 5,114,408 A | 5/1992 | Fleischhaker et al. |
| 5,134,996 A | 8/1992 | Bell |
| 5,154,703 A | 10/1992 | Bonaldo |
| 5,188,607 A | 2/1993 | Wu |
| 5,234,410 A | 8/1993 | Graham et al. |
| 5,242,393 A | 9/1993 | Brimhall et al. |
| 5,254,098 A | 10/1993 | Ulrich et al. |
| 5,269,763 A | 12/1993 | Boehmer et al. |
| 5,269,768 A | 12/1993 | Cheung |
| 5,300,043 A | 4/1994 | Devlin et al. |
| 5,330,435 A | 7/1994 | Vaillancourt |
| 5,342,315 A | 8/1994 | Rowe et al. |
| 5,342,316 A | 8/1994 | Wallace |
| 5,349,950 A | 9/1994 | Ulrich et al. |
| 5,350,363 A | 9/1994 | Goode et al. |
| 5,409,461 A | 4/1995 | Steinman |
| 5,419,766 A | 5/1995 | Chang et al. |
| 5,419,769 A | 5/1995 | Devlin et al. |
| 5,429,616 A | 7/1995 | Schaffer |
| 5,456,284 A | 10/1995 | Ryan et al. |
| 5,458,640 A | 10/1995 | Gerrone |
| 5,460,613 A | 10/1995 | Ulrich et al. |
| 5,476,451 A | 12/1995 | Ensminger et al. |
| 5,480,385 A | 1/1996 | Thorne et al. |
| 5,490,503 A | 2/1996 | Hollister |
| 5,501,674 A | 3/1996 | Trombley, III et al. |
| 5,514,116 A | 5/1996 | Vaillancourt et al. |
| 5,531,720 A | 7/1996 | Atkins |
| 5,533,708 A | 7/1996 | Atkinson et al. |
| 5,542,927 A | 8/1996 | Thorne et al. |
| 5,542,933 A | 8/1996 | Marks |
| 5,607,407 A | 3/1997 | Tolkoff et al. |
| 5,611,782 A | 3/1997 | Haedt |
| 5,613,663 A | 3/1997 | Schmidt et al. |
| 5,628,732 A | 5/1997 | Antoon, Jr. et al. |
| 5,685,866 A | 11/1997 | Lopez |
| 5,688,253 A | 11/1997 | Paradis |
| 5,704,914 A | 1/1998 | Stocking et al. |
| 5,727,770 A | 3/1998 | Dennis |
| 5,749,857 A | 5/1998 | Cuppy |
| 5,755,709 A | 5/1998 | Cuppy |
| 5,759,179 A | 6/1998 | Balbierz |
| 5,792,104 A | 8/1998 | Speckman et al. |
| 5,797,880 A | 8/1998 | Erskine |
| 5,800,395 A | 9/1998 | Botich et al. |
| 5,810,835 A | 9/1998 | Ryan et al. |
| 5,817,069 A | 10/1998 | Arnett |
| 5,830,228 A | 11/1998 | Knapp et al. |
| 5,833,662 A | 11/1998 | Stevens |
| 5,843,046 A | 12/1998 | Motisi et al. |
| 5,853,394 A | 12/1998 | Tolkoff et al. |
| 5,858,002 A | 1/1999 | Jesch |
| 5,865,806 A | 2/1999 | Howell |
| 5,911,706 A | 6/1999 | Estabrook et al. |
| 5,911,710 A | 6/1999 | Barry et al. |
| 5,935,110 A | 8/1999 | Brimhall |
| 5,954,698 A | 9/1999 | Pike |
| 5,968,068 A | 10/1999 | Dehdashtian et al. |
| 5,976,110 A | 11/1999 | Greengrass et al. |
| 6,007,519 A | 12/1999 | Rosselli |
| 6,013,058 A | 1/2000 | Prosl et al. |
| 6,024,727 A | 2/2000 | Thorne et al. |
| 6,024,729 A | 2/2000 | Dehdashtian et al. |
| 6,056,760 A | 5/2000 | Koike et al. |
| 6,074,371 A | 6/2000 | Fischell |
| 6,113,572 A | 9/2000 | Gailey et al. |
| 6,132,402 A | 10/2000 | Tessmann et al. |
| 6,171,287 B1 | 1/2001 | Lynn et al. |
| 6,213,978 B1 | 4/2001 | Voyten |
| 6,217,554 B1 | 4/2001 | Green |
| 6,217,556 B1 | 4/2001 | Ellingson et al. |
| 6,258,065 B1 | 7/2001 | Dennis et al. |
| 6,299,602 B1 | 10/2001 | Miller et al. |
| 6,352,520 B1 | 3/2002 | Miyazaki |
| 6,371,963 B1 | 4/2002 | Nishtala et al. |
| 6,379,337 B1 | 4/2002 | Mohommad |
| 6,482,186 B1 | 11/2002 | Douglas et al. |
| 6,485,473 B1 | 11/2002 | Lynn |
| 6,506,181 B2 | 1/2003 | Meng et al. |
| 6,533,759 B1 | 3/2003 | Watson et al. |
| 6,544,235 B2 | 4/2003 | Motisi et al. |
| 6,610,045 B2 | 8/2003 | Chavez et al. |
| 6,616,630 B1 | 9/2003 | Woehr et al. |
| 6,620,136 B1 | 9/2003 | Pressley, Sr. et al. |
| 6,699,221 B2 | 3/2004 | Vaillancourt |
| 6,719,726 B2 | 4/2004 | Meng et al. |
| 6,740,063 B2 | 5/2004 | Lynn |
| 6,746,420 B1 | 6/2004 | Prestidge et al. |
| 6,764,468 B1 | 7/2004 | East |
| 6,860,869 B2 | 3/2005 | Dennis |
| 6,921,386 B2 | 7/2005 | Shue et al. |
| 6,921,391 B1 | 7/2005 | Barker et al. |
| 6,981,969 B2 | 1/2006 | Chavez et al. |
| 7,008,404 B2 | 3/2006 | Nakajima |
| 7,048,729 B2 | 5/2006 | Meglin et al. |
| 7,052,507 B2 | 5/2006 | Wakuda et al. |
| 7,120,487 B2 | 10/2006 | Nelson |
| 7,125,396 B2 | 10/2006 | Leinsing et al. |
| 7,156,827 B2 | 1/2007 | McNary et al. |
| 7,163,525 B2 | 1/2007 | Franer |
| 7,214,215 B2 | 5/2007 | Heinzerling et al. |
| 7,270,649 B2 | 9/2007 | Fitzgerald |
| 7,311,708 B2 | 12/2007 | McClurken |
| 7,347,839 B2 | 3/2008 | Hiejima |
| 7,470,254 B2 | 12/2008 | Basta et al. |
| 7,537,595 B2 | 5/2009 | McClurken |
| 7,625,346 B2 | 12/2009 | Grigoryants et al. |
| 7,632,243 B2 | 12/2009 | Bialecki et al. |
| 7,632,262 B2 | 12/2009 | Bates |
| 7,635,357 B2 | 12/2009 | Mayer |
| 7,641,669 B2 | 1/2010 | Roychowdhury et al. |
| 7,666,166 B1 | 2/2010 | Emmert et al. |
| 7,670,317 B2 | 3/2010 | Cindrich et al. |
| 7,670,322 B2 | 3/2010 | Fangrow, Jr. |
| 7,691,093 B2 | 4/2010 | Brimhall |
| 7,695,458 B2 | 4/2010 | Belley et al. |
| 7,713,257 B2 | 5/2010 | Brimhall et al. |
| 7,736,337 B2 | 6/2010 | Diep et al. |
| 7,736,339 B2 | 6/2010 | Woehr et al. |
| 7,758,514 B2 | 7/2010 | Grigoryants et al. |
| 7,789,861 B2 | 9/2010 | Franer |
| 7,806,869 B2 | 10/2010 | Nilsson et al. |
| 7,914,494 B2 | 3/2011 | Hiejima |
| 7,914,496 B2 | 3/2011 | Brockmeier et al. |
| 7,955,346 B2 | 6/2011 | Mauch et al. |
| 8,002,750 B2 | 8/2011 | Smith |
| 8,006,953 B2 | 8/2011 | Bennett |
| 8,016,791 B2 | 9/2011 | Sugiki et al. |
| 8,029,472 B2 | 10/2011 | Leinsing et al. |
| 8,042,689 B2 | 10/2011 | Fröjd et al. |

(56) References Cited

U.S. PATENT DOCUMENTS

| | | |
|---|---|---|
| 8,048,039 B2 | 11/2011 | Carlyon et al. |
| 8,056,756 B2 | 11/2011 | Okiyama |
| 8,066,670 B2 | 11/2011 | Cluff et al. |
| 8,066,675 B2 | 11/2011 | Cindrich et al. |
| 8,123,727 B2 | 2/2012 | Luther et al. |
| 8,147,413 B2 | 4/2012 | Abraham |
| 8,147,455 B2 | 4/2012 | Butts et al. |
| 8,152,755 B1 | 4/2012 | Wach et al. |
| 8,172,757 B2 | 5/2012 | Jaffe et al. |
| 8,202,253 B1 | 6/2012 | Wexler |
| 8,206,357 B2 | 6/2012 | Bettuchi |
| 8,206,375 B2 | 6/2012 | Snow |
| 8,257,313 B2 | 9/2012 | McKinnon et al. |
| 8,257,339 B1 | 9/2012 | Rosado |
| 8,262,623 B2 | 9/2012 | Nijland et al. |
| 8,286,657 B2 | 10/2012 | Belley et al. |
| 8,308,655 B2 | 11/2012 | Grigoryants et al. |
| 8,308,691 B2 | 11/2012 | Woehr et al. |
| 8,323,249 B2 | 12/2012 | White et al. |
| 8,328,762 B2 | 12/2012 | Woehr et al. |
| 8,333,735 B2 | 12/2012 | Woehr et al. |
| 8,337,463 B2 | 12/2012 | Woehr et al. |
| 8,348,844 B2 | 1/2013 | Kunjan et al. |
| 8,361,038 B2 | 1/2013 | McKinnon et al. |
| 8,366,684 B2 | 2/2013 | Harding |
| 8,388,583 B2 | 3/2013 | Stout et al. |
| 8,419,688 B2 | 4/2013 | Woehr et al. |
| 8,454,579 B2 | 6/2013 | Fangrow, Jr. |
| 8,460,247 B2 | 6/2013 | Woehr et al. |
| 8,465,461 B2 | 6/2013 | Wu et al. |
| 8,469,928 B2 | 6/2013 | Stout et al. |
| 8,470,025 B2 | 6/2013 | Lenihan et al. |
| 8,506,533 B2 | 8/2013 | Carlyon et al. |
| 8,506,534 B2 | 8/2013 | Luther et al. |
| 8,518,013 B2 | 8/2013 | Kurrus et al. |
| 8,535,271 B2 | 9/2013 | Fuchs et al. |
| 8,540,728 B2 | 9/2013 | Woehr et al. |
| 8,562,520 B2 | 10/2013 | Rockrohr |
| 8,585,651 B2 | 11/2013 | Asai |
| 8,591,468 B2 | 11/2013 | Woehr et al. |
| 8,597,249 B2 | 12/2013 | Woehr et al. |
| 8,597,252 B2 | 12/2013 | Burkholz et al. |
| 8,608,727 B2 | 12/2013 | Michels et al. |
| 8,608,728 B2 | 12/2013 | Michels et al. |
| 8,622,972 B2 | 1/2014 | Nystrom et al. |
| 8,628,056 B2 | 1/2014 | LaBean et al. |
| 8,636,695 B2 | 1/2014 | Cluff et al. |
| 8,641,675 B2 | 2/2014 | Stout et al. |
| 8,641,676 B2 | 2/2014 | Butts et al. |
| 8,647,301 B2 | 2/2014 | Bialecki et al. |
| 8,652,104 B2 | 2/2014 | Goral et al. |
| 8,663,169 B2 | 3/2014 | Emmert et al. |
| 8,668,674 B2 | 3/2014 | White et al. |
| 8,679,063 B2 | 3/2014 | Stout et al. |
| 8,690,815 B2 | 4/2014 | Porter et al. |
| 8,690,833 B2 | 4/2014 | Belson |
| 8,715,242 B2 | 5/2014 | Helm, Jr. |
| 8,728,030 B2 | 5/2014 | Woehr |
| 8,740,850 B2 | 6/2014 | Leinsing et al. |
| 8,771,230 B2 | 7/2014 | White et al. |
| 8,790,310 B2 | 7/2014 | White et al. |
| 8,831,707 B2 | 9/2014 | Tekulve et al. |
| 8,864,715 B2 | 10/2014 | Cluff et al. |
| 8,882,742 B2 | 11/2014 | Dikeman et al. |
| 8,926,494 B1 | 1/2015 | Cook et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,939,938 B2 | 1/2015 | Funamura et al. |
| 8,968,252 B2 | 3/2015 | White et al. |
| 8,979,802 B2 | 3/2015 | Woehr |
| 8,998,852 B2 | 4/2015 | Blanchard et al. |
| 9,011,382 B2 | 4/2015 | Nilsson et al. |
| 9,028,393 B2 | 5/2015 | Farnan |
| 9,028,425 B2 | 5/2015 | Burkholz |
| 9,089,671 B2 | 7/2015 | Stout et al. |
| 9,095,679 B2 | 8/2015 | Nishimura et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,155,864 B2 | 10/2015 | Stout et al. |
| 9,180,275 B2 | 11/2015 | Helm |
| 9,186,455 B2 | 11/2015 | Moyer |
| 9,220,833 B2 | 12/2015 | Robert et al. |
| 9,227,038 B2 | 1/2016 | Woehr |
| 9,227,047 B2 | 1/2016 | Khalaj |
| RE45,896 E | 2/2016 | Stout et al. |
| 9,272,088 B2 | 3/2016 | Bornhoft |
| 9,314,201 B2 | 4/2016 | Burkholz et al. |
| 9,320,870 B2 | 4/2016 | Woehr |
| 9,327,095 B2 | 5/2016 | Ma |
| 9,352,119 B2 | 5/2016 | Burkholz et al. |
| 9,370,641 B2 | 6/2016 | Woehr et al. |
| 9,381,320 B2 | 7/2016 | Vincent et al. |
| 9,381,324 B2 | 7/2016 | Fuchs et al. |
| 9,399,116 B2 | 7/2016 | Goral et al. |
| 9,427,549 B2 | 8/2016 | Wooehr et al. |
| 9,522,266 B2 | 12/2016 | Sutton et al. |
| 9,545,632 B2 | 1/2017 | Lentz et al. |
| 9,579,486 B2 | 2/2017 | Burkholz et al. |
| 9,592,366 B2 | 3/2017 | White et al. |
| 9,623,210 B2 | 4/2017 | Woehr |
| 9,737,252 B2 | 8/2017 | Teoh et al. |
| 9,750,920 B2 | 9/2017 | Vincent et al. |
| 9,764,085 B2 | 9/2017 | Teoh |
| 9,844,648 B2 | 12/2017 | Nakajima et al. |
| 9,919,136 B2 | 3/2018 | Lim et al. |
| 9,962,525 B2 | 5/2018 | Woehr |
| 10,004,891 B2 | 6/2018 | Woehr |
| 10,080,869 B2 | 9/2018 | Woehr et al. |
| 10,166,370 B2 | 1/2019 | Woehr et al. |
| 10,173,002 B2 | 1/2019 | Tan et al. |
| 10,207,081 B2 | 2/2019 | Fuchs et al. |
| 10,286,185 B2 | 5/2019 | Tanabe et al. |
| 10,376,686 B2 | 8/2019 | Burkholz et al. |
| 10,449,331 B2 | 10/2019 | Lim et al. |
| 10,456,572 B2 | 10/2019 | Woehr |
| 10,463,395 B2 | 11/2019 | Reid et al. |
| 10,463,839 B2 | 11/2019 | Woehr |
| 10,493,262 B2 | 12/2019 | Tran et al. |
| 10,500,376 B2 | 12/2019 | Isaacson et al. |
| 10,543,343 B2 | 1/2020 | Woehr et al. |
| 10,549,072 B2 | 2/2020 | Burkolz et al. |
| 10,646,253 B2 | 5/2020 | Blanc |
| 2001/0053895 A1 | 12/2001 | Vaillancourt |
| 2002/0128604 A1 | 9/2002 | Nakajima |
| 2004/0210194 A1 | 10/2004 | Bonnette et al. |
| 2005/0256500 A1 | 11/2005 | Fujii |
| 2006/0118749 A1 | 6/2006 | Ryan et al. |
| 2006/0155245 A1 | 7/2006 | Woehr |
| 2007/0083162 A1 | 4/2007 | O'Reagan et al. |
| 2007/0225647 A1 | 9/2007 | Luther et al. |
| 2007/0233007 A1 | 10/2007 | Adams |
| 2008/0058720 A1 | 3/2008 | Spohn et al. |
| 2008/0108944 A1 | 5/2008 | Woehr et al. |
| 2008/0108976 A1 | 5/2008 | Johnson et al. |
| 2008/0208132 A1* | 8/2008 | Funamura ......... A61M 39/0693 604/167.03 |
| 2008/0300455 A1 | 12/2008 | Smith |
| 2009/0221975 A1 | 9/2009 | Rodd |
| 2010/0179480 A1 | 7/2010 | Sugiki et al. |
| 2010/0185153 A1 | 7/2010 | Sugiki et al. |
| 2010/0204648 A1* | 8/2010 | Stout ................ A61M 39/0208 604/122 |
| 2010/0280456 A1 | 11/2010 | Nijland et al. |
| 2011/0046570 A1 | 2/2011 | Stout et al. |
| 2011/0054406 A1 | 3/2011 | McKinnon |
| 2011/0282286 A1 | 11/2011 | Argentine |
| 2011/0301553 A1 | 12/2011 | Goral et al. |
| 2011/0319825 A1 | 12/2011 | Goral et al. |
| 2011/0319838 A1 | 12/2011 | Goral et al. |

(56) References Cited

U.S. PATENT DOCUMENTS

| | | |
|---|---|---|
| 2012/0016266 A1 | 1/2012 | Burkholz |
| 2012/0089101 A1 | 4/2012 | Carlyon et al. |
| 2012/0259293 A1 | 10/2012 | Bialecki et al. |
| 2012/0330238 A1 | 12/2012 | Robert et al. |
| 2013/0006223 A1 | 1/2013 | Michels et al. |
| 2013/0165868 A1 | 6/2013 | Isaacson et al. |
| 2013/0204226 A1 | 8/2013 | Keyser |
| 2013/0304026 A1 | 11/2013 | Luther et al. |
| 2014/0052065 A1 | 2/2014 | Woehr et al. |
| 2014/0107619 A1 | 4/2014 | Butts et al. |
| 2014/0135702 A1 | 5/2014 | Woehr et al. |
| 2014/0207083 A1* | 7/2014 | Pessin ............... A61M 39/0606 604/256 |
| 2014/0228775 A1 | 8/2014 | Burkholz et al. |
| 2014/0276434 A1* | 9/2014 | Woehr ............... A61M 39/0693 604/167.03 |
| 2014/0276453 A1 | 9/2014 | Woehr |
| 2014/0276462 A1 | 9/2014 | Vincent et al. |
| 2014/0288500 A1 | 9/2014 | Leinsing et al. |
| 2015/0038909 A1 | 2/2015 | Christensen et al. |
| 2015/0038910 A1 | 2/2015 | Harding et al. |
| 2015/0088095 A1 | 3/2015 | Luther et al. |
| 2015/0151085 A1 | 6/2015 | Tan et al. |
| 2015/0151088 A1 | 6/2015 | Lim et al. |
| 2015/0190570 A1 | 7/2015 | Teoh |
| 2015/0335858 A1 | 11/2015 | Woehr et al. |
| 2015/0335864 A1 | 11/2015 | Knutsson |
| 2016/0008580 A1 | 1/2016 | Woehr et al. |
| 2016/0114136 A1 | 4/2016 | Woehr |
| 2016/0114137 A1 | 4/2016 | Woehr et al. |
| 2016/0175563 A1* | 6/2016 | Woehr ............... A61M 25/0693 604/168.01 |
| 2016/0296724 A1 | 10/2016 | Goral et al. |
| 2016/0331936 A1* | 11/2016 | Lim ....................... A61M 5/158 |
| 2017/0035992 A1 | 2/2017 | Harding et al. |
| 2017/0173304 A1 | 6/2017 | Teoh |
| 2017/0326341 A1 | 11/2017 | Liska |
| 2018/0093077 A1 | 4/2018 | Harding et al. |
| 2018/0214682 A1* | 8/2018 | Woehr ............... A61M 39/0247 |
| 2018/0361119 A1 | 12/2018 | Goral et al. |
| 2018/0361120 A1 | 12/2018 | Goral et al. |
| 2019/0038870 A1 | 2/2019 | Isaacson et al. |
| 2019/0076625 A1 | 3/2019 | White et al. |
| 2019/0160264 A1 | 5/2019 | Isaacson |
| 2022/0001145 A1* | 1/2022 | Neoh ............... A61M 25/0618 |

FOREIGN PATENT DOCUMENTS

| | | |
|---|---|---|
| CN | 203724591 U | 7/2014 |
| CN | 203763665 U | 8/2014 |
| CN | 104039384 A | 9/2014 |
| CN | 104043167 A | 9/2014 |
| CN | 104415446 A | 3/2015 |
| CN | 105407959 A | 3/2016 |
| CN | 107029316 A | 8/2017 |
| CN | 212347338 U | 1/2021 |
| EP | 0875262 A2 | 11/1998 |
| EP | 1911485 A1 | 4/2008 |
| EP | 2213328 A1 | 8/2010 |
| EP | 3 097 939 A1 | 11/2016 |
| EP | 3337549 B1 | 6/2019 |
| FR | 2829396 A1 | 3/2003 |
| JP | H05-028348 U | 4/1993 |
| JP | H06-304250 A | 11/1994 |
| JP | H7-136285 A | 5/1995 |
| JP | H08-155034 A | 6/1996 |
| JP | H09-047511 A | 2/1997 |
| JP | H11-004894 A | 1/1999 |
| JP | H11-299898 A | 11/1999 |
| JP | 2005-531377 A | 10/2005 |
| JP | 2010-508905 A1 | 3/2010 |
| JP | 2012-525877 A | 10/2012 |
| JP | 2013-526338 A | 6/2013 |
| JP | 2013-533023 A | 8/2013 |
| JP | 2014-528807 A | 10/2014 |
| JP | 2016-013359 A | 1/2016 |
| JP | 2016-509916 A | 4/2016 |
| RU | 2009120995 A | 12/2010 |
| RU | 2 477 639 C2 | 3/2013 |
| WO | WO 2008/052790 A2 | 5/2008 |
| WO | WO 2010/093791 A1 | 8/2010 |
| WO | WO 2010/127846 A1 | 11/2010 |
| WO | WO 2009/041522 A1 | 1/2011 |
| WO | WO 2009/041523 A1 | 1/2011 |
| WO | WO 2013/052668 A1 | 4/2013 |
| WO | WO 2014/140265 A1 | 9/2014 |
| WO | WO 2015/1404336 A1 | 7/2015 |
| WO | WO 2015/161294 A1 | 10/2015 |
| WO | WO 2018/033626 A1 | 2/2018 |
| WO | WO 2018/077748 A1 | 5/2018 |

OTHER PUBLICATIONS

Office Action on related foreign application (JP Application No. 2019-508949) from the Japan Patent Office dated May 11, 2021.
Substantive Examination Adverse Report on related foreign application (MY Application No. PI 2018700453) from the Malaysian Patent Office dated May 12, 2021.
Non-Final Office Action on related US application (U.S. Appl. No. 16/323,379) dated May 17, 2021.
Office Action on related foreign application (MX Application No. MX/a/2018/001987) from the Mexican Institute of Industrial Property (IMPI) dated Dec. 8, 2020.
International Search Report and Written Opinion on corresponding PCT application (PCT/EP2019/085732) from International Searching Authority (EPO) dated Apr. 28, 2020.
Preliminary Office Action on related foreign application (BR Application No. 12 2019 017170-0) from the Brazilian Patent Office dated Apr. 7, 2021.
Office Action on related foreign application (CN Application No. 201680048615.9) from the National Intellectual Property Administration, P.R. China dated Mar. 9, 2021.
International Search Report and Written Opinion on corresponding PCT application (PCT/EP2017/070934) from International Searching Authority (EP) dated Oct. 25, 2017.
International Search Report and Written Opinion on related PCT application (PCT/EP2016/069619) from International Searching Authority (EP) dated Dec. 8, 2016.
International Preliminary Report on Patentability (Chapter I) on related PCT Application (PCT/EP2016/069619) from the International Searching Authority (EP) dated Mar. 1, 2018.
International Search Report and Written Opinion on related PCT application (PCT/EP2016/069643) from International Searching Authority (EP) dated Nov. 16, 2016.
International Preliminary Report on Patentability (Chapter I) on related PCT Application (PCT/EP2016/069643) from the International Searching Authority (EP) dated Mar. 1, 2018.
International Search Report & Written Opinion on related PCT application (PCT/EP2014/055089) from International Searching Authority (EPO) dated Jul. 17, 2014.
International Preliminary Report on Patentability (Chapter I) on related PCT Application (PCT/EP2014/055089) from the International Searching Authority (EP) dated Apr. 10, 2015.
International Preliminary Report on Patentability (Chapter I) on corresponding PCT application (PCT/EP2017/070934) from International Searching Authority (EPO) dated Feb. 28, 2019.
Examination Report on corresponding foreign application (AU Application No. 2016309744) from the IP Australia dated May 6, 2020.
Office Action on related foreign application (AU Application No. 2016309744) from the Australian Patent Office dated Aug. 31, 2020.
Preliminary Office Action on corresponding foreign application (BR Application No. 11 2018 002976-9) from the Brazilian Intellectual Property Office dated May 6, 2020.
Office Action on related foreign application (CN Application No. 201310650219.1) from the Chinese Intellectual Property Office dated Feb. 13, 2018.

(56) References Cited

OTHER PUBLICATIONS

Office Action on related foreign application (CN Application No. 201310650219.1) from the Chinese Intellectual Property Office dated Oct. 24, 2018.
Office Action including Search Report on corresponding foreign application (CN Application No. 201680048610.6) from the National Intellectual Property Administration, P.R. China dated Mar. 27, 2020.
Office Action including Search Report on corresponding foreign application (CN Application No. 201680048615.9) from the National Intellectual Property Administration, P.R. China dated Mar. 30, 2020.
Extended European Search Report from the European Patent Office on related EP application (EP19177030.4) dated Jun. 24, 2019.
Office Action on related foreign application (JP Application No. 2015-562191) from the Japanese Patent Office dated Apr. 25, 2017.
Office Action on related foreign application (JP Application No. 2015-562191) from the Japanese Patent Office dated Oct. 17, 2017.
Office Action on corresponding foreign application (JP Application No. 2018- 508169) from the Japanese Patent Office dated Oct. 1, 2019.
Office Action on related foreign application (JP Application No. 2018-508169) from the Japanese Patent Office dated Aug. 4, 2020.
Office Action on related foreign application (JP Application No. 2018-508170) from the Japanese Patent Office dated Jun. 23, 2020.
Office Action on related foreign application (MX Application No. MX/a/2018/001987) from the Mexican Patent Office dated Jul. 23, 2020.
Decision to Grant on corresponding foreign application (RU Application No. 2018109391/14) from the Russian Patent Office dated Oct. 14, 2019.
Supplementary Examination Report on related foreign application (SG Application No. 11201506983W) from the Intellectual Property Office of Singapore dated Jan. 29, 2016.
Non-Final Office Action on related US application (U.S. Appl. No. 14/012,568) dated Aug. 8, 2014.
Final Office Action on related US application (U.S. Appl. No. 14/012,568) dated Dec. 2, 2014.
Non-Final Office Action on related US application (U.S. Appl. No. 14/818,687) dated Feb. 10, 2016.
Office Action on related foreign application (CN Application No. 201780064583.6) from the National Intellectual Property Administration, P.R. China dated Jan. 27, 2021.
Office Action on related foreign application (CN Application No. 201680048610.6) from the National Intellectual Property Administration, P.R. China dated Feb. 20, 2021.
Office Action on related foreign application (JP Application No. 2018-508170) from the Japan Patent Office dated Mar. 2, 2021.
Extended European Search Report from European Patent Office on related EP application (EP 20172492.9) dated Nov. 5, 2020.
Preliminary Office Action on corresponding foreign application (BR Application No. BR112019003083-2) from Brazilian Patent and Trademark Office dated Dec. 10, 2021.
Decision of Rejection on related foreign application (CN Application No. 201680048615.9) from the National Intellectual Property Administration, P.R. China dated Sep. 3, 2021.
Notice of Grant on related foreign application (CN Application No. 201780064583.6) from the National Intellectual Property Administration, P.R. China dated Sep. 10, 2021.
First Examination Report on related foreign application (IN Application No. 201917005065) from Intellectual Property India dated Aug. 19, 2021.
Notice of Opposition on corresponding foreign application (EP Application/Patent No. EP19177030.4/3552652) from European Patent Office dated Jan. 20, 2022.
Examination Report on related foreign application (AU Application No. 2017312323) from IP Australia dated Sep. 30, 2021.
Final Office Action on related US application (U.S. Appl. No. 16/323,379) dated Nov. 1, 2021.
Office Action on related foreign application (KR Application No. Oct. 2019-7007579) from the Korean Intellectual Property Office dated Jun. 21, 2022.
Substantive Examination Clear Report on related foreign application (MY Application No. PI 2018700453) from the Intellectual Property Corporation of Malaysia dated Oct. 25, 2022.
Office Action on related foreign application (RU Application No. 2021121047) from the Russian Patent Office dated Mar. 22, 2023.
Office Action on related foreign application (JP Application No. 2022-031810) from the Japan Patent Office dated Mar. 28, 2023.
Office Action on related foreign application (CN Application No. 201911294423.8) from the National Intellectual Property Administration, P.R. China dated Dec. 22, 2022.
Office Action on related foreign application (IN Application No. 202117030932) from Intellectual Property India dated Feb. 17, 2023.

* cited by examiner

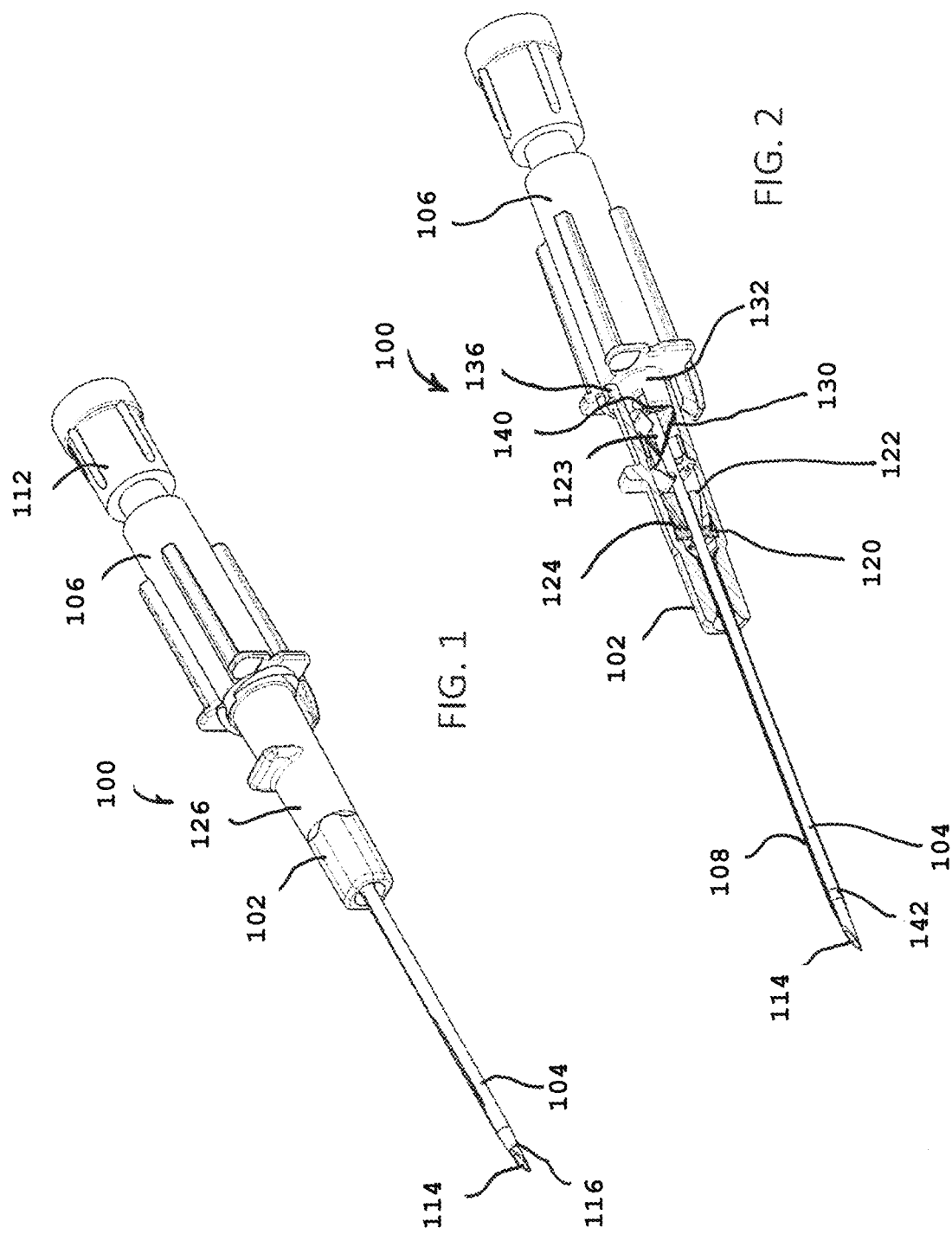

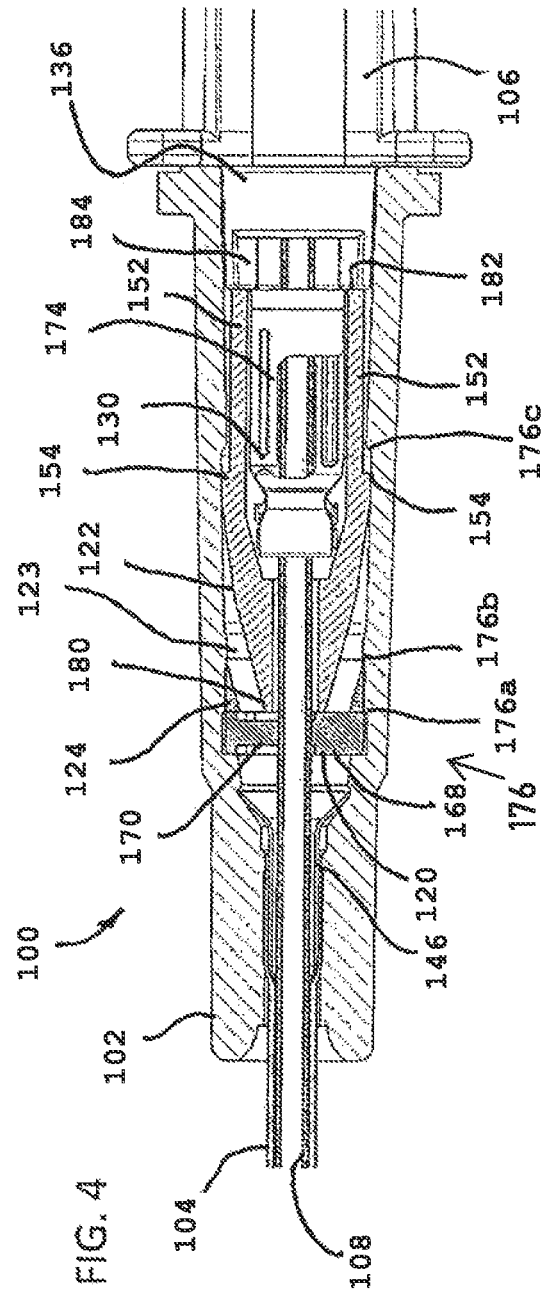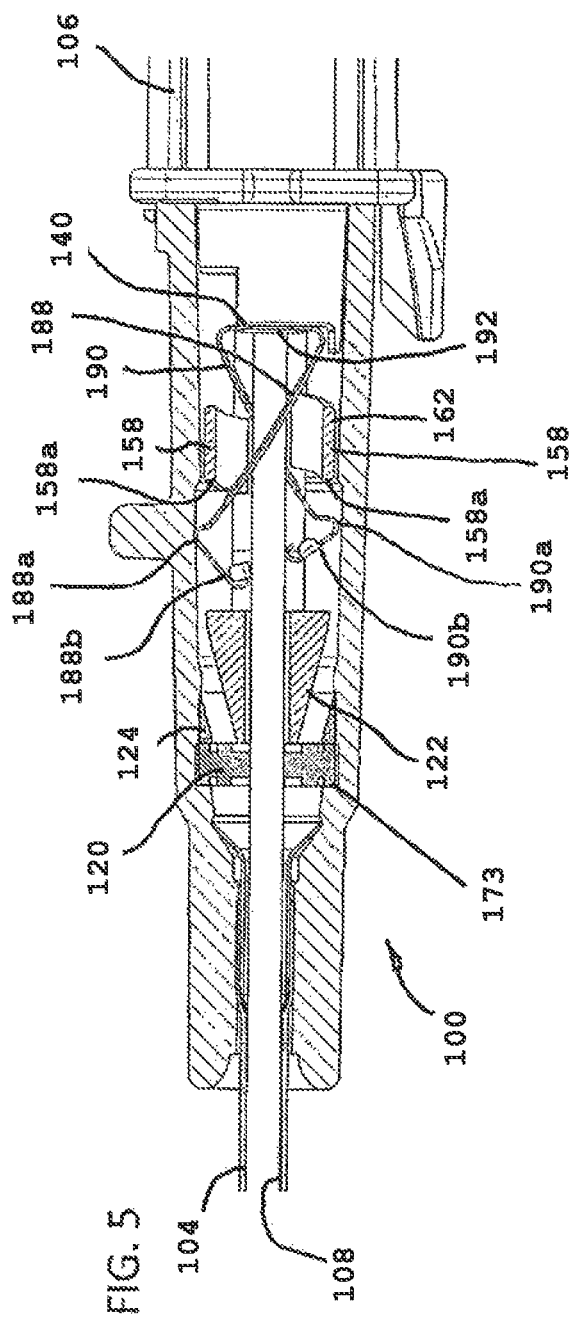

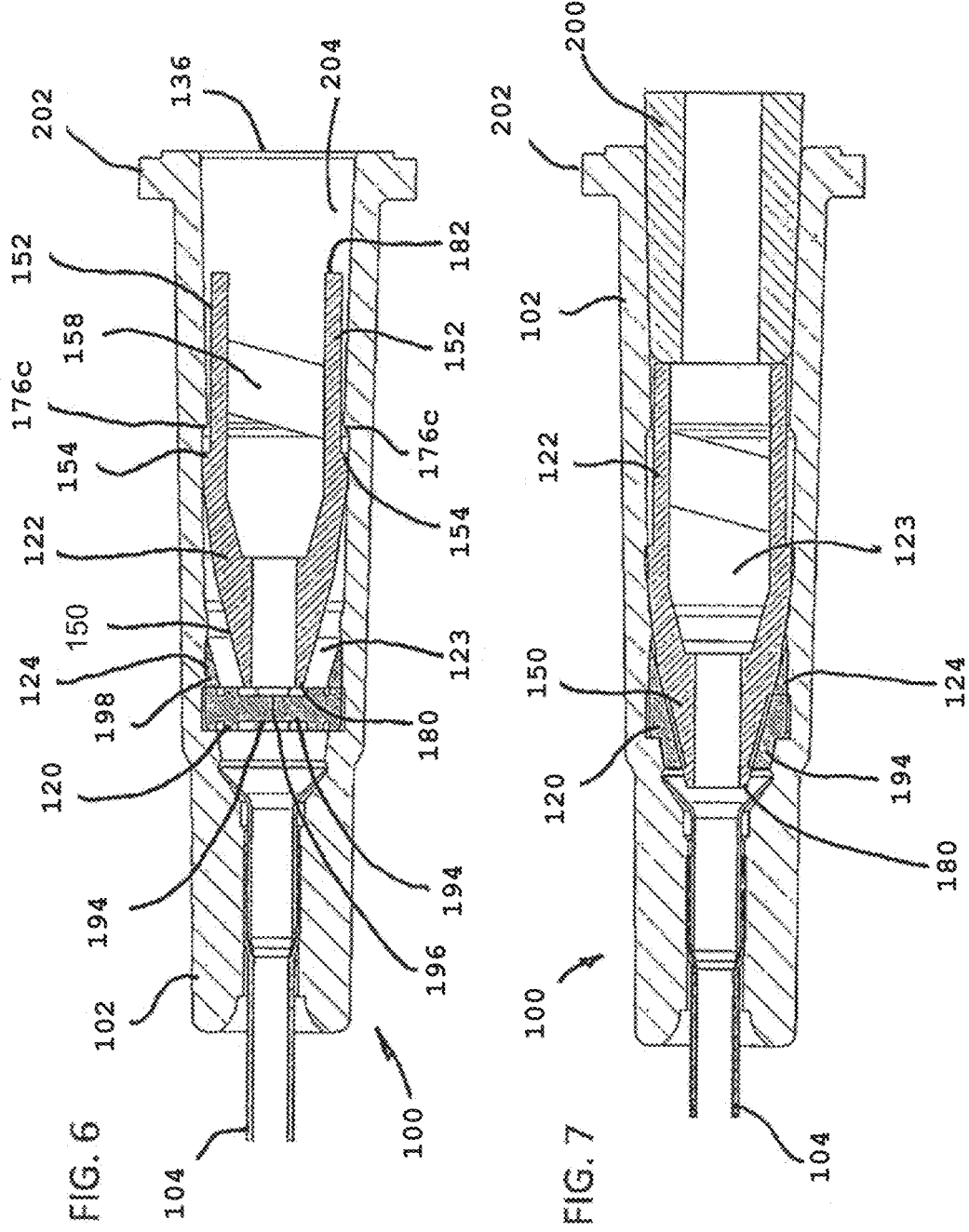

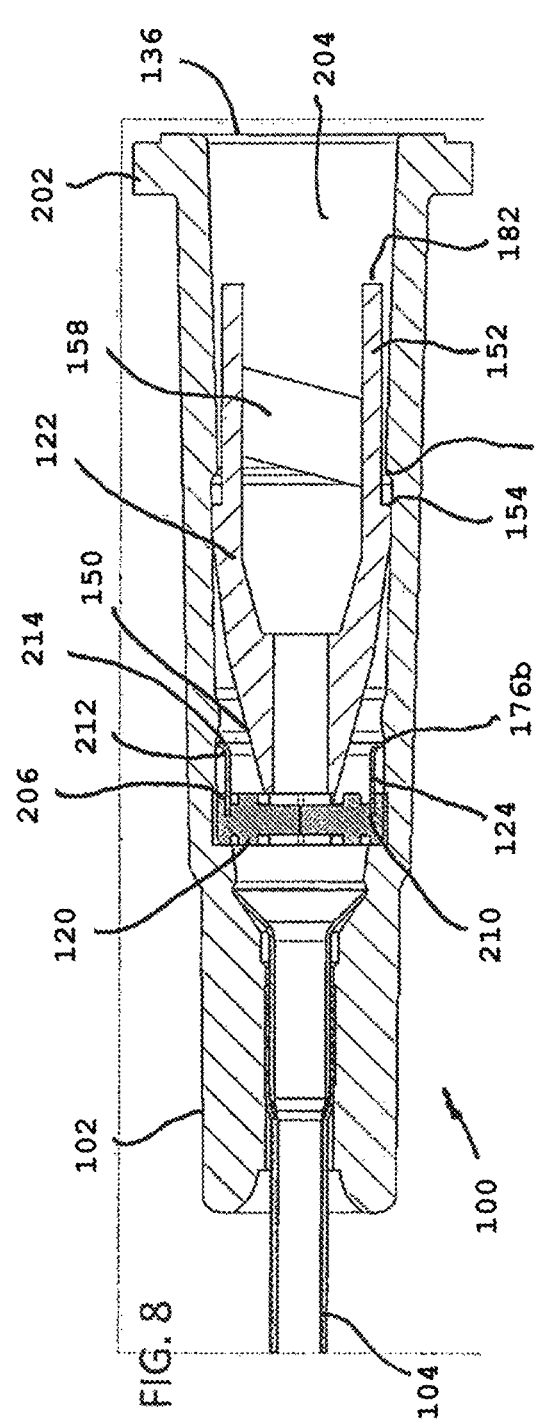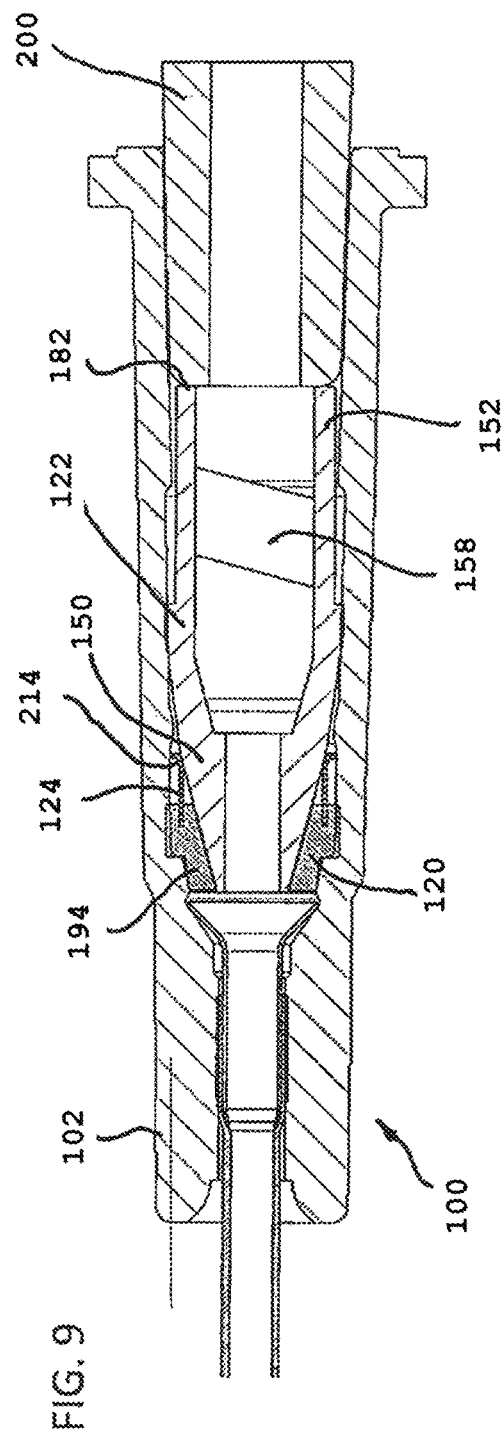

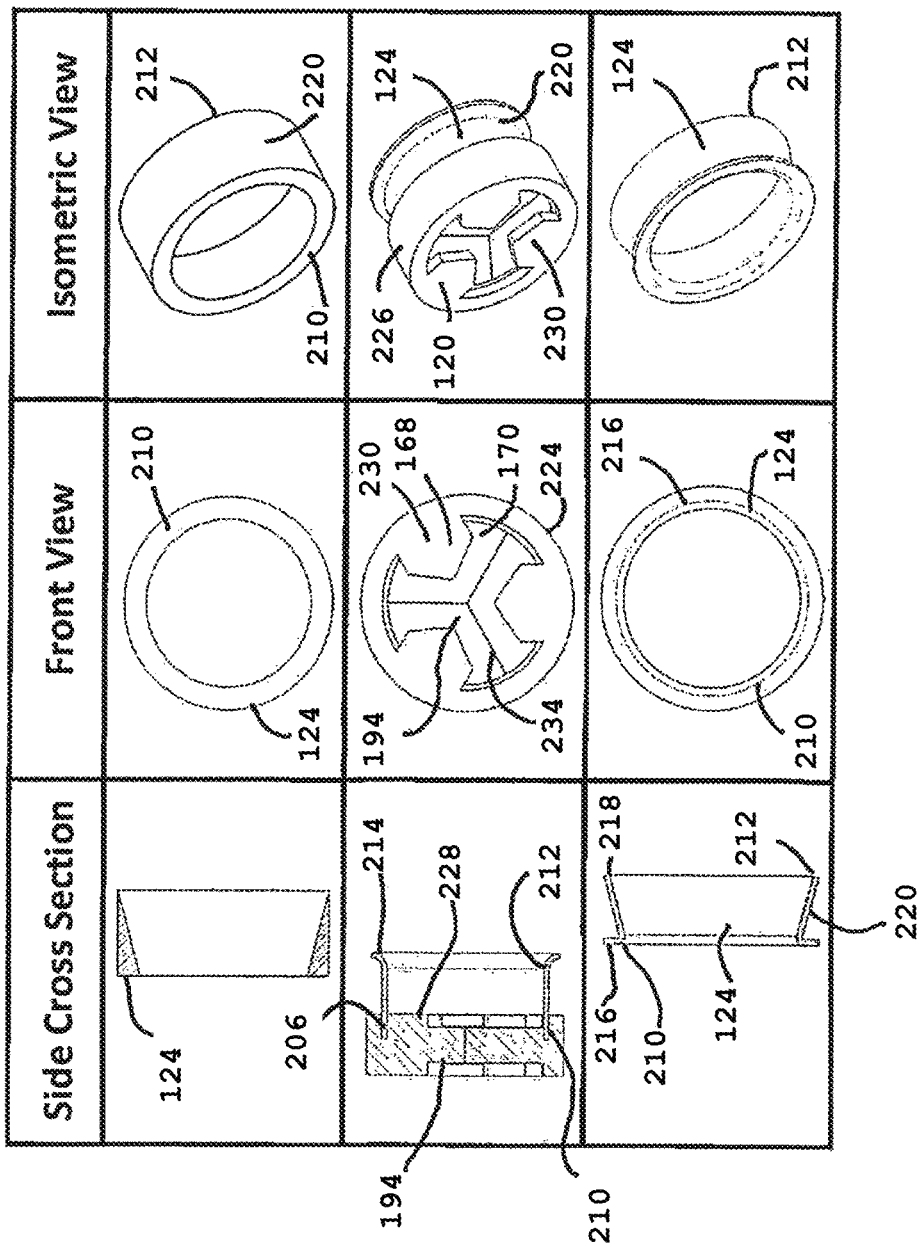

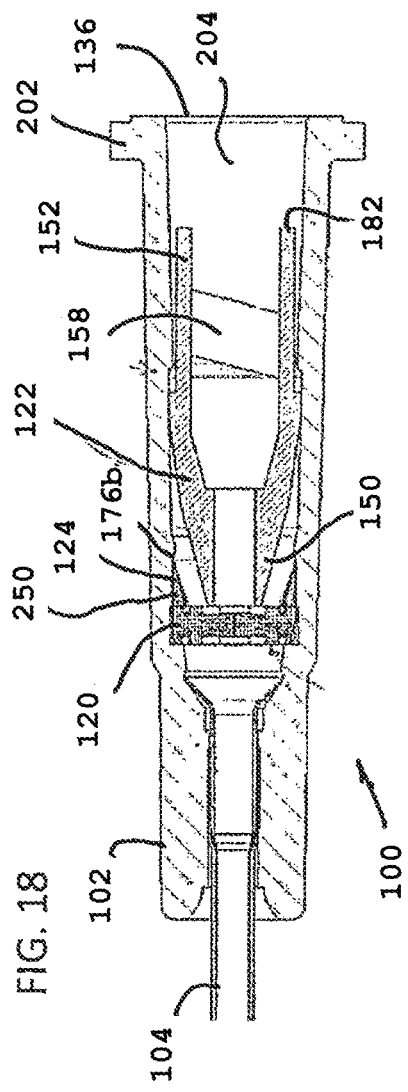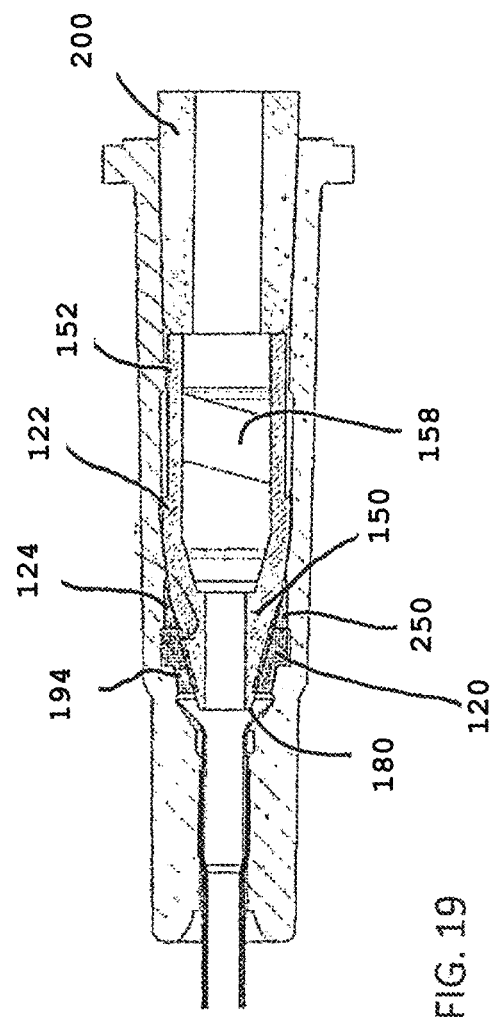
FIG. 18
FIG. 19

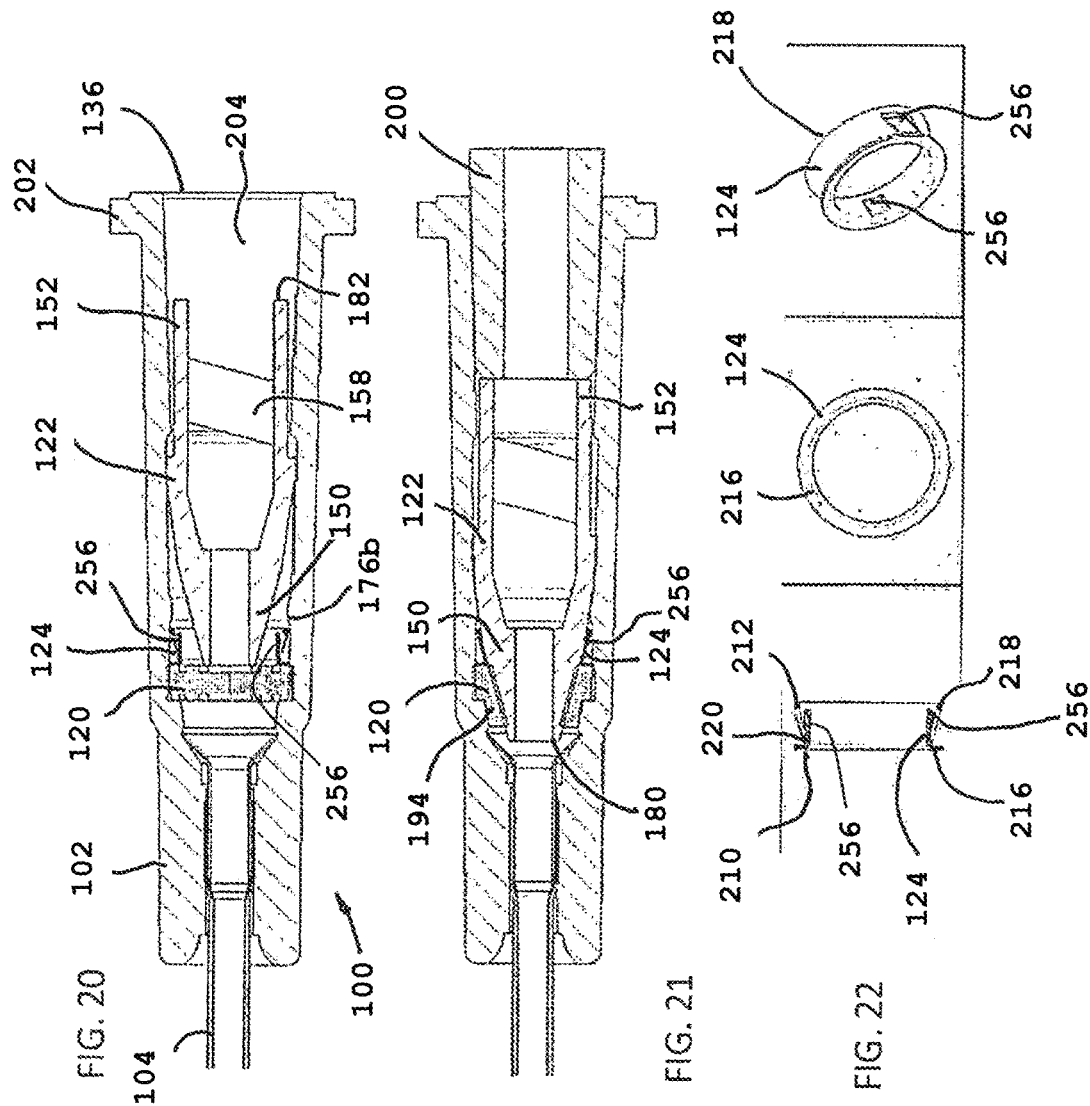

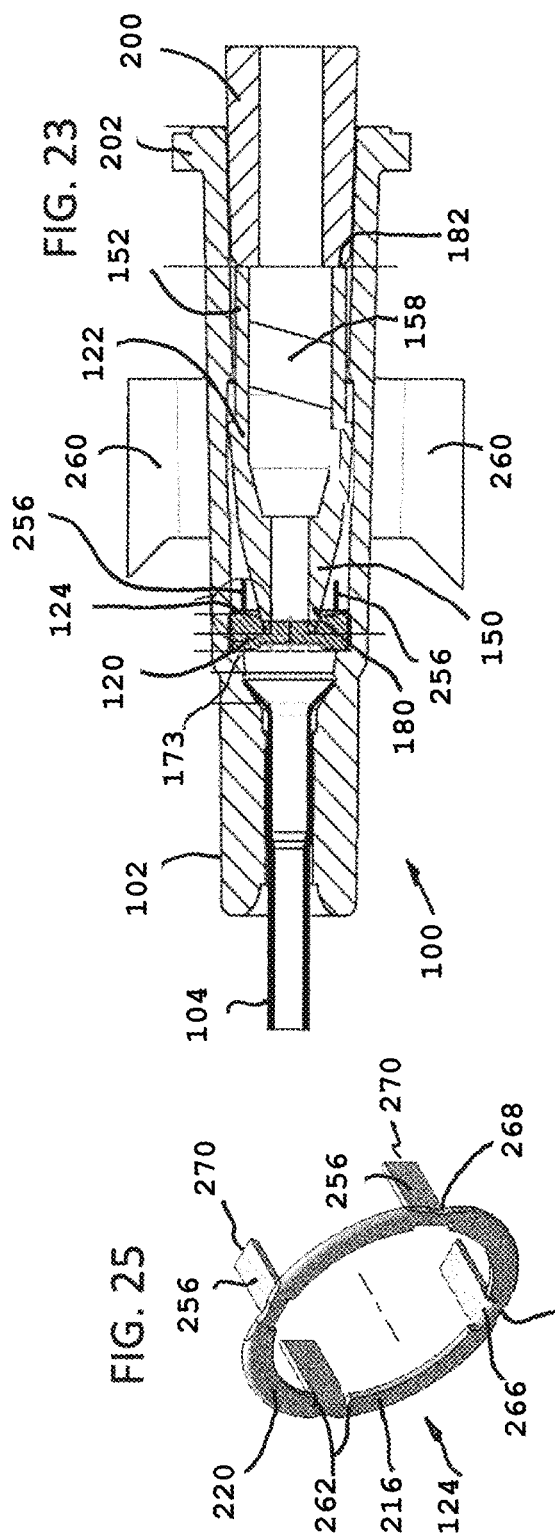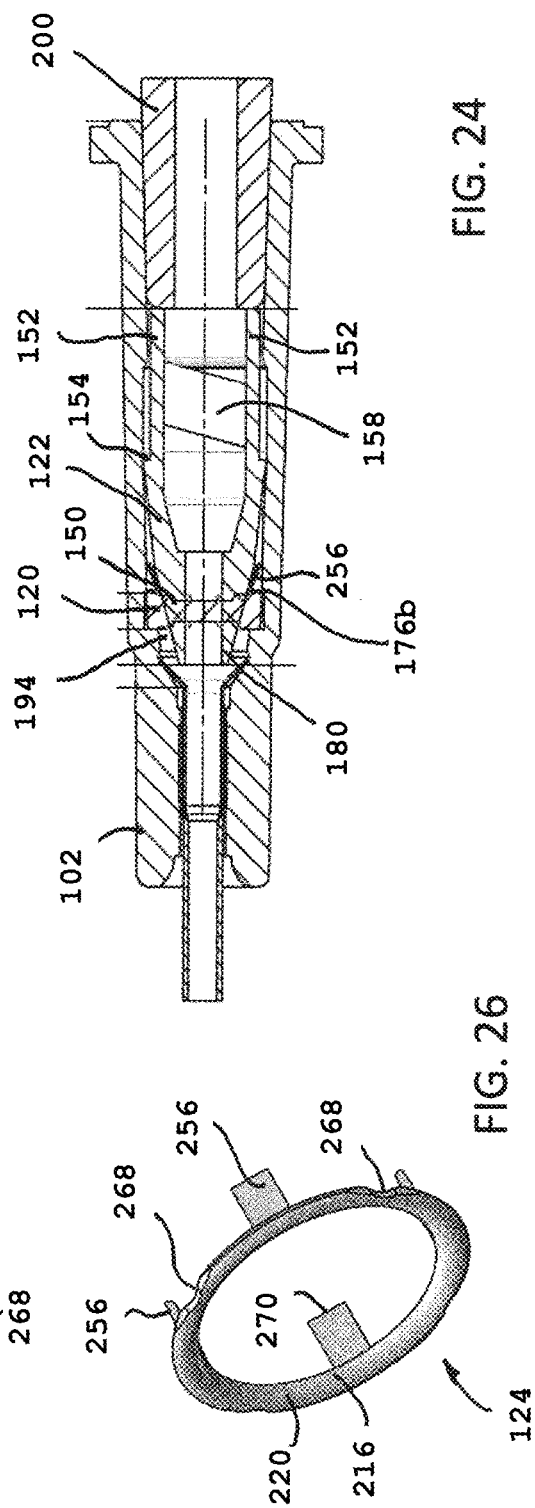

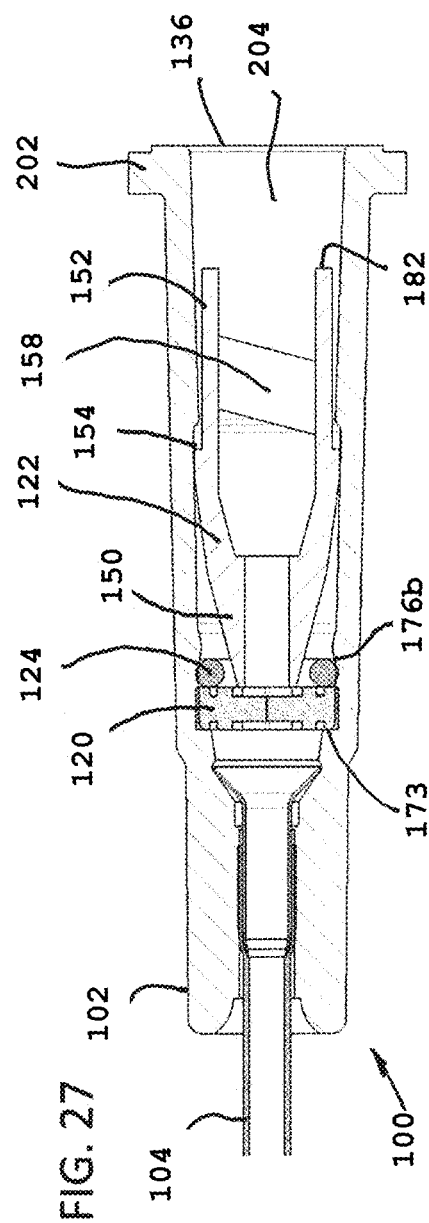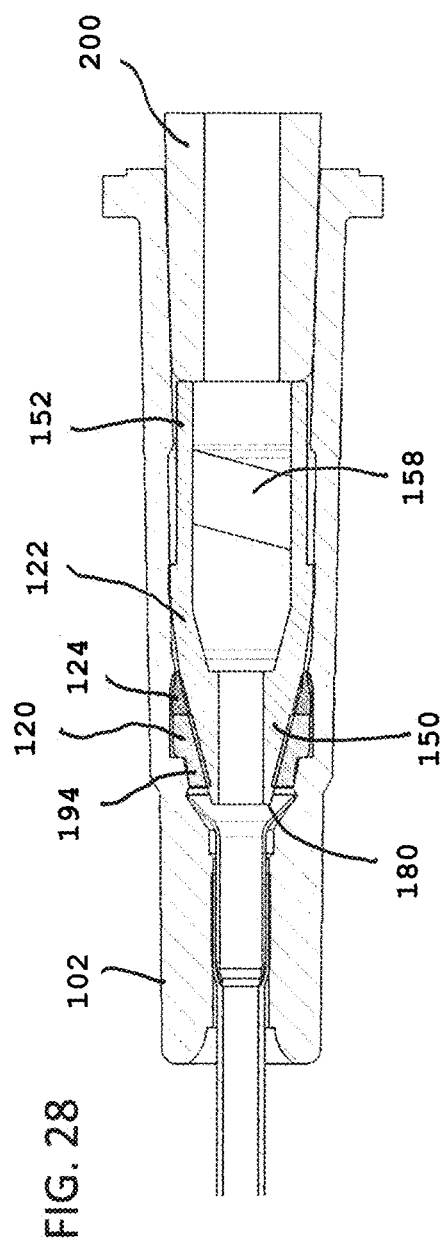

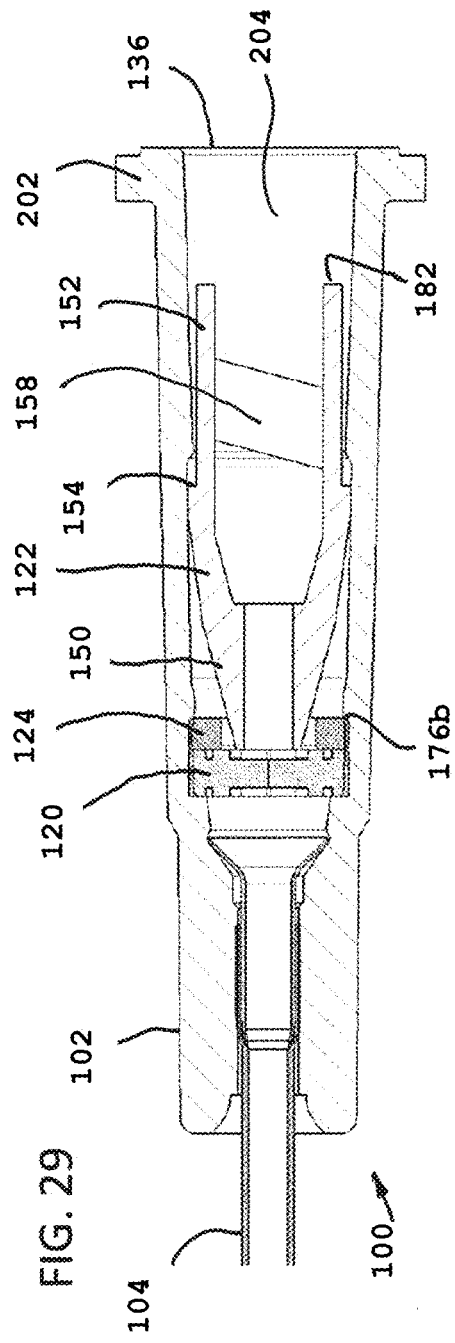

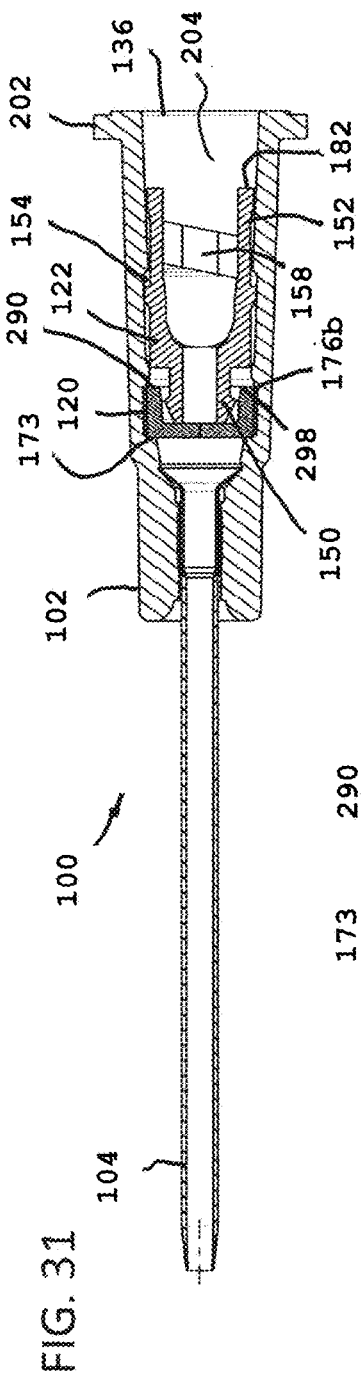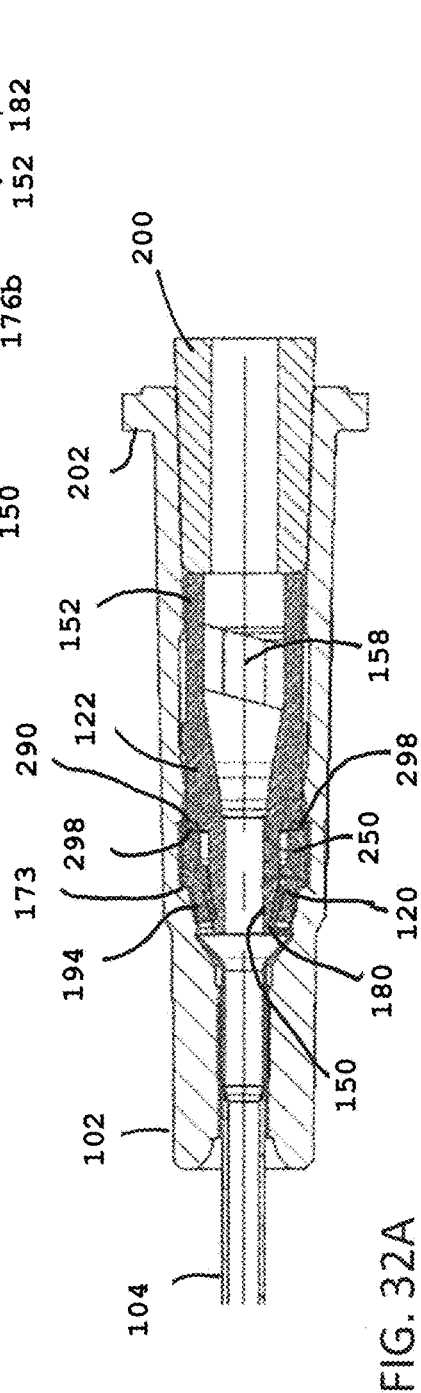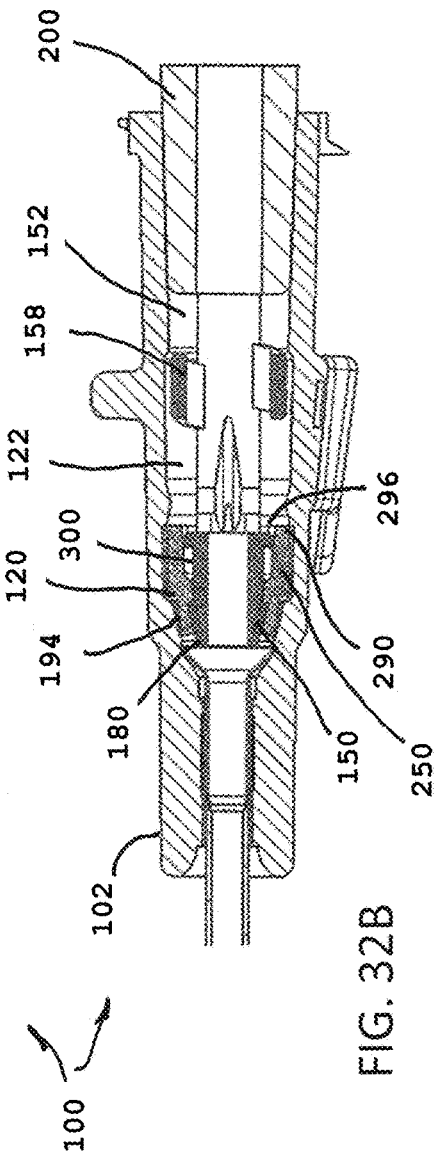

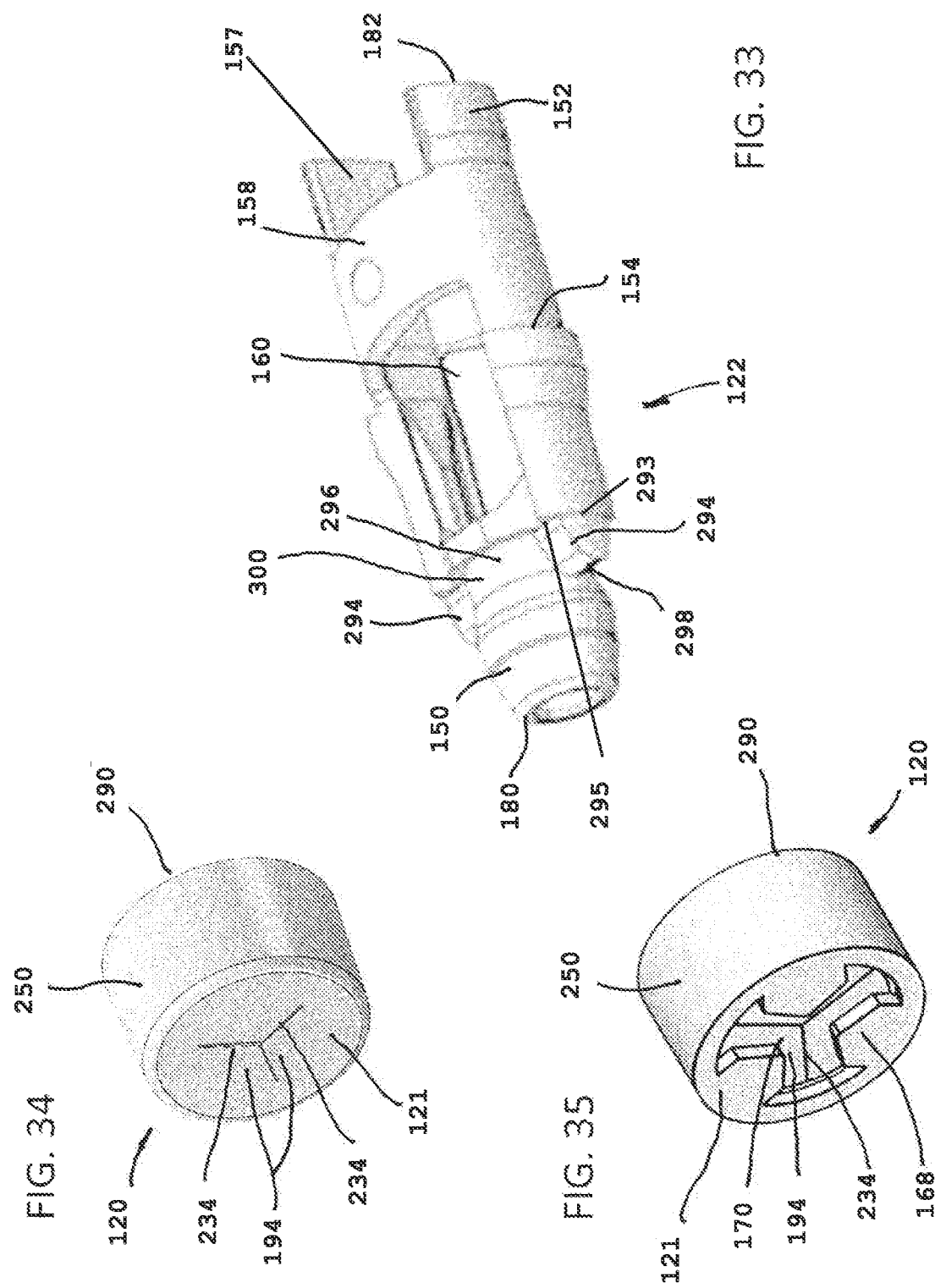

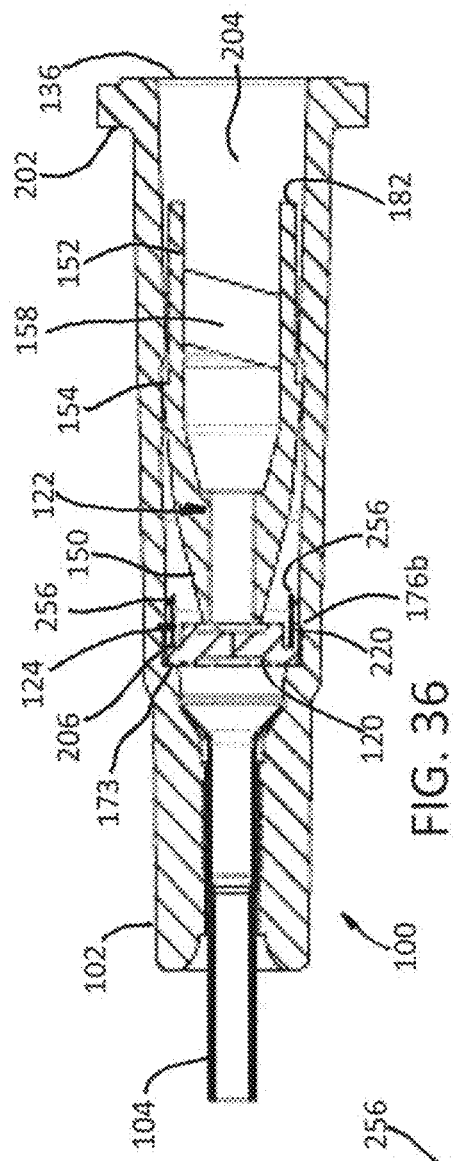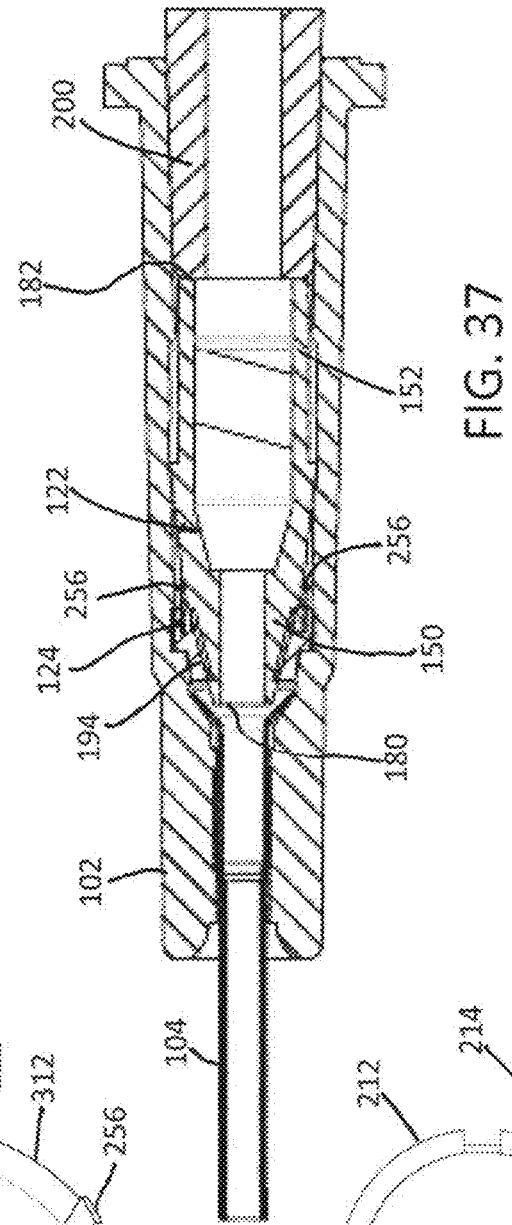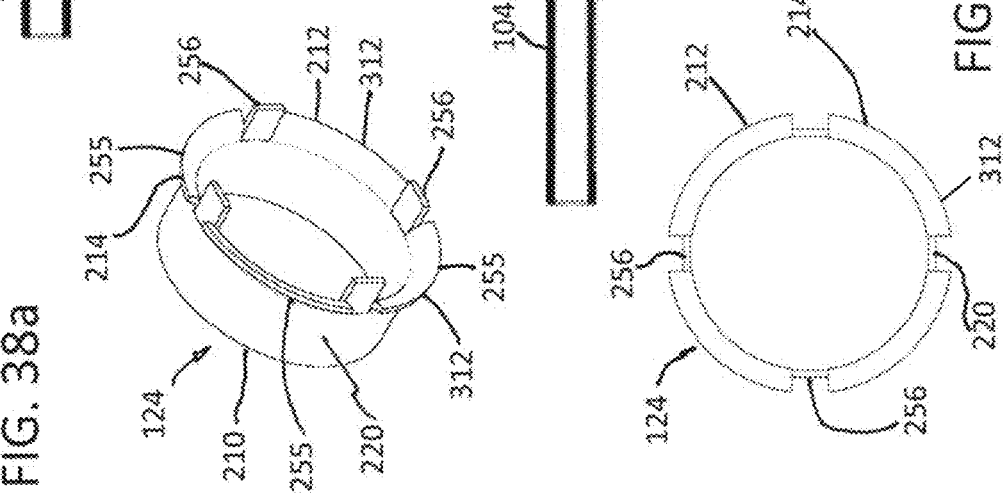

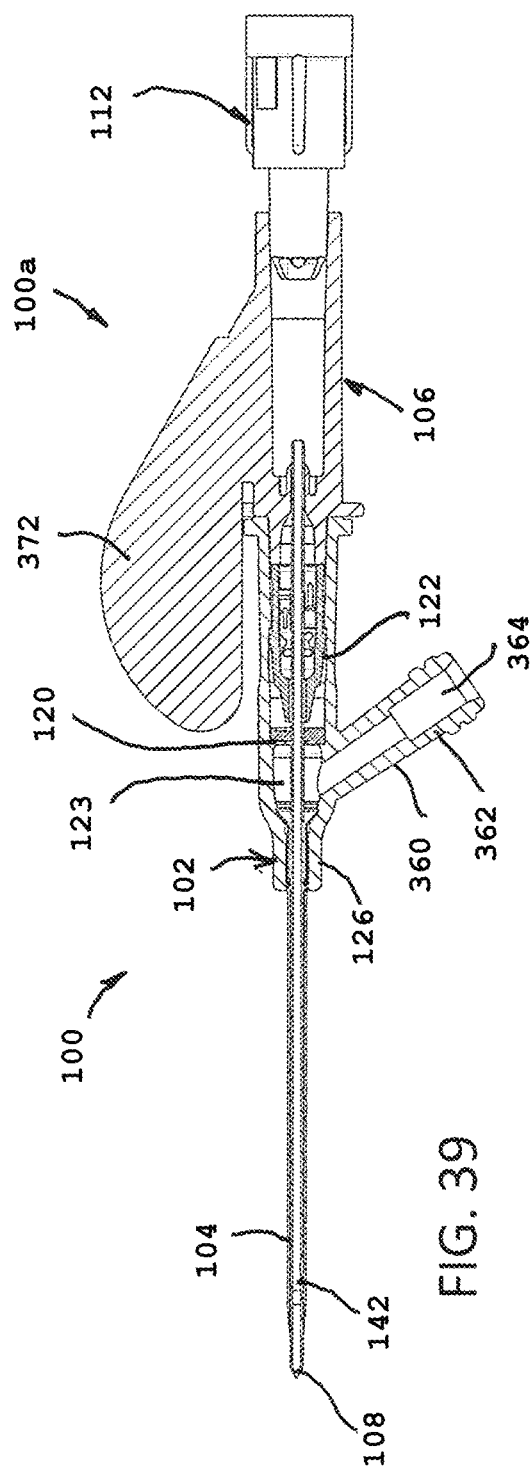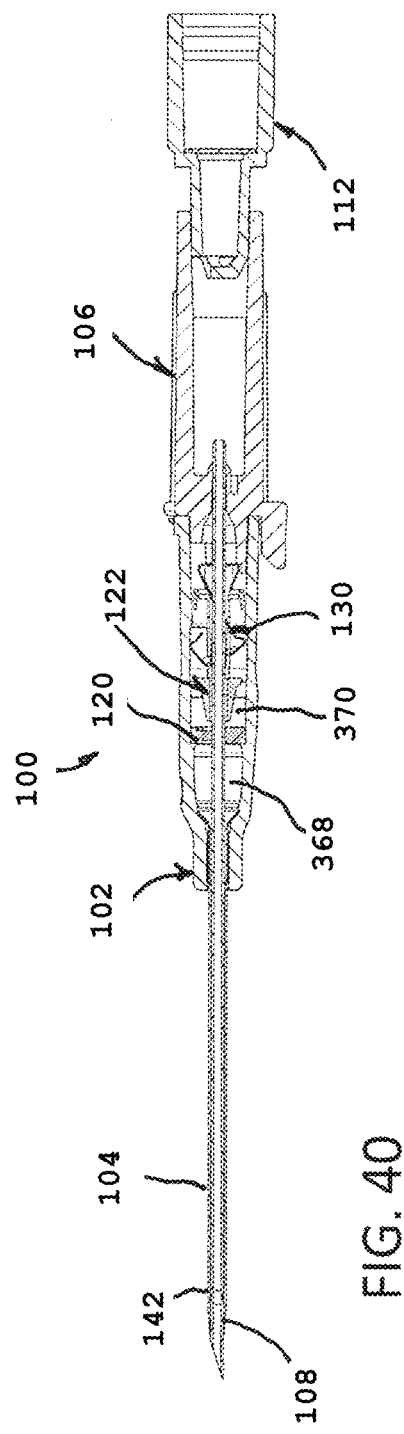
FIG. 39
FIG. 40

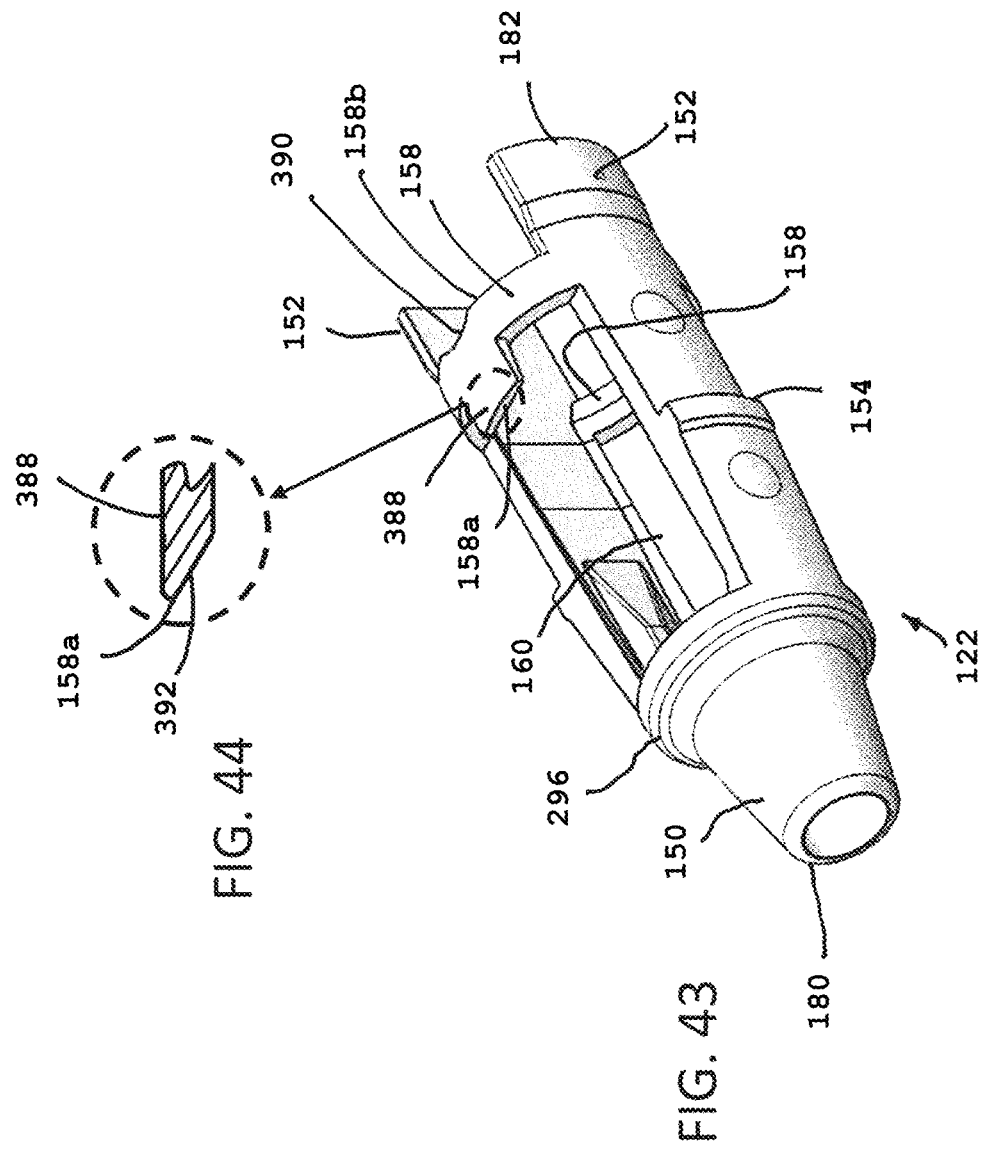

CATHETER ASSEMBLIES AND RELATED METHODS

FIELD OF ART

The present disclosure is generally related to over-the-needle catheter assemblies with specific discussions on peripheral intravenous catheter assemblies, Luer activated devices, and related methods.

BACKGROUND

Insertion procedure for an intravenous (IV) catheter assembly contains four basic steps: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand to stop the flow of blood through the catheter; and (4) the healthcare worker then tapes the exposed end of the catheter (the catheter hub) to the patient's skin and connects it to the source of the fluid to be administered into the patient's vein.

One problem is that, immediately after the withdrawal of the needle from the patient's vein, the healthcare worker, who is at this time involved in at least two urgent procedures, must place the exposed needle tip at a nearby location and address the tasks required to accomplish the needle withdrawal. It is at this juncture that the exposed needle tip creates a danger of an accidental needle stick, which, under the circumstances, leaves the healthcare worker vulnerable to the transmission of various dangerous blood-borne pathogens, including AIDS and hepatitis.

Another problem is applying digital pressure at the right position to stop the flow of blood through the catheter as and after the needle is removed. This in itself creates a risk for needle stick injuries if the elbow of the practitioner is accidently knocked as the needle is being removed or if the practitioner tries to reinsert the needle in the catheter while applying digital pressure.

Sometimes these over-the-needle catheter assemblies are used for high pressure injections for diagnostic purposes in the radiology department of a hospital. The assemblies must withstand pressures of three (3) bars or more. This includes holding the septum in place so that it can be open and closed multiple times, even after such a high-pressure application.

SUMMARY

Needle devices having a component that provides the function of fixing a valve in a standard diameter sized Luer taper catheter hub are disclosed. The component for fixing can be called a securing device and can provide a proximally directed axial force for returning a valve opener from a distal position to a proximal position when a male Luer is disconnected from a catheter hub. Various components can be located inside a single piece hub body catheter hub. The various components can include a component that restricts fluid flow, allows actuation to permit fluid flow, prevents needle injuries, and combinations thereof.

The securing device can include a structure having a surface define a bore and wherein at least part of a valve opener is located in the bore. The part of the valve opener that locates in the bore of the securing device can be so located in both a ready to use position and an activation position.

The securing device can secure a valve in an interior of the catheter hub. The valve can be a valve disc. In addition to securing the valve, the securing device can optionally be configured to exert a proximally directed force to return the valve opener, which has advanced in the distal direction to open the one or more valve flaps of the valve, from a distal position to a proximal position.

The securing device can incorporate one or more leaf springs, can itself be a coiled spring, such as a canted coil spring, can be an O-ring, or can exert a force against a pliable portion or portions of the valve opener so that the pliable portion or portions provides the proximally directed force to move the valve opener from a distal position to a proximal position.

The securing device can have a body with an exterior surface, an interior surface, a proximal end and a distal end.

Aspects of the invention is directed to a catheter assembly comprising a catheter tube having a lumen, a distal end opening, and a proximal end attached to a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a valve body comprising at least one slit, a proximally facing surface, and a distally facing surface located in the interior cavity of the catheter hub; a valve actuator disposed in the interior cavity of the catheter hub, said valve actuator having a nose section with a bore and a proximal section with at least one gap for fluid flow therethrough or thereacross and being slideable between a proximal position and a distal position inside the interior cavity when pushed by a male Luer; a securing device in contact with or integral to the valve at the proximally facing surface of the valve body for retaining the valve inside the interior cavity of the catheter hub, said securing device comprising a retainer body having an interior surface defining a bore comprising a fluid path, a distal end, and a proximal end; and a needle guard having a protective surface located to a side of the needle in a ready to use position and transitionable to a position distal of the needle tip in a protective position to cover the needle tip from an inadvertent needle stick.

The distal end of the retainer body can have an inside diameter (ID) of a first dimension and a proximal end having an ID of a second dimension, which is larger than the first dimension.

The distal end of the retainer body can have an inside diameter (ID) of a first dimension and a proximal end having an ID of a second dimension, which is smaller than the first dimension.

The securing device can be a retainer, a retention ring, a retaining skirt, an O-ring or a canted coil spring.

A further aspect of the invention is a catheter assembly comprising: a catheter tube having a lumen, a distal end opening, and a proximal end attached to a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a valve body comprising at least one slit and at least two flaps, a proximally facing surface, and a distally facing surface located in the interior cavity of the catheter hub; a valve actuator disposed in the interior cavity of the catheter hub, said valve actuator having a nose section with a bore and a proximal section with at least one gap for fluid flow therethrough or thereacross and being slideable between a proximal position and a distal position inside the interior cavity when pushed by a medical implement; a securing device comprising a retainer body having an interior surface defining a bore comprising a fluid path, a distal end, and a proximal end, said distal end of the retainer body in contact with or integral to the valve at the proximally facing surface of the valve body for retaining the valve inside the interior cavity of the catheter hub and said proximal end of the retainer body located distally of the at least one shoulder of the catheter body and restricted by the at least one shoulder from displacing in a proximal direction or said securing device is in an interference fit with the catheter hub for retaining the valve inside the interior cavity of the catheter hub; and a needle guard having a protective surface located to a side of the needle in a ready to use position and transitionable to a position distal of the needle tip in a protective position to cover the needle tip from inadvertent needlestick.

The nose section of the valve opener can have a continuous surface in the radial direction. The nose section can have a slip or a gap so that the body is not continuous along the entire circumference. A proximal section can be located proximally of the nose section. The proximal section of the valve actuator can have a gap or a fluid path way. The proximal section can have two spaced apart plunger elements.

Another feature of the invention is a catheter assembly comprising: a catheter tube having a lumen, a distal end opening, and a proximal end attached to a distal end of a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a disk shape valve body, said disk shape valve body comprising at least one slit and at least two flaps, a proximally facing surface, and a distally facing surface located in the interior cavity of the catheter hub; a valve actuator disposed in the interior cavity of the catheter hub, said valve actuator having a nose section with a bore and a proximal section with at least one gap for fluid flow therethrough or thereacross and being slideable between a proximal position and a distal position inside the interior cavity when pushed by a medical implement; a securing device comprising a metallic retainer body comprising a fluid path, a distal end, and a proximal end, said distal end of the retainer body in contact with the proximally facing surface of the disk shape valve body to retain the valve between the distal end of the catheter hub and the securing device inside the interior cavity of the catheter hub; and a needle guard having a protective surface located to a side of the needle in a ready to use position and transitionable to a position distal of the needle tip in a protective position to cover the needle tip from inadvertent needlestick.

The nose section of the valve actuator can be a contoured nose section having surfaces to compress the at least two flaps against the interior of the catheter hub, or at least deflect the valve flaps in the distal direction, and to axially compress the valve against a shoulder of the catheter hub.

Viewed more generally, the nose section of the valve actuator disclosed herein can deform the valve to impart stored energy to the valve. The nose section of the valve actuator disclosed herein can deflect the valve or bias the valve to impart stored energy to the valve.

A still further aspect of the invention is a catheter assembly comprising: a catheter tube having a lumen, a distal end opening, and a proximal end attached to a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a valve body comprising at least one slit, a proximally facing surface, and a distally facing surface located in the interior cavity of the catheter hub; a valve actuator disposed in the interior cavity of the catheter hub, said valve actuator having a distal nose section with a bore and a proximal section with at least one gap for fluid flow therethrough or thereacross and being slideable between a proximal position and a distal position inside the interior cavity when pushed by a male Luer tip of a medical implement; and a canted coil spring comprising a plurality of coils positioned on the proximally facing surface side of the valve and configured to be compressed by the valve actuator when the valve actuator is pushed to the distal position by a male Luer and to expand to return the valve actuator to the proximal position.

The catheter assembly can comprise a needle guard having a protective surface located to a side of the needle in a ready to use position and transitionable to a position distal of the needle tip in a protective position to cover the needle tip from inadvertent needlestick.

Another feature of the invention is a catheter assembly comprising: a catheter tube having a lumen, a distal end opening, and a proximal end attached to a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a valve body comprising at least one slit and at least two flaps, a proximally facing surface, and a distally facing surface located in the interior cavity of the catheter hub; a valve actuator disposed in the interior cavity of the catheter hub, said valve actuator having a distal nose section with a bore and a proximal section with at least one gap for fluid flow therethrough or thereacross and being slideable between a proximal position and a distal position inside the interior cavity when pushed by a medical implement; and a retaining skirt section formed with the valve, said retaining skirt section having an outer surface directly facing the interior surface of the catheter hub and an inner surface directly facing the nose section of the valve actuator, wherein the retaining skirt section is sized and shaped to be compressed between the interior surface of the catheter hub and the nose section of the valve actuator when the valve actuator is pushed to the distal position by a male Luer tip of a medical implement and to expand to return the valve actuator to the proximal position, when the male Luer tip of the medical implement is disconnected.

The skirt section can be sized and shaped to be deformed or biased by the nose section of the valve actuator when the valve actuator is pushed to the distal position by a male Luer tip of a medical implement and the skirt section expands to return the valve actuator to the proximal position, when the male Luer tip of the medical implement is disconnected. The skirt section can be sized and shaped to change from a first size by the nose section of the valve actuator when the valve actuator is pushed to the distal position by a male Luer tip of a medical implement to a second size, which is smaller than the first size, and the skirt section expands to return the valve actuator to the proximal position, when the male Luer tip of the medical implement is disconnected. The size that changes can be any dimension of the skirt section that undergoes a physical transformation.

The valve disc can have two or more valve flaps, such as three valve flaps, that are sized and shaped to be deformed, biased, or deflected by the nose section of the valve actuator when the valve actuator is pushed to the distal position by a male Luer tip of a medical implement and the two or more valve flaps expand or un-bias to return the valve actuator to the proximal position, when the male Luer tip of the medical implement is disconnected. The valve flaps can be sized and shaped to change from a first size by the nose section of the valve actuator when the valve actuator is pushed to the distal position by a male Luer tip of a medical implement to a second size, which is smaller than the first size, and the valve flaps expand or un-bias to return the valve actuator to the proximal position, when the male Luer tip of the medical implement is disconnected. The size that changes can be any dimension of the valve flaps that undergo a physical transformation, such as being straight to being bent and taking on a smaller physical profile.

A still yet further aspect of the invention is a catheter assembly comprising: a catheter tube having a lumen, a distal end opening, and a proximal end attached to a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a disk shape valve body, said disk shape valve body comprising at least one slit and at least two flaps, a proximally facing surface, and a distally facing surface located in the interior cavity of the catheter hub; a valve actuator disposed in the interior cavity of the catheter hub, said valve actuator having a nose section and a proximal section with at least one gap for fluid flow therethrough or thereacross and being slideable between a proximal position and a distal position inside the interior cavity when pushed by a medical implement; and a securing device comprising a metallic retainer body comprising a fluid path, a distal end, a proximal end, and one or more leaf springs configured to impart a proximally directed axial force vector to the nose section of the valve actuator.

The catheter body of a catheter hub in accordance with the invention can be made from a single hub body with an outside diameter surface substantially smaller than Luer threads.

The single hub body can have a distal end having a catheter tube extending therefrom and a proximal end having a female Luer. The single hub body can be singularly formed.

A protrusion for pushing with a fingertip can be incorporated and can extend from the top of the catheter hub beyond the outside diameter of the Luer Threads.

Another feature of the invention is a catheter assembly in which a proximally directed axial force is imparted by a securing device, a valve, or both the securing device and the valve against a valve opener to move the valve opener from a distal position to a proximal position.

The invention can include a method of making or of using a catheter assembly in which a proximally directed axial force is imparted by a securing device, a valve, or both the securing device and the valve against a valve opener to move the valve opener from a distal position to a proximal position.

The invention can further include a method for forming and for using a catheter assembly provided herein.

Yet another feature of the invention can include a catheter assembly comprising: a needle attached to a needle hub; a catheter tube attached to a catheter hub; a valve and a valve actuator located inside an interior of the catheter hub, said valve comprising a split disc valve portion; and a securement device for retaining the valve inside the interior; wherein the valve actuator is movable into the valve to open the split disc valve portion in a valve opened position and movable away from the valve to enable the split disc valve portion to return to a valve closed position multiple times; and wherein the needle projects through the valve, the valve actuator, the catheter hub, and the catheter tube in a ready to use position.

The securing device disclosed herein can be positioned proximally adjacent the valve or proximally integral with the valve for retaining the valve inside the catheter hub.

The retention ring or securing device of the invention can comprise one or more leaf springs.

The retention ring or securing device of the invention can comprise a flange and two or more leaf springs extending from the flange.

The at least one leaf spring of the securing device can extend from the inside diameter of a flange and in the proximal direction, from a position radially outwardly of the inside diameter and in the proximal direction, or from a position radially inwardly of the inside diameter and in the proximal direction.

A proximal end of the at least one leaf spring can flare or bend radially outwardly, away from a centerline extending lengthwise through the securing device.

The catheter assembly can have a catheter hub comprising a wall having an exterior surface and an interior surface defining a bore and Luer threads or Luer lugs at a proximal Luer opening.

An outer circumference of the exterior surface of the catheter hub can be smaller than an exterior profile of the Luer threads or Luer lugs.

The valve actuator described herein can be movable into the valve when a male Luer tip is connected to the catheter hub and movable away from the valve when the male Luer tip is disconnected from the catheter hub. The valve actuator can move from a distal position to a proximal position via force vectors generated by the valve, by force vectors generated by the securing device, or by both the valve and the securing device.

The valve can undergo at least three actuation cycles with each actuation cycle comprising movement of a valve opener into the valve to deflect the valve flaps and movement away from the valve as the valve closes.

A further aspect of the invention can include a catheter assembly comprising a catheter tube having a lumen, a distal end opening, and a proximal end attached to a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a valve body comprising at least one slit, a proximally facing surface, and a distally facing surface located in the interior cavity of the catheter hub abutting a first shoulder at the distally facing surface of the valve; a securing device in abutting contact with the proximally facing surface of the valve body and against the interior cavity of the catheter hub for retaining the valve inside the interior cavity of the catheter hub, said securing device comprising an elastomeric material having resilient properties for storing energy when deformed; a valve actuator disposed in the interior cavity of the catheter hub, said valve actuator having a nose section with a bore for fluid flow and a proximal section with a structure with at least one gap for fluid flow therethrough or thereacross and being slideable between a proximal position and a distal position inside the interior cavity when pushed by a male Luer; said valve actuator comprising a projection for abutting a second shoulder to limit proximal travel of the valve actuator; wherein the valve actuator comprises a transition section located proximally of the nose section and at least one actuating element located proximally of the transition section.

The securing device can abut the interior cavity of the catheter hub by way of interference with the inside diameter of the catheter hub, without an internal shoulder to abut against.

The securing device can abut the interior cavity of the catheter hub by way of abutting against an internal shoulder.

The securing device can be an O-ring comprising a round cross-section, an oval cross-section, or a polygonal cross-section. A specific polygonal cross-section can include a square cross-section or a rectangular cross-section, with four sides.

The structure of the valve actuator can comprise two spaced apart actuating elements.

A stabilizing element can connect the two actuating elements together and wherein a through opening is defined distal of the stabilizing element. In some examples, a second stabilizing element can connect the two actuating elements together to define a second through opening.

A needle guard can be located at least partially within the through opening of the valve actuator. The needle guard can be located at least partially within the second through opening of the valve actuator.

The nose section of the valve opener or actuator can be spaced from the O-ring prior to advancement of the valve actuator by a male Luer tip.

The nose section of the valve opener or actuator can be spaced from the securing device prior to advancement of the valve actuator by a male Luer tip.

The valve can comprise a plurality of valve flaps and wherein the plurality of valve flaps and the securing device can have stored energy when deformed by the valve actuator.

The stored energy of both the plurality of valve flaps and the securing device can exert proximally directed forces on the valve actuator to move the valve actuator from a distal position to a proximal position.

Another aspect of the invention can include a catheter assembly comprising: a catheter tube having a lumen, a distal end opening, and a proximal end attached to a catheter hub, said catheter hub comprising a catheter body with an exterior surface and an interior surface defining an interior cavity; a needle having a needle tip at a distal end and having a proximal end attached to a needle hub; said needle projecting through the catheter hub and through the catheter tube and having the needle tip projecting distally of the distal end opening in a ready to use position; a valve having a valve body comprising at least one slit and at least two flaps, a proximally facing surface, and a distally facing surface located in the interior cavity of the catheter hub and abutting a first shoulder at the distally facing surface; a valve actuator disposed in the interior cavity of the catheter hub, said valve actuator having a nose section with a bore for fluid flow and a proximal section with a structure with at least one gap for fluid flow therethrough or thereacross and being slideable between a proximal position and a distal position inside the interior cavity when pushed by a medical implement; a securing device comprising a ring body comprising a flange having an outside diameter, an inside dimeter, a thickness between a proximally facing surface and a distally facing surface, at least one leaf spring extending from proximate the inside diameter of the flange and extending in a proximal direction; said flange being in contact with the proximally facing surface of the valve and the interior cavity of the catheter hub, said leaf spring being spaced from said interior surface and said nose section in a proximal position of the valve actuator; and wherein the at least one leaf spring has a length, a width and a thickness and wherein the thickness of the spring is approximately equal to the thickness of the flange.

The securing device can be an eyelet comprising a flange and at least two leaf springs extending from the flange. There can be three leaf springs, four leaf springs, five leaf springs, or more.

The at least one leaf spring can extend from the inside diameter of the flange of the eyelet and in the proximal direction, from a position radially outwardly of the inside diameter and in the proximal direction, or from a position radially inwardly of the inside diameter and in the proximal direction.

The flange of the securing device can have an arc cross-section such that the distally facing surface has a convex surface and the proximally facing surface has a concave surface.

The securing device can have at least one leaf spring extending proximate the inside diameter of the flange having the arc cross-section.

The securing device can remain inside the interior cavity of the catheter hub through interference with the interior surface of the catheter hub. Optionally, the securing device can abut against an internal shoulder of the catheter hub to remain inside the interior of the catheter hub.

The flange and the leaf springs can be formed from the same metal sheet. The flange and the leaf springs can be unitarily formed. The flange can have a thickness and each leaf spring can have a thickness and wherein the thickness of the flange and the thickness of each leaf spring are the same or approximately the same, to within manufacturing tolerance thickness of the metal sheet.

A needle guard located between two actuating elements of the valve actuator. The needle guard can have at least one arm and a proximal wall with a perimeter defining an opening.

A change in profile on the needle can engage the perimeter on the proximal wall of the needle guard.

A pair of slits or cut outs can be located on either side of the at least one leaf spring of the eyelet.

A cut-out can extend across at least two points of an outer arc of the flange of the eyelet.

The cut-out can be aligned along a different radian than the at least one leaf spring.

The securing device can comprise three spaced leaf springs extending proximate the inside diameter of the flange in the proximal direction.

At least two cut-outs can be provided on the outside diameter of the flange of the eyelet with the three spaced apart leaf springs with each cut-out extending across at least two points of an outer arc of the flange.

The length of a leaf spring provided with a securing device can be shorter than a length of the nose section. The leaf spring can contact the nose section only when pushed by the valve actuator, and no other part or parts of the valve actuator.

A still yet further aspect of the invention can include a catheter assembly comprising: a catheter tube having a lumen, a distal end opening, and a proximal end attached to a distal end of a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a valve disc and a skirt section extending from the valve disc, the valve disc comprising at least one slit and at least two flaps, a proximally facing surface, and a distally facing surface and said skirt section having a wall with an exterior surface and an interior surface defining a skirt interior and a skirt proximal end surface, said valve located in the interior cavity of the catheter hub with said distally facing surface contacting a first shoulder and said skirt section contacting said interior cavity; a valve actuator disposed in the interior cavity of the catheter hub, said valve actuator having a nose section with an actuation end at the distal most end of the nose section and a bore for fluid flow, two spaced apart shoulders located proximally of the actuation end with each shoulder of the valve actuator comprising an abutting edge, and a proximal section with at least one gap for fluid flow therethrough or thereacross and being slideable between a proximal position and a distal position inside the interior cavity when pushed by a medical implement, said nose section located at least in part inside the skirt interior in the ready to use position; wherein said abutting edges of said two spaced apart shoulders of the valve actuator are located proximally of the skirt proximal end surface in the ready to use position for pushing against said skirt section when said valve actuator is advanced by a male Luer tip.

A needle guard having a protective surface can be located to a side of the needle in the ready to use position and transitional to a position distal of the needle tip in a protective position to cover the needle tip from an inadvertent needlestick.

The skirt section can have a generally cylindrical shape with a ramp-shape cross-section and wherein a proximal end surface can be located at the proximal end of the ramp-shape cross-section.

The skirt section of the valve can abut a second shoulder inside the interior cavity of the catheter hub.

The wall of the skirt section can have a thickness and wherein the skirt proximal end surface can be exposed radially inwardly of the second shoulder.

The nose section of the valve actuator can have a first slope extending into a transition section and wherein the transition section can have a second slope and wherein the second slope and the first slope have different slope values.

The nose section of the valve actuator can have a first slope extending into a transition section and wherein the transition section can have a constant diameter section with no slope.

The valve disc can have a first portion with a first thickness and a second portion with a second thickness and wherein the first thickness is greater than the second thickness.

The one or more slits for forming two or more valve flaps can be formed through the second portion with the second thickness of the valve disc.

Yet another aspect of the invention is a catheter assembly comprising: a catheter tube having a lumen, a distal end opening, and a proximal end attached to a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a disk shape valve body, said disk shape valve body comprising at least one slit and at least two flaps, a proximally facing surface, and a distally facing surface located in the interior cavity of the catheter hub; a valve actuator disposed in the interior cavity of the catheter hub, said valve actuator having a nose section and a proximal section with at least one gap for fluid flow therethrough or thereacross and being slideable between a proximal position and a distal position inside the interior cavity when pushed by a medical implement; and a securing device located proximally of the valve, said securing device comprising a metallic ring body comprising a fluid path, a distal end, a proximal end, and at least one leaf spring formed at the metallic ring body and extending proximally inward of a proximal curved lip.

The ring body of the securing device can have a proximal edge and wherein at least two cuts are formed through the proximal edge to form at least one leaf spring.

The securing device can comprise three spaced leaf springs.

The at least one leaf spring can be hinged or pivotable about the metallic ring body of the securing device or the flange.

The at least one leaf spring is separated from the metallic ring body by at least one slit or cut.

The securing device can have a proximal section spaced between two adjacent leaf springs, and wherein the proximal section can have a width that is larger than a width of any of the leaf springs.

The at least one leaf spring can be spaced from the interior surface of the catheter hub when the securing device is located inside the catheter hub to support or secure the valve.

The at least one leaf spring can be spaced from the nose section of the valve actuator in the proximal position of the valve actuator and can contact the nose section of the valve actuator in a distal position of the valve actuator.

There can be two or more leaf springs formed by cutting at least four cuts or cut outs through the proximal edge of the ring body. As the proximal edge of the ring body is cut or cut out, proximal sections can be formed at the proximal end of the ring body. A proximal section can be located between two adjacent leaf springs. The proximal section or sections of the ring body allow the curved lip of the ring body to flex during installation of the securing device into the catheter hub or when contacted by the valve actuator nose section.

A securing device can embody an eyelet having a flange and two or more leaf springs extending from the flange, and wherein the flange has an outside diameter and an inside diameter and wherein at least one cut-out can be made to the outside diameter and wherein the cut-out extends through two spaced apart points along the arc of the outside diameter.

A securing device can embody an eyelet having a flange and two or more leaf springs extending from the flange, and wherein the flange has an outside diameter and an inside diameter and wherein at least one cut-out can be made to the inside diameter and wherein the cut-out extends through two spaced apart points along the arc of the inside diameter. A leaf spring can be located between the two spaced apart points along the arc of the inside diameter.

A catheter assembly described herein can also be referred to as a needle device or an over-the-needle catheter assembly. The device or assembly can have a catheter hub with a catheter tube, a needle hub with a needle attached thereto and the needle projecting through the catheter hub and the lumen of the catheter tube.

A vent plug can be located at a proximal end of the needle hub. The plug can attach to the proximal opening of the needle hub.

A still yet further aspect of the invention is a catheter assembly comprising: a catheter tube having a lumen, a distal end opening, and a proximal end attached to a distal end of a catheter hub, said catheter hub comprising a catheter body with an exterior surface and an interior surface defining an interior cavity having at least one shoulder. A needle having a needle tip at a distal end and having a proximal end attached to a needle hub; said needle can project through the catheter hub and through the catheter tube and having the needle tip projecting distally of the distal end opening in a ready to use position. A valve having a valve disc located in the interior cavity of the catheter hub, the valve disc can comprise at least one slit and at least two flaps, a proximally facing surface, and a distally facing surface, and wherein said distally facing surface is in contact with the at least one shoulder. A skirt section can extend from the valve disc, the skirt section comprising a wall with an exterior surface and an interior surface defining a skirt interior and a skirt proximal end surface, said skirt section can be contact with the interior surface of the catheter hub. Alternatively, a securing device can be located proximally of the valve disc, the securing device can comprise a metallic ring body comprising a fluid path, a distal end, a proximal end, and at least one leaf spring having a free end extending proximally inward of the proximal end, the securing device securing the valve from proximal displacement. A valve actuator can be located in the interior cavity of the catheter hub, the valve actuator can have a nose section at a distal end and a proximal section proximally of the nose section; the nose section comprising a bore for fluid flow and an actuation end at a distal most end of the nose section. The proximal section can have at least one gap for fluid flow therethrough or thereacross. The valve actuator can be located in a proximal position within the interior cavity and slidable to a distal position within the interior cavity when pushed by a medical implement. Wherein when the skirt section is present, the nose section is located at least in part inside the skirt interior in the ready to use position; or wherein when the securing device is present, the nose section can be located inward of the metallic ring body in the ready to use position; and wherein when the skirt section is present, two spaced apart abutting surfaces are located proximally of the actuation end of the valve opener and proximally of the skirt proximal end surface in the ready to use position, the abutting surfaces are sized and shaped to abut the skirt proximal end surface when said valve actuator is in the distal position or, when the securing device is present, the at least one leaf spring is spaced from the nose section and biasing against the nose section when the valve actuator is in the distal position.

A needle guard can have a protective surface located to a side of the needle in the ready to use position and transitional to a position distal of the needle tip in a protective position to cover the needle tip from inadvertent needlestick.

The skirt section can comprise a ramp-shape cross-section and wherein said skirt proximal end surface can be located at a proximal end of the ramp-shape cross-section.

The nose section of the valve actuator can have a first slope extending into a transition section and wherein the transition section can have a second slope and wherein the second slope and the first slope can have different slope values.

The valve disc can have a first portion with a first thickness and a second portion with a second thickness and wherein the first thickness can be greater than the second thickness.

The at least one slit can be formed through the second portion of the valve.

The at least one stabilizing element can comprise a first end connected to a first plunger element of the valve actuator and a second end connected to a second plunger element of the valve actuator, said stabilizing element further can comprise a distal edge and a proximal edge.

The distal end can have a taper edge. The taper edge can originate closer to the exterior surface than the interior surface.

The needle guard can comprise a proximal wall comprising a perimeter defining an opening and at least one arm extending distally of the proximal wall, said at least one arm comprising an elongated arm portion, a distal wall, and an elbow located between elongated arm portion and the distal wall, and wherein a single bend can be located between the elongated arm portion and the distal wall to define a smooth or flat profile at the elbow where the needle guard contacts the distal edge.

The catheter hub can comprise a side port having an elongated body with a bore, said elongated body can extend at an angle to the catheter body. A tubing can connect to the side port at a first end of the tubing. A fluid connector can connect to a second end of the tubing. The fluid connector can be a needleless valve.

A grip paddle having a body can extend laterally of an axis defined by the needle.

The distal edge of the stabilizing element can comprise a taper edge that originates closer to an exterior surface of the stabilizing element and slants toward an inner surface of the stabilizing element.

The needle guard with a single bend or single change in direction on one or both arms of the needle guard can be particularly useful with a valve opener having a stabilizing element. The needle guard with a single bend or single change in direction on one or both arms of the needle guard can be particularly useful with a valve opener having a stabilizing element with a distal edge that has a taper edge. The taper edge and the single bend or change in direction can minimize catch point or snag point between the needle guard and the valve opener during retraction of the needle guard following successful venipuncture.

The invention further includes a method of manufacturing a catheter assembly. The method can comprise: attaching a catheter tube having a lumen, a distal end opening, and a proximal end to a distal end of a catheter hub, said catheter hub comprising a catheter body with an exterior surface and an interior surface defining an interior cavity having at least one shoulder. The method can further include attaching a needle having a needle tip at a distal end and having a proximal end to a needle hub; said needle projecting through the catheter hub and through the catheter tube and having the needle tip projecting distally of the distal end opening in a ready to use position. The method can further include placing a valve having a valve disc in the interior cavity of the catheter hub, the valve disc comprising at least one slit and at least two flaps, a proximally facing surface, and a distally facing surface, wherein said distally facing surface contacting the at least one shoulder. The method can further include extending a skirt section from the valve disc, the skirt section comprising a wall with an exterior surface and an interior surface defining a skirt interior and a skirt proximal end surface, said skirt section being in contact with the interior surface of the catheter hub; or placing a securing device in the interior cavity of the catheter hub and proximally of the valve disc, the securing device comprising a metallic ring body comprising a fluid path, a distal end, a proximal end, and at least one leaf spring having a free end extending proximally inward of the proximal end, the securing device securing the valve from proximal displacement. The method can further include placing a valve actuator in the interior cavity of the catheter hub, said valve actuator having a nose section at a distal end and a proximal section proximally of the nose section; the nose section comprising a bore for fluid flow and an actuation end at a distal most end of the nose section and the proximal section having at least one gap for fluid flow therethrough or thereacross, the valve actuator having a proximal position within the interior cavity and slidable to a distal position within the interior cavity when pushed by a medical implement, wherein: when the skirt section is present, the nose section is located at least in part inside the skirt interior in the ready to use position; or when the securing device is present, the nose section is located inward of the metallic ring body in the ready to use position; and wherein when the skirt section is present, two spaced apart abutting surfaces are located proximally of the actuation end of the valve opener and proximally of the skirt proximal end surface in the ready to use position, the abutting surfaces are sized and shaped to abut the skirt proximal end surface when said valve actuator is in the distal position or, when the securing device is present, the at least one leaf spring is spaced from the nose section and biasing against the nose section when the valve actuator is in the distal position.

A needle bevel at the needle tip can project distally of the distal opening or catheter tube opening of the catheter tube in the ready to use position. The ready position can be the position which the assembly or device can be used to perform an injection or puncture. The needle hub can be coupled to the catheter hub at the proximal opening of the catheter hub, which can have a female threaded Luer or Luer slip.

The catheter hub may incorporate a push tab and one or more surface features, such as ribs for pushing the catheter into the vein of a patient and over the needle. The needle hub can similarly incorporate surface features for a more secure grip when puncturing the vein and pulling out the needle from the catheter. Unless otherwise indicated, the various components of the catheter device or assembly may be made from conventional materials using conventional techniques.

In an example, a pair of wings can be incorporated with the body of the catheter hub and each wing can extend laterally of the lengthwise axis of the catheter hub in opposite directions at the bottom of the catheter hub. The pair of wings can be used by a practitioner to secure the catheter hub to the patient after successful venipuncture, such as with an adhesive tape or adhesive dressing.

A valve and a valve opener can be incorporated with the catheter hub to control fluid flow through the catheter hub, such as to control infusion or aspiration through the catheter hub. A needle guard or tip protector, which can have a surface or a wall for preventing inadvertent contact with the needle tip when the needle is removed from the catheter tube and the catheter hub following successful venipuncture, can be incorporated with the catheter device or assembly.

The needle guard or tip protector can embody a structure with one or more components for preventing inadvertent contact with the needle tip. For example, the needle guard can have a structure or a wall that moves from a position to the side of the needle shaft and proximal of the needle tip to a position distal of the needle tip to cover or block the needle tip from inadvertent contact. In an example, the needle guard can be one of the types described in U.S. Pat. No. 10,166,370.

The catheter hub has a body with an exterior surface and an interior surface defining the interior cavity. One or more shoulders or lips may be incorporated in the interior of the hub and can be used for seating the valve opener, the valve, and/or the needle guard in the ready to use position. The needle guard can be placed into the interior of the catheter hub by a nose section of the needle hub, which can project into the proximal opening of the catheter hub.

The needle assembly or catheter assembly may be provided with a catheter hub comprising an interior having a valve, a valve opener, and a needle guard located therein in the ready to use position. In an example, the needle guard is optional and can be omitted. In still other examples, the needle guard can be located substantially externally of the catheter hub. For example, a finger or a portion of a finger of the needle guard can be located inside the catheter hub while the remaining structure of the needle guard can be located externally of the catheter hub.

The catheter device or assembly of the invention can include a device or structure for securing or retaining the valve inside the catheter hub, which can be referred to generically as a securing device, a securing ring, or a securing element. The securing device, ring or element can have a structure that embodies a retainer, a retention ring, a retaining skirt, an O-ring of various possible cross sections, such as round, oval, square, rectangular, or a canted coil spring, among others.

The securing device can be separately formed from the valve or be made part of the valve, such as being used with the valve, being integrated with the valve, or being unitarily formed with the valve. Unless the context indicates otherwise, the term securing device can mean any of the noted structures and their equivalents for securing a valve inside a catheter hub and that can optionally include features for cooperating with or that generates force vectors to return a valve opener from a distal position to a proximal position. In an example, the securing device is located in line with the valve, with the valve opener, and with the needle guard.

In a particular example, the securing device has a bore or opening for receiving the needle and is in contact with both the valve and the interior of the catheter hub for limiting proximal movement of the valve inside the interior, for assisting in returning the valve opener from a distal position to a proximal position, or for both purposes, as further discussed below. The valve opener or part of the valve opener can be located inside the bore of the securing device in both the ready position of the catheter assembly and in the used position, such as following successful venipuncture, as further discussed below.

The needle guard can comprise a metallic body having a springing or resilient characteristic, a proximal wall, and at least one arm, or two arms, extending distally of the proximal wall. A change in profile can form on the needle shaft, proximal of and near to the needle tip and can engage a perimeter defining an opening on the proximal wall to limit distal movement of the needle guard off of the needle but allows the tip to enter the needle guard. The change in profile can comprise a crimp, a material buildup, a sleeve or any other increase in diameter, which will be larger than the opening in the proximal wall.

A valve, a valve opener or valve actuator, a securing device, and a needle guard can be configured, such as being sized and shaped, to be accommodated in an interior of a catheter hub, which can have a one-piece hub body, such as a unitarily formed single hub body, with a proximal opening having a female Luer and a distal end having a catheter tube extending therefrom. The open proximal end can optionally include exterior threads or lugs. In other examples, the catheter hub can be made from a multi-part hub body. For example, the catheter hub can have a first hub body attached to a second hub body, such as by bonding or welding, to form the body of the catheter hub.

In an example, the valve actuator can comprise a nose section at the distal end of the actuator body. The nose section can be elongated in structure and can be generally cylindrical or have a draft angle or taper that terminates in an actuation end for pushing into the valve to open the slits of the valve, as further discussed below. The actuation end of the nose section can have a blunt distal end surface or has a sharp edge. A flow passage can extend through the nose section for fluid flow. The nose section can have a wall surface with a continuous circumference or a continuous perimeter section defining a lumen or flow passage. The wall of the nose section can be without a gap or a slit, such as a cylinder with a continuous wall. The nose section can define a bore.

The wall at the nose section can be continuous. However, one or more through holes can be incorporated at the nose section for fluid flow therethrough or thereacross, such as for flushing. The bore of the nose section can have a constant bore diameter or can vary with the taper of the nose section. In some examples, a plurality of spaced apart slits and/or openings can be provided on the nose section, such as through the wall of the nose section, to permit flow or fluid flushing.

Two actuating elements or plunger elements can extend proximally of the nose section. For example, the two plunger elements can be unitarily formed with the nose section and can extend from the nose section in the proximal direction. A gap or space can be provided between the two plunger elements, which can define a holding space.

A needle guard or tip protector can be located in the holding space, or between the two plunger elements. In an example, the two plunger elements can each comprise at least two lengthwise edges and the edges can be spaced from one another. The lengthwise edges of the plunger elements can align with a lengthwise axis of the valve opener. A gap or space can be provided between the two plunger elements to function as a flow channel for fluid to flow therethrough or thereacross when fluid is passed through the catheter hub.

In other examples, there can be more than one gap or flow channel formed with the valve opener for fluid flow. In still other examples, the two plunger elements can be connected together by two bridges so that the proximal end of the valve opener is a continuous wall structure, formed by part of the two plunger elements and the two bridges. In some examples, a single plunger element is used with the valve opener.

In an example, a projection can extend outwardly from an outer surface of one or both plunger elements. A projection can extend from the outer surface of each plunger element. Each projection can resemble a tab having a generally flat edge for abutting a shoulder or lip formed in the interior of the catheter hub. The tab surface of the projection and the direction of the projection can allow the valve actuator to be inserted into the interior of the catheter hub and be seated within the catheter hub, as further discussed below. The projections can be sized and shaped to abut or contact a shoulder inside the catheter hub to limit proximal movement of the valve opener or actuator.

In an example, a transition section extends from the nose section and widens as the body of the valve opener extends axially in the proximal direction. The two actuating elements can extend from the transition section. The two actuating elements can alternatively extend from the nose section without a transition section. Some embodiments may utilize other shapes for the nose section, such as a cuboid, a rectangular, a conical, a pyramidal, a chamfered shape or the like.

In an example, the valve actuator or valve opener has a lengthwise axis, the one or more actuating elements extend axially or parallel to the lengthwise axis. In a particular example, two actuating elements are diametrically opposed to one another along the lengthwise axis. In other examples, the two actuating elements can diverge from one another as they extend in the proximal direction. In still other examples, the two actuating elements can converge towards one another as they extend in the proximal direction.

The spacing between the two plunger elements, whether straight, convergent, or divergent, can define the holding space between them. As shown, the two actuating elements define an outer diameter having a dimension that is larger than the diameter of the nose section. For example, the diameter defined by the two actuator elements at the proximal end can be larger than the diameter defined by any part of the nose section, excluding the projections. In some examples, the diameter defined by the two actuator elements is only larger than the actuating end at the nose section.

In some examples, the nose section of the valve actuator is provided with a shaped contour, such as with distinct lines or curves by forming recesses at the nose section with distinct contour lines or curves. One or more surfaces of the contoured nose section can then be used to press against the valve and the valve recoiling to push the contoured nose section in the proximal direction to return the valve actuator to a proximal position.

In some examples, the valve actuator or opener is made from a rigid material, such as plastic or metal, and the nose section of the valve actuator incorporates a more flexible section, which is understood to also be more pliable than the remaining portion of the valve actuator. For example, the flexible section can be a strip or a band of softer material than the base material used to make the valve actuator. The flexible section can be added to the valve actuator, like an elastomeric band, or molded with the valve actuator. The flexible section, which is pliable, can assist to return the valve actuator from a distal position to a proximal position.

In an example, the actuating elements are flexible and deflectable so that when pushed by a male Luer tip, such as a syringe tip or a male Luer tip adaptor, the actuator elements can defect or flex. The actuating elements can be deflectable by selecting a material that has the requisite resilient properties. In other examples, the actuating elements can be deflectable by incorporating one or more weakened sections, such as by incorporating a structurally thin section, by incorporating cut-outs, by employing a small cross-section compared to other sections of the same elongated actuating element, or combinations thereof. Alternatively, the actuating elements can be flexible and deflectable by selecting a material that has the requisite resilient properties and by incorporating one or more weakened sections.

In still other examples, each actuating element has more than one different cross-sectional profiles or contour along a length section. For example, an elongated plunger element can have a square profile located adjacent a crescent-shaped profile.

In an example, the actuating elements are rigid and not deflectable or deformable when loaded, such as when pushed, by a male Luer tip. Further, one or more stabilizing elements may be incorporated to increase the rigidity of the two actuating elements. The two actuator elements may each include a cross-sectional profile, at least at a proximal end, that overlaps a push end of a male tip so that the male tip can push the valve actuator into the valve, as further discussed below. The stabilizing elements can have proximal edges that are located distally of the proximal edges of the actuator elements or be flush with the proximal edges of the actuator elements.

The nose section of the valve actuator can be configured to engage the valve to open the valve flaps and the slits formed therebetween when an axial force is applied by a male tip to the actuator elements to move the valve actuator into the valve to deflect the valve flaps, such as during insertion of an male Luer connector of an IV drip line or administration set.

Generally, the nose section of the valve opener is rigid relative to the more pliable valve, which allows the nose section, and more specifically the actuation end of the nose section, to actuate the valve, such as to deflect the one or more flaps and open the one or more slits on the valve. The nose section may be made of a non-compressible material, such as from a metal material, a rigid plastic, or a hard elastomer for pushing against and opening the valve. However, the nose section can further include a more pliable section. For example, an elastomeric band, strip or section can be incorporated into or with the nose section.

A pair of opposed bands or stabilizers connecting the two actuating elements at a location along the length of the actuating elements that are between the nose section and the proximal end of the actuating elements can be incorporated. In some examples, the stabilizers can be located at the proximal end of the two actuating elements so that proximal edges of the stabilizers are generally flush with the proximal end surfaces of the actuating elements. The two stabilizer elements or bands can be referred to as a first or upper stabilizer element and a second or lower stabilizer element, elevation-wise.

In one embodiment, the stabilizers or stabilizer elements have wall surfaces that are arc-shaped, forming an arc that generally follows the interior profile of the catheter hub and connecting one actuating element to another actuating element. The stabilizers or stabilizer elements may form a substantially continuous cylindrical section on the body of the valve actuator, which body formed by the two stabilizer elements and the two actuating elements is spaced apart from the nose section of the valve actuator. In other words, the valve actuator can be elongated and can have sections that are continuous along a radial direction and sections with reliefs or through passages through the wall of the actuator that are not continuous along the radial direction.

In an example, the stabilizers define a continuous body section along a perimeter or radial direction of the valve actuator that is spaced from a continuous body section of the nose section, which is also continuous along a perimeter or radial direction. The two stabilizers or stabilizer elements, also referred to as bands, may be joined together with the two plunger elements to form a ring structure.

Optionally, the two stabilizers may be slightly offset and angled from each other in the axial direction, along the length of the valve actuator. In some embodiments, there may be one, three, or a different number of actuating elements or stabilizers. For example, there can be two actuating elements but only one stabilizer or band. In an example, the valve actuator, with the stabilizers or stabilizer elements and projections, is made from plastic, such as by plastic injection molding.

The stabilizers can help the valve actuator remain centered within the catheter hub while the actuator or actuator element moves, such as when pushed by a male Luer tip so that the nose section opens the slits of the valve. By staying centered, the nose section can be better aligned with the valve disc, such as with the slits on the valve disc, allowing for smooth actuation of the valve. The stabilizers can also provide an engagement, via friction, with the interior of the catheter hub to prevent the actuator from sliding in the proximal direction following removal of the male Luer tip. However, as discussed above, projections can be incorporated with the valve actuator for cooperating with an internal shoulder or lip inside the catheter hub to retain the valve actuator inside the catheter hub.

In one embodiment, the nose section is configured to remain engaged to the valve disc following actuation of the valve and following removal of the male Luer tip. For example, the nose section can wedge between the one or more slits on the valve disc and be held there by friction. Surface features, such as bumps, grooves, or barbs, can be provided on the valve actuator, such as on the nose section, to maintain the engagement between the actuator and the valve following actuation and following removal of the male Luer tip.

Preferably, the valve actuator does not engage the valve following removal of the male Luer tip. Preferably the valve actuator can move from a distal position pushed against the valve to a proximal position spaced from or only minimally touching the valve but permitting the valve flaps to return or to close up the slits.

When the valve opener returns to a proximal position after removal of the male Luer tip, the valve can close to prevent or limit fluid flow across the valve. The valve can open again by displacing the valve opener in the distal direction with a male medical implement, such as a syringe tip or a tip of an administration set. Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least two actuation cycles, at least three actuation cycles, at least four actuation cycles, at least five actuation cycles, or more. Each actuation cycle can comprise movement of the valve actuator into the valve, or a distal position, to deflect the valve flaps and movement of the valve actuator away from the valve, or proximal position.

At least one relief, opening, or through passage can be provided between a transition section of the valve actuator and the proximal end of the valve actuator. The transition section can be understood as the section proximal of the actuating distal end, or from the nose section until the two stabilizers. In an example, two reliefs or through passages are incorporated to provide clearance so that the interior or central part of the valve actuator and the interior surface of the catheter hub can be in open communication. In other words, between the continuous section of the nose section and the continuous perimeter section defined by the two stabilizers and the plunger elements, call a stabilizing ring, are one or two reliefs, through passages, or openings for fluid flow such as flushing. The through openings or reliefs can also be utilized to retain a needle guard, as further discussed below and if incorporated.

The stabilizing ring of the valve actuator can have an inside diameter that is smaller than the diameter defined by the diagonal section or elbows of the two arms of the needle guard when the two arms are biased outwardly by the side of the needle shaft in the ready to use position. Thus, during installation of the needle guard into the holding space of the valve actuator, the diagonal section or elbows of needle guard can deflect to pass through the stabilizing ring and into the open areas defined by the reliefs or through openings.

When the tip protector is positioned between the two plunger elements, the two distal walls of the needle guard, more specifically the two diagonal sections or elbows of the needle guard, can be located in the reliefs to engage the guard engagement surface on the interior surface of the catheter hub. This allows the needle guard to project from the holding space of the valve actuator through the two reliefs to engage with the guard engagement surface of the catheter hub. The needle guard can therefore be retained within the interior of the catheter hub in the ready to use position and during retraction of the needle following successful venipuncture until the needle tip moves proximal of the two distal walls on the needle guard, at which time the needle guard can close over the needle tip, the distal end of the needle guard becoming smaller in diameter than the inside diameter of the valve opener at the stabilizing rings and be removed with the needle.

An undercut or recessed section can be provided in the interior cavity of the catheter hub for accommodating the two diagonal sections or elbows of the needle guard. The needle guard can therefore be prevented from sliding in the proximal direction during retraction of the needle following successful venipuncture by a shoulder of the recessed section or by some other surface feature on the interior of the catheter hub, such as a guard engagement surface on the interior of the catheter hub. Optionally or alternatively, the distal edge of one or both stabilizers can provide the restraining surface to prevent the needle guard from early activation during retraction of the needle, prior to the needle tip moving proximally of the two distal walls of the needle guard. In addition to a distal edge, each stabilizer can have a proximal edge.

When the needle guard is retained by one or both distal edges of the stabilizers, the interior surface of the catheter hub can omit engagement feature or features for accommodating the elbows of the needle guard. In an example, the needle guard can engage with one or both distal edges of the two stabilizers and can engage with engagement feature or features formed inside the catheter hub, such as a groove, lip or shoulder.

In some examples, one or both stabilizer elements can have a slit or a channel, thus dividing the arc-shaped stabilizing or stabilizer element into two segments. Even with a slit on one or both stabilizer elements, the stabilizing ring, which can be a non-continuous ring, similar to a ring with one or more slots formed through the ring, can still provide the retaining structure to interact with the two elbows to prevent the needle guard from early activation during retraction of the needle, prior to the needle tip moving proximally of the two distal walls.

The retaining surfaces of the stabilizer elements, such as the distal edges, can be referred to as a restrict point, choke gap, or choke point since they provide a rigid structure that prevents the needle guard from moving proximally thereof unless or until the needle guard first activates and collapses radially to reduce its radial profile to then slip proximally of the choke point. In an example, one or two elbows of the needle guard can be restricted by the choke point from moving in the proximal direction until the one or two elbows of the needle guard deflect to reduce the needle guard's radial profile. In an example, when the radial profile of the needle guard is reduced, the needle guard can slip through the bore defined by the stabilizing ring, from a distal position of the stabilizing ring to a proximal position of the stabilizing ring.

The valve opener can be made from a metal material or from a plastic material. When made from a metal material, the valve opener can be formed by bending or deep draw methods and the arc shape cross section of the actuating element can provide added rigidity when pushed by the male Luer. Each actuating element can comprise at least two lengthwise edges and a rib can be provided along one or both of the lengthwise edges to further add structural rigidity. One or more gaps can be provided between any two actuating elements. The gaps can provide clearance or space for fluid flow flowing thereacross, such as during flushing blood or IV infusion. The gap between the actuating elements can define a holding space to accommodate a tip protector.

In some embodiments, a majority or most if not all of the tip protector fits within a holding space formed by the body of the actuator, between the two plunger elements, in the ready to use position, as further discussed below. This configuration allows the catheter hub to be more compact, as less longitudinal space is needed within the hub to fit both the valve actuator and the tip protector serially lengthwise or when the two only partially overlap in the axial direction.

Aspects of the invention, including use of the noted securing device and various other components, can be used with or on commercially available needle gauges, such as from 24 gauge to 14 gauge needles.

When the tip protector only engages with the distal edge of the relief or through passage in the actuator, then no deformity or change of diameter is required on the inside wall of the catheter hub and the tip protector can be placed further proximally in the female Luer taper section while complying with the international Luer standard for conical fittings and the overall length of the catheter hub can be further reduced.

A valve usable with the present invention can have a first portion having a first thickness and a second portion having a second thickness less than the first thickness, measured orthogonal to a medial plane passing through the diameter of the valve. The second portion with the second thickness can have a substantially constant thickness but can optionally include varying thicknesses along a cross-section of the valve, at the second portion.

In an example, the second portion is formed by recessing the distally facing surface of the valve, the proximally facing surface of the valve, or both surfaces while the first portion retain substantially the full width or thickness of the valve between the proximally and distally facing surfaces. In an example, the recesses at the second portion can embody undercuts formed into the valve.

The surface appearance between the first and second portions can resemble a three-leaf clover. The three-leaf clover can be present on the distally facing surface, the proximally facing surface, or both surfaces of the valve. In other examples, the surface appearance of the proximally and/or distally facing surfaces can have varying contours so that the three-leaf clover can have contours of varying curves, lines, and edges.

In an example, slits are formed through the thinner second portion of the valve to form valve flaps between adjacent valves slits. In some examples, there can be two or more slits forming one or more valve flaps. For example, the first and second portions of the valve can define a four-leaf clover, which can have four slits and four valve flaps. Preferably, the valve can have three slits and three valve flaps. The slits can start from approximately a central location of the valve and extend radially outwardly towards but short of the outer perimeter of the valve. The length of each slit can vary to form valve flaps of different sizes. The lengths of the slits can be selected to provide the desired valve flaps and valve flap deflection when pushed by a nose section of a valve opener, such as when pushed by the actuation distal end of the valve opener.

The valve may be integrally formed from a single material. Alternatively, the valve may be formed of different materials in various portions of the valve for reasons such as improved rigidity or flexibility. The valve can be made from a medical grade elastomer or a thermoplastic elastomer (TPE). Aspects of the valve can be made in accordance to the valve examples disclosed in PCT Appl. No. PCT/EP2017/070934, published as PCT Pub. No. WO2018/033626 A1, the contents of which are expressly incorporated herein by reference as if set forth in full.

The securing device can be a retention ring, which can have an annular wall structure having an exterior surface and an interior surface defining a bore. In some embodiments, the securing device for securing the valve inside the catheter hub can be a retaining skirt, O-ring or a spring. The valve, the valve opener or valve actuator, and the securing device can vary in shapes, styles, and features but otherwise perform the noted functions described herein.

The valve can be a valve disc as described having at least one slit defining at least two flaps. The valve disc can have three or more slits, or split disc valve portion, defining three or more flaps and the surface of the disc can have varying surface features and thicknesses along a cross-section of the valve disc. In other examples, the valve can have a valve disc and a skirt extending proximally of the proximally facing surface of the valve disc.

A catheter hub provided herein can have a valve, a valve opener, a securing device, and a needle guard located inside the interior cavity of the hub body, which can be a single hub body with a distal end having a catheter tube extending therefrom and a proximal opening with a female Luer. The valve can be located distally of the securing device, part of the valve opener can be located in the bore of the securing device, and the needle guard can be located in the holding space of the valve opener. In other examples, the needle guard can be omitted or can be located outside of the holding space, such as in a housing that is different or separable from the catheter hub.

In an example, the interior of the catheter hub is provided with one or more shoulders or ledges, which can be understood as a structural lip or stop formed on the wall of the interior surface. The one or more shoulders can provide engagement points or stop points for the components placed inside the interior cavity, to prevent the components from moving or dislodging from the interior of the catheter hub. As shown, the valve can be placed in an annular groove and can abut one of the shoulders to prevent proximal displacement of the valve. The valve can also abut a shoulder of the catheter hub on the distal side of the valve to prevent distal displacement of the outer perimeter of the valve.

A securing device or retention ring in the form of an annular ring can be positioned adjacent the valve and is abutted, at the securing device's proximal end, against another shoulder inside the interior cavity of the catheter hub to prevent or limit proximal displacement of the securing device.

In an example, the securing device has a cross-section having a ramp shape, triangle shape, or slanted surface with the high part of the ramp at a distal location and tapers as it extends in the proximal direction. The securing device may be made from a medical grade plastic material, such as by plastic injection. In other examples, the securing device may be made from a metal material, such as by stamping and then forging, pressing, or machining. In other examples, the securing device may be made from an elastomeric material, such as an O-ring, to provide a proximally directed force to the valve opener when compressed between the valve opener nose section and the inner wall of the catheter hub in the distal position. The O-ring can be deflected or deformed by the valve opener to generate stored energy to the O-ring, which can then apply a proximally directed force to the valve opener when the stored energy is released.

The distal end of the securing device, the high part of the ramp, can abut the proximally facing surface of the valve and the proximal end of the securing device, the narrow part of the ramp, can abut one of the shoulders of the interior cavity. This arrangement of the securing device can assist in holding the valve from proximal displacement inside the catheter hub. In some examples, the valve can be secured or supported inside the catheter hub by the securing device without also resorting to a separate shoulder abutting the proximal edge of the valve.

In an example, the securing device can have a slight interference when first entering the proximal open end of the catheter hub and can have a size-on-size fit or a slight interference fit with the catheter hub in the final seated position shown. In still other examples, the securing device can be retained within the interior of the catheter hub and can secure the valve from proximal displacement with only interference fit with the catheter hub without a separate shoulder abutting the proximal end of the securing device.

The securing device can be a retention ring having a generally triangular cross section. In other examples, the cross section can have a different shape, such as a complex shape.

In addition to securing the valve within the catheter hub, the retention ring, or securing device, can also function as a return mechanism for aiding the valve opener to return or move from a distal position to a proximal position. For example, when the valve opener is advanced by a male Luer tip to open the slits of the valve, the retention ring can help to return the valve opener to a proximal position after removal of the male Luer tip from the proximal opening of the catheter hub.

In some examples, the securing device only secures the valve from proximal movement while the elasticity of the valve returns the valve opener from a distal position to a proximal position after removal of a male Luer tip from the proximal opening of the catheter hub.

In some examples, the cross-section of the securing device can be chosen to be other than triangular in shape. In other examples, the shaped cross-section of the retention ring can be formed as a retention skirt and be part of the valve. For example, the valve can be formed with both the valve disc and the retention skirt, such as by integrating or unitarily forming.

In the example shown, the length of the valve opener is selected so that the actuation end or actuating end at the distal end of the nose section just touches the valve disc of the valve and the proximal end edges of the two plunger elements just touch the nose section of the needle hub in a ready to use position. In other examples, the actuating end can be slightly spaced away from the valve disc or slightly pressed against the valve disc but not materially deflect the valve flaps in order to allow the valve flaps to close the valve slits.

In an example, the holding space of the valve opener can be sized and shaped to accommodate a needle guard. The needle guard can be located between the two plunger elements of the valve opener. The needle guard, which can have a proximal wall and two arms located distally of the proximal wall, can be located in the holding space of the valve opener with two elbows of the needle guard located distally of the two stabilizing elements. Thus, if the needle is retracted in the proximal direction, the two elbows will be stopped from moving proximally past the two distal edges of the two stabilizing elements, which can act as a choke point.

The radial dimension of the needle guard at the two elbows can be larger than the inside dimension of the stabilizing ring and therefore can be physically stopped by the distal edges of the two stabilizer elements. Following successful venipuncture, the needle can be removed from the catheter tube and the catheter hub and the needle tip moves proximally of the two distal walls of the needle guard, which then allows the two arms of the needle guard to move inwardly or collapse to decrease the radial dimension at the two elbows. Approximately at the same time, the change in profile near the needle tip can abut the perimeter defining the opening on the proximal wall of the needle guard and further retraction of the needle causes the needle guard to be removed with the needle.

In an example, the interior of the catheter hub can be enlarged at a location proximate the two elbows when the needle guard is located inside the catheter hub. For example, the inside diameter of the catheter hub at the two elbows can be larger than the inside diameter of the catheter hub at the proximal wall of the catheter hub. This space can be incorporated to provide relief or added space for the needle guard in the ready position. That is, the relief, when incorporated, provides space for the two arms so that the two arms are not compressed or biased inwardly at the two elbows in the ready to use position to the same extent compared to when no relief is provided. This can reduce drag between the needle shaft and the two curved ends at the ends of the two distal walls during retraction of the needle following needle puncture.

The valve opener can be retained in the interior cavity of the catheter hub and restricted from displacing out of the proximal opening by providing at least one side projection on the valve opener to interact with one of the shoulders inside the interior cavity. The cross-sectional dimension of the valve opener at the at least one projection can be larger than the cross-sectional dimension at the shoulder of the catheter hub, thereby presenting a physical stop to prevent proximal displacement of the valve opener out of the proximal opening of the catheter hub.

If the valve opener moves in the proximal direction, such as due to the elbows of the needle guard pushing in the proximal direction against the distal edges of the two stabilizing elements during retraction of the needle but before the needle tip moves proximally of the two distal walls, the total proximal movement can be restricted by the projection hitting against one of the shoulders in the catheter hub. In an example, two projections can be provided on the valve opener, one on each actuating element, to interact with the shoulder, which can be annular in configuration.

Following removal of the needle, the plurality of valve flaps are permitted to recoil or return to a relaxed state to close or close in the slits and restrict flow in the proximal and distal directions through the valve. The actuating end at the nose section of the valve actuator can be located within the bore defined by the securing device, but spaced from or not contacting the securing device, prior to actuation. The tapered surface of the nose section can also be spaced from the securing device. This spacing or gap can allow the valve actuating element to move forward in the distal direction, when pushed by a male Luer tip, before hitting or contacting the securing device.

In some examples, the male Luer tip abuts the female Luer of the catheter hub to stop further distal advancement of the male Luer tip into the catheter hub before the nose section of the valve actuator contacts or presses against the inside of the securing device.

The actuating end of the valve actuator can be in contact with the proximally facing surface of the valve following removal of the needle. In other examples, the actuating end can be slightly spaced from the proximally facing surface of the valve following removal of the needle.

As shown, the nose section of the valve opener can have an increasing taper in the proximal direction, which can be spaced from the tapered surface of the ramp cross-section of the securing device. The size and shape of the nose section can be arranged to contact the ramp cross-section of the securing device or spaced from the ramp cross-section. Alternatively or in addition thereto, the size and shape of the securing device can be arranged to contact the nose section of the valve actuator when the valve actuator is advanced into the valve to deflect the valve flaps.

In an example, the nose section can incorporate a resilient section or band, such as an elastomeric band, strip, or strips, and can create a slight interference as the valve opener is advanced in the distal direction to open the valve and the nose section abutting the securing device.

If the lengthwise axis of the catheter hub is considered an X-axis and the Y-axis is orthogonal to the X-axis, the shape of the nose section can be selected to both deflect the valve flaps in the distal direction as well to generate force vectors that have both an X component and a Y component. The force vectors acting in the X direction, an X component force vector or proximally directed force vector, can be utilized to facilitate the return of the valve opener from a distal position, where the actuating end is pushed into the valve to deflect the valve flaps, to a proximal position as shown.

The valve flaps of the valve or both the valve flaps of the valve and the securing device can generate force vectors against the nose section of the valve opener to return the valve opener from a distal position to a proximal position. In still yet other examples, other part or parts of the valve, aside from the valve flaps, can exert a proximally directed force to move the valve from a distal position to a proximal position.

In an example, the area or section inside the catheter hub adjacent the open proximal end can be a female Luer, which is understood to have a structure formed in accordance with the ISO Standards for female Luers. The proximal edges of the two plunger element of the valve opener can be recessed from the proximal open end of the catheter hub but located within the female Luer. Thus, when a male Luer tip is inserted into the female Luer, the male Luer tip can push the two plunger elements in the distal direction to cause the valve opener to push into the valve to open the valve, such as to distally deflect the valve flaps and open the one or more slits.

A male Luer tip can be inserted into the open proximal end of the catheter hub and to advance the valve opener into the valve to open the valve flaps and open fluid communication between the male Luer tip and the lumen of the catheter tube. In practice, the male Luer tip can be a syringe tip or a male tip of an IV drip line or administration set that is attached to an IV bag.

Fluids can be withdrawn or aspirated out the catheter hub in the proximal direction or infused through the catheter tube in the distal direction. The male Luer tip can have a threaded collar for engaging the lugs or external threads on the catheter hub to further maintain the valve actuator in the distal position to open the valve.

In an example, the valve opener is configured to move distally when advanced by the male Luer tip. The amount or distance that the valve opener moves in the distal direction should be sufficient to allow the actuating end and the nose section to deflect the valve flaps in the distal direction to open the slits of the valve to then open fluid communication between the male Luer tip and the catheter tube. In the example shown, the actuating end of the valve opener moves distal of the valve flaps and the valve flaps are compressed between the interior of the catheter hub and the tapered surface of the nose section, or at least deflected distally by the nose section. The valve flaps can be deformed by the tapered surface of the nose section. In other examples, the actuating end moves a distance that is equal to the ends of the valve flaps or short of the ends of the valve flaps, never-the-less still opening the valve flaps to allow free flow in both proximal and distal directions.

Upon withdrawal of the male Luer tip, such as when replacing an IV fluid bag attached to the male Luer tip, the distally directed force acting on the proximal edges of the two plunger elements by the male Luer tip is removed or ceased and the female Luer is unoccupied by any external object. This allows for the valve opener to return to its proximal position, now vacated by the male Luer tip.

In an example, the elasticity of the valve allows the valve flaps to recoil to their more relaxed state. This recoiling action of the valve flaps and the shape of the nose section of the valve opener allow the valve flaps to impart force vectors on the nose section to cause the valve opener to move from the distal position to a proximal position.

The force vectors generated by each of the valve flaps on the nose section of the valve opener when the valve flaps recoil include a force component that is generally parallel to the lengthwise axis of the catheter hub, also referred to herein as the X-component force vector or proximally directed force vector. Thus, the X-component force vector generated by the valve flaps can cause the valve opener to move from a distal position, where the actuating end and the nose section deflect the valve flaps of the valve in the distal direction to open the valve, to a proximal position, where the actuating end and the nose section no longer deflect the valve flaps.

In some examples, the nose section of the valve actuator is provided with a shaped contour, such as with distinct lines or curves by forming recesses at the nose section with distinct contour lines or curves. One or more surfaces of the contoured nose section can then be used to press against the valve. The valve can be pressed to generate multiple compression points. For example, the contoured nose section can be structured to compress the valve flaps or deflect the valve flaps in the distal direction so that the valve flaps can in turn generate force vectors against the nose section as the male Luer tip is removed and the valve flaps allowed to return to their relaxed state.

The contoured nose section can also axially compress part or parts of the valve against a distal shoulder so that the valve imparts an opposite axially returning force when the male Luer tip is removed. The valve alone can therefore push the valve opener in the proximal direction upon removal of the male Luer tip when the valve recoils from being compressed by the contoured nose section alone or by multiple points sections of the contoured nose section.

In an example, the valve opener can deflect, deform, or bias the valve, such as deflect, deform, or bias the valve flaps and other part or parts of the valve, such as a skirt section extending from a valve disc. When the valve flaps and the other part or parts, such as the skirt section, return to their relaxed state or un-biased state, they impart proximally directed forces to the valve opener to move the valve opener from a distal position to a proximal position.

In some examples, the interference between the ramp cross-section of the securing device and the nose section produces force vectors on the nose section of the valve opener, which include an X-component force vector. For example, the valve opener can incorporate an elastic band or one or more elastic strips to be compressed, deformed, or biased by the securing device as the nose section is advanced by the male Luer tip into the securing device to impart stored energy. Thus, in addition to return forces generated by the valve flaps of the valve on the nose section of the valve opener, the interference between the securing device and the nose section of the valve opener generates a return force and contributes to the proximal movement of the valve opener from a distal position, where the actuating end and the nose section deflect the valve flaps of the valve in the distal direction, to a proximal position, where the actuating end and nose section no longer deflect the valve flaps.

In the proximal position, the valve opener is situated inside the catheter hub and the valve flaps generally closing off the slits so as to stop or restrict fluid flow in the proximal direction and/or the distal direction. In some examples, the nose section can be provided with a recess and an elastomeric strip or band is placed in the recess to create a valve opener with a rigid section and a more pliable section. In other examples, the nose section is co-molded or insert-molded with the elastomeric strip or band. The elastomeric strip or band incorporated with the nose section can allow the valve actuator to be pressed against a rigid part or component of the securing device to generate a return force following removal of the male Luer tip.

Aspects of the invention are therefore understood to include a catheter assembly or needle device comprising a catheter hub having a catheter tube extending in a distal direction, said catheter hub comprising a body having an exterior surface and an interior surface defining an interior cavity. A valve and a valve opener can be located inside the interior cavity. In an example, a securing device having a body defining a bore is located proximal of the valve. The valve flaps of the valve can impart a proximally directed return force to return the valve opener from a distal position to a proximal position.

Additionally or alternatively, a valve can be compressed, deformed, or biased axially against a distal shoulder and the valve providing an axially directed force against the nose section to return the valve opener, upon removal of the male Luer tip. In an example, the securing device can provide an interference with the valve opener, such as an elastomeric part of the valve opener, when the valve opener is advanced in the distal direction by a male Luer tip to open the valve flaps of the valve and wherein the interference can provide force vectors that include a force vector that extends generally parallel to the lengthwise axis of the catheter hub to return the valve opener from a distal position to a proximal position, when the male Luer tip is removed from the catheter hub.

The valve, such as the valve flaps or the skirt section of the valve can be deflected, biased, or deformed by a first structure, such as a valve opener, moving into the valve without requiring a second structure to be located opposite the first structure, although optionally the second structure can be incorporated. For example, the valve flaps can be deflected by the valve opener, without a shoulder or a rigid surface located on the opposite side of the valve flaps to stop the deflection. Other objects can be deflected, biased, or deformed without an opposing structure, such as a leaf spring being deflected, biased, or deformed by the nose section of a valve opener or a spring ring being expanded by insertion of a tapered section of the nose section.

In some examples, the nose section is spaced from the securing device or does not abut the securing device and the return force is provided by the valve only. The securing device can additionally provide a securing function for securing the valve inside the catheter hub and preventing the valve from inadvertent proximal displacement to dislodge from the catheter hub. The catheter hub can include a needle projecting through the catheter hub, the valve, the valve opener, the securing device and the catheter tube. The needle can attach to a needle hub at the needle's proximal end.

Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least two cycles, at least three cycles, at least four cycles, at least five cycles, or more.

In an example, an annular slit or annular channel can be provided on the proximally facing surface of the valve. The annular slit can be recessed from the outer perimeter of the valve. The annular slit can be provided at the first portion of the valve, which is the thicker part of the valve that is thicker than the second portion of the valve. The annular slit can be provided to receive a distal end of a securing device.

The securing device can be a retention ring having a distal end that projects into the annular slit. In an example, the distal end of the securing device can be forced into the annular slit and held therein by compression or interference. In other examples, the securing device could be held within the annular slit using adhesive or bonding. In still other examples, the annular slit is an annular channel and does not grip the securing device on both the interior and exterior surfaces of the securing device. For example, the exterior surface of the securing device can press against the annular channel but is spaced from the annular channel on the interior surface of the securing device. This alternative configuration allows the securing device to press the valve outwardly against the catheter hub without also requiring the annular slit to grip both interior and exterior surfaces of the distal end of the securing device.

The retention ring can have a wall with a length between the proximal and distal ends of the retention body and with a generally constant wall thickness curved body section at the proximal end of the retention ring. The wall can have an interior that defines a bore for accommodating the nose section of the valve opener and for allowing fluid flow, such as flushing.

The wall of the securing device can be generally cylindrical except for the proximal end. In an example, the proximal end of the retention ring can have an outwardly curved lip for securing the retention ring against an internal shoulder of the catheter hub. Once located against the internal shoulder, the securing device can help to secure the valve from displacing in the proximal direction. The valve can be secured or supported from distal movement by being located against a shoulder of the catheter hub on the distally facing surface of the valve.

The securing device and the nose section of the valve opener can be spaced from one another in the valve opener proximal position. The gap or spacing between the two provides clearance for the valve opener to move in the distal direction to open the valve, such as to deflect the valve flaps, before contacting or hitting the securing device. The actuating end at the nose section of the valve actuator can be located within the bore defined by the securing device, but spaced from or not contacting the securing device. The tapered surface of the nose section can also be spaced from the securing device. This spacing or gap allows the valve actuating element to move forward in the distal direction before hitting or contacting the securing device. The actuating end can contact with the proximally facing surface of the valve. In other examples, the actuating end can be slightly spaced from the proximally facing surface of the valve.

A male Luer tip can be inserted into the open proximal end and advancing the valve opener into the valve to open the valve flaps and open fluid communication between the male Luer tip and the lumen of the catheter tube. The male Luer tip can have a threaded collar for engaging the lugs or external threads on the catheter hub to further maintain the valve actuator in the distal position to open the valve.

In an example, the valve opener is configured to move distally when advanced by a male Luer tip. The amount or distance that the valve opener moves in the distal direction should be sufficient to allow the actuating end and the nose section to deflect the valve flaps in the distal direction to open the slits to then open fluid communication between the male Luer tip and the catheter tube. The actuating end of the valve opener can move distal of the valve flaps and the valve flaps can be compressed or deformed by the tapered surface of the nose section, or the valve flaps are at least deflected or deformed in the distal direction by the nose section of the valve opener. The actuating end can move a distance that is equal to the ends of the valve flaps or short of the ends of the valve flaps but still opening the valve sufficiently for free flow in both directions.

A curved lip on the securing device can act like a biasing member. Thus, when the nose section of a valve actuator or opener is pressed against the curved lip at the proximal end of the securing device, the curved lip presses against the nose section, such as against an elastomeric band, strip or section incorporated at the nose section, and imparts a pair of component forces or force vectors on the nose section of the valve opener, which includes a force that acts generally parallel to the lengthwise axis of the catheter hub. In other examples, the nose section is spaced from the securing device when the male Luer tip abuts the female Luer of the catheter hub. The valve under that scenario can provide the return force needed to return the valve opener from a distal position to a proximal position and the valve opener can omit the pliable section or sections at the nose section.

Upon withdrawal of the male Luer tip, such as when replacing an IV fluid bag attached to the male Luer tip, the distally directed force acting on the proximal edges of the two plunger elements by a male Luer tip is removed or ceased and the female Luer is unoccupied by an external object. This allows for the valve opener to return to its proximal position, now vacated by the male Luer tip.

In an example, the elasticity of the valve allows the valve flaps to recoil to their more relaxed state, such as to move to a proximal position. This recoiling action of the valve flaps and the shape of the nose section of the valve opener allow the valve flaps to impart force vectors on the nose section to cause the valve opener to move from a distal position to a proximal position.

Aspects of the invention is therefore understood to include a catheter assembly or needle device comprising a catheter hub having a catheter tube extending in a distal direction, said catheter hub comprising a body having an exterior surface and an interior surface defining an interior cavity. A valve and a valve opener can be located inside the interior cavity. In an example, a securing device having a body defining a bore is located proximal of the valve and secures the valve inside the catheter hub.

In an example, the securing device provides an interference with the valve opener when the valve opener is advanced in the distal direction by a male Luer tip. In another example, the male Luer tip abuts the female Luer of the catheter hub before the nose section of the valve opener contacts the securing device. The valve opener is configured to open the valve flaps of the valve.

In an example, the interference, deflection, bias or compression by the valve opener to the valve flaps provides force vectors that include a force vector that extends generally parallel to the lengthwise axis of the catheter hub to return the valve opener from a distal position to a proximal position, when the male Luer tip is removed from the catheter hub.

The securing device can also impart a return force to the nose section, such as to the area of the nose section with a pliable insert, elastic band or material, of the valve opener to provide an additional proximally directed return force. In some examples, the securing device can incorporate a structure with resilient characteristics to store energy when biased, deformed, or deflected by the valve opener and then release the stored energy to generate a proximally directed force to the valve opener to move the valve opener from a distal position to a proximal position.

As discussed herein, movement from a distal position to a proximal position, or vice-versa, requires physical measurable movement.

The securing device can additionally provide a securing function for securing the valve inside the catheter hub and preventing the valve from inadvertent proximal displacement to dislodge from the catheter hub. The catheter hub can include a needle projecting through the catheter hub, the valve, the valve opener, the securing device and the catheter tube. The needle can attach to a needle hub at the needle's proximal end.

Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least two actuation cycles, at least actuation three cycles, at least four actuation cycles, at least five actuation cycles, or more. Each actuation cycle can be defined as movement of the valve actuator into the valve to deflect the valve flaps and movement away from the valve.

In a further example, the securing device can be a retention ring having a distal end with an outward curved lip forming a flange for abutting or contacting the proximally facing surface of the valve and a wall or body that tapers from a first dimension to a second larger dimension in the proximal direction. Thus, the wall of the present embodiment can resemble a ramp with a high part of the ramp at a distal location and tapers as it extends in the proximal direction.

The proximal end of the securing device can comprise a proximal edge that can be dimensioned to abut or press against an internal shoulder of the catheter hub. Once located against the internal shoulder, the securing device can help to secure the valve from displacing in the proximal direction. Alternatively, there does not need to be a shoulder to secure the securing device within the interior if there is a slight interference fit between the proximal end, and/or distal end of the securing device, and the inside diameter of the catheter hub. The valve can be secured or supported from distal movement by being located against a shoulder on the distally facing surface of the valve.

The securing device and the nose section of the valve opener can be spaced from one another in the valve opener proximal position. The gap or spacing between the two provides clearance for the valve opener to move in the distal direction to open the valve, such as to deflect the valve flaps, before closing the gap, contacting or hitting the securing device.

In the valve actuator proximal position, the actuating end at the nose section of the valve actuator can be located within the bore defined by the securing device, but spaced from or not contacting the securing device. The tapered surface of the nose section can also be spaced from the securing device. This spacing or gap allows the valve actuating element to move forward in the distal direction before hitting or contacting the securing device. The actuating end of the valve actuator can be in contact with the proximally facing surface of the valve. In other examples, the actuating end can be slightly spaced from the proximally facing surface of the valve.

A male Luer tip can be inserted into the open proximal end and advancing the valve opener into the valve to open the valve flaps and open fluid communication between the male Luer tip and the lumen of the catheter tube.

In an example, the valve opener is configured to move distally when advanced by the male Luer tip. The amount or distance that the valve opener moves in the distal direction should be sufficient to allow the actuating end and the nose section to deflect the valve flaps in the distal direction to open the slits to then open fluid communication between the male Luer tip and the catheter tube. In an example, the actuating end of the valve opener moves distal of the valve flaps and the valve flaps are compressed or deformed between the interior of the catheter hub and the tapered surface of the nose section or the valve flaps are deflected in the distal direction by the nose section of the valve opener.

In some examples, the nose section of the valve actuator is provided with a shaped contour, such as with distinct lines or curves by forming recesses at the nose section with distinct contour lines or curves. One or more surfaces of the contoured nose section can then be used to press against the valve and the valve recoiling to push the contoured nose section in the proximal direction to return the valve actuator to a proximal position. For example, one or more of the contoured surfaces can axially compress, deform, or bias the valve against a distal shoulder to generate stored energy so that the valve provides an axially directed return force upon removal of the male Luer tip. In some examples, the actuating end moves a distance that is equal to the ends of the valve flaps or short of the ends of the valve flaps, but still opening the valve sufficiently for free flow in both directions.

In an example, a ramp of the securing device acts like a biasing member. For example, when the nose section is pushed against the ramp structure of the securing device by a male Luer tip, the securing device exerts an opposite biasing force against the nose section of the actuator, such as against a pliable section located at the nose section. Thus, when the nose section is pressed against the ramp in an interference, the ramp of the securing device imparts a pair of component forces or force vectors on the nose section, which includes a force that acts generally parallel to the lengthwise axis of the catheter hub. In some examples, the nose section is spaced from the securing device when the male Luer tip abuts the female Luer of the catheter hub.

Upon withdrawal of the male Luer tip, such as when replacing an IV fluid bag attached to the male Luer tip, the distally directed force acting on the proximal edges of the two plunger elements by the male Luer tip is removed or ceased and the female Luer is unoccupied by any external object. This allows for the valve opener to return to its proximal position, now vacated by the male Luer tip. In an example, the elasticity of the valve allows the valve flaps to recoil to their more relaxed state.

This recoiling action of the valve flaps and the shape of the nose section of the valve opener allow the valve flaps to impart force vectors on the nose section to cause the valve opener to move from a distal position to a proximal position. Additionally, the ramp structure of the securing device can exert a returning force against the nose section, such as to a pliable section located at the nose section, to move the valve opener in the proximal direction to return the valve opener to a proximal position.

Aspects of the invention is therefore understood to include a catheter assembly or needle device comprising a catheter hub having a catheter tube extending in a distal direction, a needle attached to a needle hub and the needle extending through the catheter hub and the catheter tube. The catheter hub comprising a body having an exterior surface and an interior surface defining an interior cavity.

A valve and a valve opener can be located inside the interior cavity. In an example, a securing device having a body defining a bore is located proximal of the valve and secures the valve in the catheter hub. The securing device can provide an interference with the valve opener when the valve opener is advanced in the distal direction by a male Luer tip to open the valve flaps of the valve and wherein the interference fit provides force vectors that include a vector that extends generally parallel to the lengthwise axis of the catheter hub to return the valve opener from a distal position to a proximal position, when the male Luer tip is removed from the catheter hub.

The securing device can additionally provide a securing function for securing the valve inside the catheter hub and preventing the valve from inadvertent proximal displacement to dislodge from the catheter hub and not provide any return force to the valve opener.

In an example, a retention ring has a ring body with a first end or distal end and a second end or proximal end. The ring body can have a generally constant outside dimension along the length of the ring body, which can be generally cylindrical. Internally, the ring body can have a smaller inside diameter at the distal end than the inside diameter at the proximal end and a wall thickness that decreases in dimension from a distal end to a proximal end.

The inside surface of the ring body can define a bore and wherein the bore is configured to accommodate a valve opener. Fluid flow can flow through the bore. The bore of the securing device can compress or bias the nose section of the valve opener to impart a pair of component forces, as previously discussed. In another example, the securing device is sized and shaped to be spaced from the nose section when the male Luer tip abuts the female Luer of the catheter hub. In an example, the securing device is formed from a medical grade plastic material. In other examples, the securing device can be formed from a medical grade elastomeric material or a thermoplastic elastomer material (TPE). The securing device may alternatively be made from a metal material, such as by stamping and bending or machining.

The cross-section of the ring body can have a ramp shape or a slanted surface on the interior surface of the ring body. Further, the slanted surface can have a constant slope. In other examples, the slope of the slanted surface is not constant. For example, there can be one or more bumps or inflection points to produce a contour that is not straight. The contour, whether with a constant slope or not, can be selected to generate a compression, bias or interference with the nose section of a valve opener, such as to pliable section or sections of the nose section, when the valve opener is pushed against the securing device. The compression, bias or interference fit with the valve opener can be configured to generate force vectors, which include a force that is generally parallel to the lengthwise axis of the valve opener. This in turn helps the valve opener to move from a distal position to a proximal position.

In an example, the proximally facing surface of a valve provided herein can have an annular slit or annular slot for receiving the distal end of the securing device. In some example, the annular slot can be an annular channel with a gap that does not grip both interior and exterior surfaces of the distal end of the securing device. The securing device can be made from a thin-walled cylinder, such as from a metal material or from a plastic material, and wherein the proximal end can be curved outwardly to terminate in a curved lip, similar to a radiused corner.

The inside surface of the ring body of the securing device can define a bore and wherein the bore is configured to accommodate a valve opener and compress or bias the nose section of the valve opener, such as to pliable section or sections of the nose section, to impart a pair of component forces, as previously discussed. The radiused corner of the curved lip can be configured to compress the nose section of the actuator and impart a pair of component forces. In another example, the securing device is sized and shaped to be spaced from the nose section when the male Luer tip abuts the female Luer of the catheter hub.

The curved lip of the securing device can have an outside diameter and wherein the outside diameter of the curved lip is smaller than the outside diameter of the valve. Depending upon the structure of the interior of the catheter hub, the size of the curved lip can be adjusted so that when installed inside the catheter hub, the curved lip abuts or contacts a shoulder inside the catheter hub to secure the retaining ring within the interior cavity of the catheter hub.

In an example, the ring body of a securing device has a distal end with a curved lip defining a flange, which has a generally planar wall surface for abutting a surface of a valve, such as abutting a proximally facing surface of the valve. The ring body of the securing device can have a generally constant wall thickness that tapers outwardly from a first diameter at the distal end, just proximal of the flange, to a second larger diameter at the proximal end, which has a proximal edge for abutting or contacting a shoulder inside a catheter hub to retain the securing device within the catheter hub.

The wall surface can have a slanted surface that resembles a ramp. The inside surface of the ring body of the securing device defines a bore and wherein the bore is configured to accommodate a valve opener. The bore can compress or bias the nose section of the valve opener, such as to a section or sections of the nose section that incorporate an elastomeric strip, band or material, to impart a pair of component forces on the valve opener. In another example, the securing device is sized and shaped to be spaced from the nose section when the male Luer tip abuts the female Luer of the catheter hub.

A canted coil spring can be used with the present catheter assembly or device. The canted coil spring has a plurality of interconnected coils that are all canted generally along the same direction. The spring can be made from a metal material. The canted coil spring can have a length configuration with two free ends. The canted coil spring can also be in a ring configuration with two ends of the spring length connected. Canted coil springs are well known in the spring art and the coils of the canted coil spring are understood to be deflectable or compressible in the radial direction relative to the ring centerline.

A canted coil spring in a spring ring configuration can be incorporated as a securing device. The canted coil spring, as a securing device, can be abutted against the proximally facing surface of the valve and can be abutted against a shoulder inside the interior of the catheter hub to secure the spring ring within the interior of the hub.

The proximally facing surface of the valve may have a mating depression to mate with or support the distal arc of the canted coil spring. In the valve opener proximal position, the coils of the canted coil spring contact both the interior surface of the catheter hub and/or the valve and against the nose section of the valve opener. In other examples, the coils can be spaced from the surface of the nose section, such as not contacting the nose section, in the valve opener proximal position.

When a male Luer tip of a medical implement is inserted into a catheter hub to open or deflect the valve flaps of the valve, the canted coil spring is compressed by the nose section of the valve opener. Each coil of the plurality of coils of the canted coil spring can be compressed by the nose section of the valve opener, since coils of a canted coil spring compress when squeezed in the radial direction of the spring ring centerline.

The compression of the coils generates force vectors on the nose section since the coils tend to un-compress or recoil. The force vectors generated against the nose section include a force that is generally parallel to the lengthwise axis of the valve opener. The distally directed axial force vector is against the proximal valve surface of the valve, if the coils are compressed along one side by the valve, or by the interior of the catheter hub, if the coils are compressed along one side by the catheter hub, and the proximally directed force vector is against the valve opener.

When the male tip is removed, the coils of the spring expand and push against the nose section to impart a pair of component forces, including a proximally directed axial force vector. This in turn can assist in pushing the valve opener in the proximal direction to return the valve opener to its proximal position and to allow the valve to return to its closed position. The forces generated by the spring ring 244 to move the valve opener following removal of the male Luer tip can be in addition to the forces generated by the valve flaps of the valve returning to the relaxed or closed state to close the valve slits following removal of the male Luer tip. The proximally directed forces can move the valve opener from a distal position back to a proximal position inside the catheter hub, after the male medical implement is disconnected from the catheter hub.

In another example, the valve can be provided with an integrated or unitarily formed securing device. The integrated or unitarily formed securing device can be a retaining skirt section having a triangular cross-section. The additional surface area of the external surface of the skirt section, or the securing device, can assist in further retaining the valve in the catheter hub as the needle is removed and as the valve opener is pushed by a male Luer tip to open the valve.

The skirt section can be sized so that when the valve opener is pushed in the distal direction by the male Luer tip, the triangular cross-section of the skirt can be compressed, deformed, or biased by the tapered nose section and the interior of the catheter hub. Consequently, when the male tip, such as a male Luer of a syringe or a tip of an administration set, is removed, the triangular skirt can expand to impart a pair of component forces on the nose section, which includes a proximally directed axial force vector. This in turn assists in pushing the valve opener in the proximal direction to return the valve opener to its proximal position from the distal position and to allow the valve to return to its closed position.

In yet another example, the securing device in accordance with aspects of the invention has a ring body with a distal end with a curved lip defining a flange, which has a generally planar wall surface for abutting a surface of a valve. The ring body has a generally constant wall thickness that tapers outwardly from a first diameter at the distal end, just proximal of the flange, to a second larger diameter at the proximal end, which has a proximal edge which can abut or contact a shoulder inside a catheter hub to retain the securing device within the catheter hub. Alternatively, the shoulder can be eliminated and the proximal edge can form an interference fit with the inside edge of the catheter hub.

The wall surface of the ring body can have a slanted surface that resembles a ramp. The inside surface of the ring body of the securing device defines a bore and wherein the bore is configured to accommodate a valve opener and compress or bias the nose section of the valve opener to impart a pair of component forces, as previously discussed.

In the present embodiment, two or more leaf springs, for example, three to eight leaf springs, can be provided as part of the retention ring for retaining the valve. In another example, there can be only one leaf spring incorporated. The leaf springs can be formed by forming a symmetrical three-sided cut-out on the ring body and bending the cut-out inwardly to form the leaf spring. However, cut-outs can be other than a three-sided cut-out, such as a partial circle cut-out, the cuts can be non-symmetrical, or a multi-sided cut-out greater than three sides. Any number of cut-outs can be utilized to form leaf springs on a securing device to generate force vectors on a valve opener with three-sided cut-outs being preferred. After forming the one or more cut-outs, the direction of bending of the cut-outs to form the leaf spring(s) is the direction that allows the one or more leaf springs to contact the nose section of the valve actuator.

The leaf springs can be sized so that when the valve opener is pushed in the distal direction by a male Luer tip, the leaf springs are deformed, deflected, or biased by the tapered nose section of the valve opener. Consequently, when the male tip is removed, the leaf springs expands or un-bias to impart a pair of component forces on the nose section, which includes an axial force vector in the proximal direction.

The biasing forces of the leaf springs assist in pushing the valve opener in the proximal direction to return the valve opener from a distal position to its proximal position and to allow the valve to return to its closed position. The forces of the leaf springs can be in addition to the forces generated by the valve flaps of the valve returning to their relaxed or closed position to close the valve slits following removal of the male Luer tip. In the embodiment with one or more leaf springs, the nose section can be rigid without any pliable section or sections, which can optionally be included.

In an embodiment, the securing device can be a retention ring and the retention ring can be provided with integrated or unitarily formed flexible flaps or leaf springs. The securing device can embody an eyelet in which one or more leaf springs extend from a flange.

The securing device with the eyelet configuration can be used with catheter assemblies described herein. The, securing device has a flange for a ring body, which has an outside diameter (OD) and an inside diameter (ID) defining an opening. The flange can have a thickness, which can be the thickness of the metal sheet used to form the eyelet. The thickness of the flange and the thickness of the leaf springs can be the same or approximately the same. If the flange and the leaf springs are unitarily formed from a single metal sheet, then a thickness at the flange and a thickness at each of the leaf springs can be the same, to within fabrication tolerance of the thickness of the metal sheet.

In the eyelet embodiment, no cylindrical or elongated hollow body extends from the flange. Instead, two or more leaf springs, for example, three to eight leaf springs or at least one leaf spring, can extend directly from the flange. The drawings show four leaf springs incorporated with the flange and each leaf spring is approximately 90 degrees from an adjacent leaf spring. However, there can be three leaf springs or a different number. The leaf springs can be equally spaced along the contour of the flange. The leaf springs can help to center the valve actuator relative to the slits in the valve.

The leaf springs can extend from the flange ID, in the proximal direction, and each leaf spring can terminate with a proximal end edge. The proximal end edge of each of the leaf springs can be flat or radiused.

The leaf springs can be equally spaced or approximately equally spaced apart along the flange ID. The leaf springs can extend right at the boundary of the flange ID or away from the boundary, such as due to the bending to form the leaf spring or from the slits or cut outs used to create and recess each leaf spring from the flange ID, as examples.

Each leaf spring can have a width and a length that are sufficient to generate a component force on the nose section of the valve opener and collectively all of the leaf springs can generate a proximally directed force that can move the valve opener from a distal position to a proximal position following removal of the male Luer tip.

A pair of interior notches or slits can be provided at the flange ID and on either side edge of each leaf spring to permit each leaf spring to have a bend with a bent radius that is recessed from the flange ID. In other examples, the pair of interior notches can be omitted from the flange ID and the bend in the proximal direction at each bend can be square shape or right angle. Alternatively, the bent radius can extend somewhat inwardly of the flange ID when no interior notches or insufficient interior notches are incorporated.

The securing ring in the eyelet embodiment can be configured to secure the valve within the interior of the catheter hub, like other securing rings discussed elsewhere herein. The valve can be supported on the distally facing surface by an internal shoulder and on the proximally facing surface by the flange of the securing ring, which can be supported by an internal shoulder on the proximal side of the flange. The valve can therefore be secured or supported inside the interior of the catheter hub on the distal side by a shoulder and on the proximal side by a securing device, such as by the flange of the securing device.

In the valve opener proximal position, the actuation end of the valve opener can touch the proximally facing surface of the valve or can be spaced from the proximally facing surface of the valve, by a relatively small spacing. Whether there is touching or no touching between the valve opener and the valve in the valve opener proximal position, the nose section can be located within the boundary defined by the leaf springs, but does not touch the leaf springs. For example, in the valve opener proximal position, the nose section can be spaced from both the leaf springs and the flange. The spacing allows the valve opener to move distally into the valve to open the valve flaps before the nose section contacts the leaf springs.

In an example, the flange of the securing device can incorporate one or more reliefs or cut-outs on the flange OD. The reliefs can decrease the interference between the flange OD and the interior bore of the catheter hub during installation of the securing device into the catheter hub. For example, the reliefs at the OD allow the flange OD to be more flexible and the sections formed by the cut-outs to flex, independently as needed.

Each cut-out at the flange OD can be formed as a straight line cut across two points on the arc of the flange OD. In some examples, each cut-out can have a curve shape, a curve and at least one straight line cut, or a complex curve cut. In an example, a cut-out can be provided at each leaf spring, on the flange OD. In other examples, the cut-outs can be located out of alignment with the locations of the leaf springs, such as not directly on the OD part of the same ID location as a leaf spring. In still other examples, there can be more cut-outs or fewer cut-outs than the number of leaf springs.

In the valve opener distal position, the nose section projects through the valve slits to deflect the valve flaps in the distal direction and can compress the valve flaps between the nose section and the interior surface of the catheter hub, or the valve flaps can deflect or deform distally by the nose section of the valve opener without compression against the interior surface.

The actuation end of the valve opener can be distal of the distally deflected valve flaps. In other examples, the actuation end can be located at about the same axial position as the deflected valve flaps or proximal of the valve flaps but still allowing fluid to flow across the valve, in the proximal direction or distal direction.

The leaf springs can be located on the flange such that when the valve opener is pushed in the distal direction by a male Luer tip, the leaf springs are deflected radially outwardly by the tapered nose section of the valve opener. In an example, the proximal edge of each leaf spring is spaced from the interior of the catheter hub when deflected by the nose section of the valve opener. In another example, the proximal edge can contact the interior surface of the catheter hub.

The deflected leaf springs and the deflected valve flaps give rise to stored energy that can then push against the nose section of the valve opener to move the valve opener in the proximal direction, upon removal of the male Luer tip to release the stored energy.

When the male tip is removed from the catheter hub, the leaf springs can contract or un-bias to impart a pair of component forces on the nose section, which includes an axial force vector in the proximal direction. The biasing forces of the leaf springs can assist in pushing the valve opener in the proximal direction to return the valve opener from a distal position to its proximal position and to allow the valve to return to its closed position.

The forces generated by the leaf springs on the securing device on the valve opener can be in addition to the forces generated by the valve flaps of the valve on the valve opener when the valve flaps return to their relaxed or closed position to close the valve slits following removal of the male Luer tip. In the embodiment with one or more leaf springs on the securing device, the nose section of the valve opener can be rigid without any pliable section or sections, which can optionally be included.

Because the valve opener can move to a distal position into the valve, such as when pushed by a male Luer tip, to open the two or more valve flaps and can return to a proximal position when the male Luer tip is removed to enable the valve flaps to relax or close the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement into the valve by the valve opener to deflect the valve flaps and movement away from the valve.

In an alternative eyelet embodiment, the flange of the securing device or ring, which can have an ID, and OD, and a thickness, can be shaped to have an arc or curved cross-section. That is, the distally facing surface and the proximally facing surface of the flange are arc-shaped or curved. In an example, the distally facing surface of the flange has a convex shape and the proximally facing surface of the flange has a concave shape. The shaped flange can facilitate installation as the direction of insertion of the securement device and the arc-shaped flange along the cross-section allows the flange OD to smoothly ride against the interior surface during installation. The curved cross section can also strengthen the flange against deformation during installation.

The reliefs or cut-outs at the flange OD of the eyelet can be out of alignment with the leaf springs. Using the hour hand of a clock for reference, the leaf springs can be located at the 2, 4, 8, and 10 o'clock positions along the flange ID while the cut-outs can be located at the 3, 6, 9, and 12 o'clock positions along the flange OD. In other examples, the locations of the leaf springs along the flange ID and the locations of the cut-outs along the flange OD can change. Also, the number of leaf springs and cut-outs can vary, such as having two leaf springs and three cut-outs or three leaf springs and two cut-outs.

Due to the curved or arc-shaped cross-section of the alternative eyelet embodiment, the leaf springs can be bent, such as to form the leaf spring with a free end in the proximal direction, without having to include cut-outs or slits along the flange ID. However, slits or cut-outs may be incorporated to assist or facilitate bending of the tabs to form the leaf springs.

In yet another example, a catheter assembly can utilize a securing device that embodies a retention ring made from an elastomeric material. For example, the securing device may be made from an elastomeric material, such as an O-ring, that can have stored energy when biased or deformed. Thus, when the elastomeric material releases its stored energy, it can provide a proximally directed force to the valve opener to move the valve opener from a distal position to a proximal position.

In an example, the elastomeric material, which can be an O-ring, can be compressed between the valve opener nose section and the inner wall of the catheter hub in the distal position of the valve opener. The securing device can have a structure that embodies an O-ring of various possible cross sections, such as round, oval, or polygonal, such as square, rectangular, or triangular shaped. The securing device can be an elastomeric ring with a round cross-section. The securing device can be separately formed from the valve and used with the valve to secure the valve inside the interior of the catheter hub.

The valve used with the catheter hub can be secured or supported on the distal side by an internal shoulder inside the catheter hub, which can prevent or limit axial distal displacement of the outer perimeter of the valve, but still allows the valve flaps to deflect in the distal direction when pushed by a valve opener. The valve can be secured or supported on the proximal side by the securing ring, or elastomeric ring of the present embodiment. The elastomeric ring can abut an internal shoulder inside the catheter hub to secure the elastomeric ring, and hence the valve, from displacing in the proximal direction.

The securing device and the nose section of the valve opener can be spaced from one another in the valve opener proximal position. The gap or spacing between the two provides clearance for the valve opener to move in the distal direction to open the valve, such as to deflect the valve flaps, before closing the gap, contacting or hitting the securing device with the valve opener.

The actuating end at the nose section of the valve actuator can be located within the bore defined by the securing device, but spaced from or not contacting the securing device. The tapered surface of the nose section can also be spaced from the securing device. This spacing or gap allows the valve actuating element to move forward in the distal direction before hitting or contacting the securing device. The actuating end of the valve actuator can be in contact with the proximally facing surface of the valve. In other examples, the actuating end can be slightly spaced from the proximally facing surface of the valve.

A male Luer tip usable herein can have a threaded collar for engaging the lugs or external threads on the catheter hub to maintain the valve actuator in the distal position to open the valve.

In an example, the valve opener is configured to move distally when advanced by the male Luer tip. The amount or distance that the valve opener moves in the distal direction should be sufficient to allow the actuating end and the nose section to deflect the valve flaps in the distal direction to open the slits to then open fluid communication between the male Luer tip and the catheter tube.

In an example, the actuating end of the valve opener moves distal the valve flaps and the valve flaps can be compressed between the interior of the catheter hub and the tapered surface of the nose section, or the valve flaps are deflected or deformed in the distal direction by the nose section of the valve opener without being compressed. In some examples, the actuating end can move a distance that is equal to the ends of the valve flaps or short of the ends of the valve flaps, but still opening the valve sufficiently for free flow in both directions.

In an example, the elastomeric ring of the securing device acts like a biasing member. For example, when the nose section is pushed against the securing device and compressing or biasing the securing device between the nose section and the interior surface of the catheter hub, stored energy is imparted to the elastomeric material, which can embody an O-ring and can exert an opposite biasing force against the nose section of the actuator. Thus, when the nose section is pressed against the elastomeric ring, the elastomeric ring can impart a pair of component forces or force vectors on the nose section, which can include a force that acts generally parallel to the lengthwise axis of the catheter hub in a proximal direction.

Upon withdrawal of the male Luer tip, such as when replacing an IV fluid bag attached to the male Luer tip, the distally directed force acting on the proximal edges of the two plunger elements by the male Luer tip is removed or ceased and the female Luer is unoccupied by any external object. This allows for the valve opener to return to its proximal position, now vacated by the male Luer tip.

In an example, the elasticity of the valve allows the valve flaps to recoil to their more relaxed state, such as to move to close the slits or close the valve disc. This recoiling action of the valve flaps and the shape of the nose section of the valve opener allow the valve flaps to impart force vectors on the nose section to cause the valve opener to move from a distal position to a proximal position. Additionally, and as discussed above, the elasticity of the securing device can exert a returning force against the nose section to move the valve opener in the proximal direction.

Aspects of the invention is therefore understood to include a catheter assembly or needle device comprising a catheter hub having a catheter tube extending in a distal direction, a needle attached to a needle hub and the needle extending through the catheter hub and the catheter tube. The catheter hub can comprise a body having an exterior surface and an interior surface defining an interior cavity. A valve and a valve opener can be located inside the interior cavity. In an example, a securing device having a body defining a bore can be located proximal of the valve and secures the valve in the catheter hub.

The securing device can provide an interference or can bias the valve opener, or vice-versa, with the valve opener when the valve opener is advanced in the distal direction by a male Luer tip to open the valve flaps of the valve and wherein the interference fit provides force vectors that include a vector that extends generally parallel to the lengthwise axis of the catheter hub in a proximal direction to return the valve opener from a distal position to a proximal position, when the male Luer tip is removed from the catheter hub.

The securing device can additionally provide a securing function for securing the valve inside the catheter hub and preventing the valve from inadvertent proximal displacement to dislodge from the catheter hub. If the valve otherwise displaces from the interior of the catheter hub, the valve can fail to close properly and leak blood. The securing device can be an elastomeric material. The material preferably ranges between 30 and 70 Shore A hardness. It can also have a shore A hardness below 30 or above 70. In an example, the elastomeric material is an O-ring. In a particular example, the O-ring can have a round cross-section.

Because the valve opener can move to a distal position into the valve, such as when pushed by a male Luer tip, to open the two or more valve flaps and can return to a proximal position when the male Luer tip is removed to enable the valve flaps to relax or close up the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of the valve opener into the valve to deflect the valve flaps and movement away from the valve to allow the flaps to close.

In a further catheter assembly embodiment, the elastomeric material, which can be an O-ring, can have a generally square or polygonal cross-section.

In a further embodiment in accordance with aspects of the invention, the valve is provided with an integrated or unitarily formed securing device. In an example, the integrated or unitarily formed securing device can be a retaining skirt section formed with the valve disc. The skirt section can have a generally constant thickness and a proximal end surface, which can be sized to abut or contact an internal shoulder of the catheter hub to secure the valve inside the catheter hub, from proximal movement. The proximal end surface of the skirt section can have a sufficient thickness so that part of the skirt section is exposed radially of the internal shoulder. This exposed portion of the skirt section can allow or provide a target for the valve opener to push against to compress, deform, or bias the skirt section.

The valve can have a valve disc and an integrated skirt. In an example, the valve disc and the skirt section are unitarily formed. The skirt section can be viewed as a generally cylindrical length having an open proximal end. The valve disc can have a plurality of slits or valve disc slit portions defining a plurality of valve flaps. In an example, the wall thickness of the valve disc, in the axial direction, can be generally constant, without distinct first portions and second portions as shown and elsewhere in this description. However, distinct first portions and second portions can be incorporated with a valve having a valve disc and a skirt section.

In an embodiment, rather than incorporating a generally constant thickness along the length of the skirt section, the skirt section can incorporate a ramped surface along a cross-section. For example, the valve with the valve disc can have distinct first and second portions and can have a skirt section with a ramped cross-section.

In an alternative embodiment, a valve opener can have a body comprising a nose section, two plunger elements, two projections, and two stabilizing elements, like other valve openers described elsewhere herein. In the present alternative embodiment, a transition section is provided proximal of the nose section. The transition section can include a pair of opener shoulders and each having an abutting edge. The two opener shoulders can be spaced from one another and the two abutting edges can be located approximately at a same axial point or location on the valve opener, on different sides of the nose section, to push into the valve at about the same time when the valve opener is advanced by the male Luer tip.

Each opener shoulder can include a slanted or sloped surface extending proximally of the abutting edge. Each slope surface can have a constant slope or a complex slope. The two opener shoulders can be located proximate a landing section at the transition section of the valve opener. Raised lips or ribs can be provided sparingly thoroughly the body of the valve opener to increase stability and/or strength.

The outside diameter (OD) at the landing section can be generally constant. In an example, a length of the landing section can have the same OD along the length thereof. In still other examples, there can be a slight increasing slope or a slight decreasing slope. The sloped surface at the landing section can be practiced so long as the landing section does not abut or interfere with the skirt section and/or does not weakened the transition section thus rendering it operable as a valve opener. The bore at the nose section and the landing section can have a generally constant inside diameter (ID).

Distal of the landing section, on the exterior, the nose section can have a generally frustoconical shaped structure. The tapered surface of the nose section can allow the valve flaps to impart a pair of component forces, which can include a proximally directed force, to return the valve opener to its proximal position after removal of the male Luer tip.

The two abutting edges of the two opener shoulders can push against the proximal surface of the skirt section of the valve due to the male Luer tip pushing the valve opener in the distal direction into the valve. Overlapping surfaces of the skirt section and the opener shoulders can indicate interference or compression of the skirt section between the distal shoulder of the catheter hub and the abutting edges of the valve opener. Thus, when the valve is opened by the valve opener, the valve flaps are compressed between the nose section of the valve opener and the interior surface of the catheter hub, or the valve flaps are deflected or deformed in the distal direction by the nose section of the valve opener, and the skirt section is compressed or deformed between the distal shoulder of the catheter hub and the two abutting edges of the valve opener.

In some examples, the two opener shoulders with tapered surfaces and abutting edges may be omitted or modified. For example, the nose section can extend directly to a stepped shoulder at the transition section without the tapered shoulder. Without the tapered shoulders, abutting surfaces on the stepped shoulders can compress the skirt section. In other examples, the tapered shoulders can have different shapes, such as be generally square or have square surfaces without any tapered surface so that the abutting edges are approximately the same height as the shoulders themselves. In other words, the abutting edges can be provided with the valve actuator, on two sides of the nose section, without the tapered shoulders.

Where the abutting edges and the shoulders with the tapered surfaces are omitted, the end surfaces of the two stepped shoulders can compress the skirt section. The size and shape of the stepped shoulder and the nose section can be adjusted to compress the skirt section when the tapered shoulders are omitted. In using the alternative valve opener without the tapered shoulders, the abutting edges of the two stepped shoulders can push against the proximal end surface of the valve directly.

The compression, deflection, deformation or bias of the various surfaces or sections of the valve when activated by the valve opener can create stored energy in the valve. When the male Luer tip is removed from the female Luer of the catheter hub, the stored energy can be released in the form of the valve flaps and the skirt section returning to their more relaxed state. Consequently, the valve flaps can exert a proximally directed force against the nose section and the skirt section can exert a proximally directed force against the two abutting edges to move the valve opener from a distal position to a proximal position.

Because the valve opener can move to a distal position into the valve, such as when pushed by a male Luer tip, to open the two or more valve flaps of the valve and the valve opener can return to a proximal position when the male Luer tip is removed to enable the valve flaps and the skirt section to relax or close up the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of a valve actuator into the valve to deflect the valve flaps and movement away from the valve.

The valve, such as the valve flaps or the skirt section of the valve can be deflected, biased, or deformed by a first structure, such as the valve opener, moving into the valve without requiring a second structure to be located opposite the first structure, although optionally the second structure can be incorporated. For example, the valve flaps can deflect by the valve opener as the valve opener moves in the distal direction. The valve flaps therefore deflect in the distal direction by the valve opener with or without a shoulder or some rigid surface located on the distal side of the valve flaps. When there is a shoulder or a rigid surface, the valve flaps can still deflect in the distal direction by the valve actuator and can be compressed between the nose section and the shoulder or rigid surface. Other objects can be deflected, biased, or deformed without an opposing structure, such as a leaf spring being deflected, biased, or deformed by the nose section of a valve opener or a spring C-ring or helix being expanded by insertion of a tapered section of the nose section.

Aspects of the invention can be understood to include a catheter assembly or needle device comprising a catheter hub having a catheter tube extending in a distal direction, said catheter hub comprising a body having an exterior surface and an interior surface defining an interior cavity. A valve and a valve opener can be located inside the interior cavity. In an example, a securing device can have a body defining a bore located inside the catheter hub and proximal of the valve. In an example, the securing device can be unitarily formed with the valve and can be a skirt section. For example, a valve disc can be unitarily formed with a valve skirt or skirt section and wherein the valve skirt can act as a securing device to retain the valve disc within the interior of the catheter hub.

The valve flaps of the valve can impart a proximally directed return force to return the valve opener from a distal position to a proximal position. Additionally, the valve opener can include one or more abutting edges to compress, deform, or bias the skirt section axially against a distal shoulder of the catheter hub. In other words, the valve skirt or skirt section can have a length and wherein the valve opener can compress or deform the valve skirt during actuation of the valve opener to a distal position to open the valve and decrease the length of the valve skirt from a first length to a shorter second length. When the skirt section decreases in length due to the valve actuator, the skirt section receives stored energy. The skirt section can therefore provide an axially directed force proximally against the valve opener when the stored energy is released, such as to the one or more abutting edges of the valve opener, to return the valve opener to a proximal position, upon removal of the male Luer tip.

In an example, the securing device can provide an interference with the valve opener, such as an elastomeric part of the valve opener, when the valve opener is advanced in the distal direction by a male Luer tip to open the valve flaps of the valve, such as to deflect the valve flaps in the distal direction by the nose section, and wherein the deflection can provide force vectors that include a force vector that extends generally parallel to the lengthwise axis of the catheter hub in a proximal direction to return the valve opener from a distal position to a proximal position, when the male Luer tip is removed from the catheter hub. In an example, the interference, bias, deflection, or compression provides stored energy to a skirt section of the valve. The stored energy can release to push against one or more abutting surfaces of the valve opener in the proximal axial direction.

The valve opener can have multiple surfaces, such as a nose section and one or more abutting edges, for deforming a valve at multiple distinct locations of the valve to provide stored energy to the valve. The deformed surfaces of the valve can include the valve flaps and other surfaces of the valve, different from the valve flaps. For example, in addition to the valve flaps, the skirt section can compress axially by the valve opener.

The catheter hub can include a needle projecting through the catheter hub, the valve, the valve opener, the securing device and the catheter tube. The needle can attach to a needle hub at the needle's proximal end.

In yet another needle assembly or catheter assembly embodiment, the catheter hub, catheter tube, valve, valve opener, and securing device can be similar to those shown and described elsewhere with a few exceptions. In the present embodiment, an annular slit or annular channel can be provided on the proximally facing surface of the valve with an enlarged gap to receive the distal end of the securing device. That is, the enlarged gap of the annular channel of the present embodiment can contact the outside surface of the ring body of the securing ring but not the inside surface of the ring body, due to the enlarged gap. The ring body can also contact the end surface or distal surface of the annular channel to control or set the depth of the annular channel relative to the ring body. This configuration allows the securing device to retain the valve within the interior of the catheter hub while relaxing tolerance or simplify manufacturing requirements for forming or creating the annular channel since the inside surface of the ring body does not have to be gripped by the annular channel. A channel is also easier to form by standard molding techniques than partially slitting the valve disc.

The ring body of the retention ring can have a wall with a length between the proximal end and the distal end with a generally constant wall thickness and a curved body section at the proximal end of the retention ring. The wall of the ring body can have an interior that defines a bore for accommodating the nose section of the valve opener.

The wall of the securing device can be generally cylindrical except for the curved body section at the proximal end. In an example, the proximal end of the retention ring can have an outwardly curved lip for securing the retention ring against an optional internal shoulder of the catheter hub. Once located against the internal shoulder, the securing device can help to secure the valve from displacing in the proximal direction. The valve can be secured or supported from distal movement by being located against a shoulder of the catheter hub on the distally facing surface of the valve. In some examples, the curved lip of the retention ring has an interference fit with the interior of the catheter hub without a shoulder.

One or more leaf springs can be provided with the securing device. Four leaf springs can be provided with the securing device and equally spaced from one another, at approximately the 2, 6, 8, and 10 o'clock positions. However, the leaf springs can be located at different arc positions of the ring body. In an example, a leaf spring can be formed by making at least two cuts through the proximal edge of the ring body. As shown, the leaf spring is formed from two generally parallel cuts to enable the metal to be bent to form the leaf spring and to form two side edges of the leaf spring at the proximal end of the ring body.

In one example, all leaf springs incorporated with the present securing device can be formed in the same manner, such as by utilizing two generally parallel cuts. In other examples, the cuts can be non-parallel. In still other examples, a combination of different leaf springs can be practiced. For example, the ring body can have two proximally located leaf springs with cuts formed through the proximal end of the ring body and two leaf springs formed between the distal end and the proximal end of the ring body.

In an example, the cut or cuts for forming a leaf spring can be made through the proximal edge of the ring body or can be made near but distal of the proximal edge of the ring body.

In still other examples, fewer than four leaf springs, such as three, two, or one, or greater than four leaf springs can be practiced, such as five, six, or seven leaf springs. Additionally, spacing between the cuts can vary to change the width of or the size of the leaf springs, which can change the spring force or biasing force generated by the leaf springs.

The cuts through the proximal end to form the leaf springs can have the advantage of creating proximal sections between two adjacent leaf springs. The proximal sections can deflect or flex when sliding the securing device into the catheter hub to secure the valve. The ability of the proximal sections to deflect or flex can decrease the insertion force for installing the securing device. As with the embodiment described above or elsewhere, there can be a cut out instead of a slit between the leaf spring and the proximal end of the ring body. This can increase the flexibility of both the leaf spring and the proximal end of the ring body.

The securing device and the nose section of the valve opener can be spaced from one another in the valve opener proximal position. The gap or spacing between the two can provide clearance for the valve opener to move in the distal direction to open the valve, such as to deflect the valve flaps, before contacting or hitting the securing device. In the state shown, the actuating end at the nose section of the valve actuator can be located within the bore defined by the securing device, but spaced from or not contacting the securing device.

The actuating end and the nose section can be spaced from a cylinder defined by the plurality of leaf springs. This spacing or gap can allow the valve actuating element to move forward in the distal direction before hitting or contacting the securing device, such as before hitting the leaf springs. The actuating end can contact the proximally facing surface of the valve in the ready to use position. In other examples, the actuating end can be slightly spaced from the proximally facing surface of the valve.

In an example, the valve opener is configured to move distally when advanced by a male Luer tip. The amount or distance that the valve opener moves in the distal direction should be sufficient to allow the actuating end and the nose section to deflect the valve flaps in the distal direction to open the slits to then open fluid communication between the male Luer tip and the catheter tube. In the example shown, the actuating end of the valve opener moves distal of the valve flaps and the valve flaps can be compressed between the interior of the catheter hub and the tapered surface of the nose section, or the valve flaps can be deflected or deformed distally by the nose section of the valve opener with or without compression. As shown, the actuating end moves a distance that is equal to the ends of the valve flaps or short of the ends of the valve flaps but still opening the valve sufficiently for free flow in both directions.

In an example, the tapered surface of the nose section deflects or biases the plurality of leaf springs radially outwardly to provide the leaf springs with stored energy. The curved lip can act like a biasing member. Thus, upon release of the leaf springs, the leaf springs impart a pair of component forces or force vectors on the nose section of the valve opener, which can include a force that acts generally parallel to the lengthwise axis of the catheter hub in a proximal direction.

Upon withdrawal of the male Luer tip, such as when replacing an IV fluid bag attached to the male Luer tip, the distally directed force acting on the proximal edges of the two plunger elements by the male Luer tip is removed or ceased and the female Luer is unoccupied by an external object. This can allow the valve opener to return to its proximal position, now vacated by the male Luer tip. In an example, the elasticity of the valve allows the valve flaps to recoil, by releasing its stored energy, to their more relaxed state. This recoiling action of the valve flaps and the shape of the nose section of the valve opener can allow the valve flaps to impart force vectors on the nose section to cause the valve opener to move from a distal position to a proximal position. Additionally, the leaf spring or leaf springs acting on the nose section can also exert a proximally directed force to further aid in returning the valve opener to its proximal position.

Because the valve opener can move to a distal position into the valve, such as when pushed by a male Luer tip, to open the two or more valve flaps and the valve opener can return to a proximal position when the male Luer tip is removed to enable the valve flaps to relax or close up to close the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of a valve actuator into the valve to deflect the valve flaps and movement away from the valve to allow the valve flaps to close.

A further aspect of the invention is a catheter assembly comprising a hub body of a catheter hub with a side port pointing in the proximal direction and having an elongated body that is formed at an acute angle to the lengthwise axis of the hub body. The side port can be unitarily formed with the hub body of the catheter hub. The catheter hub with the side port can be called or referred to as an integrated catheter, as further discussed below.

The integrated catheter with side port can have similar components located inside the catheter hub as other catheter hubs described elsewhere herein. For example, the catheter hub of the integrated catheter assembly can have a valve, a valve opener, a securing device, and a needle guard located inside the catheter hub. Optionally the securing device can be unitarily formed with the valve. Optionally the needle guard can be located outside of the catheter hub, such as in a third hub, which is separate from the catheter hub and the needle hub.

The side port can have a bore with an inlet opening. The bore of the side port can be in fluid communication with the interior cavity of the catheter hub and with the lumen of the catheter tube. In an example, the bore of the side port can be in fluid communication with the interior chamber or interior cavity distal of the valve and the catheter lumen.

Following removal of the needle and the needle hub after successful venipuncture from the catheter hub, the one or more flaps of the valve can close to isolate the interior cavity into a distal chamber distal of the valve and a proximal chamber proximal of the valve. The side port can be isolated from the proximal chamber of the interior cavity due to the valve. However, when the needle is located in the catheter tube and the needle deflects one or more of the valve flaps, there may be fluid communication with the proximal chamber.

A tubing can connect to the side port and a fluid connector can connect to the opposite end of the tubing.

A vent plug can connect to the proximal opening of the needle hub, similar to other vent plugs described herein. An optional paddle grip can be incorporated with the needle hub, the needle hub usable with a catheter hub. When incorporated, the paddle grip can provide a grip, which is closer to the puncture point during insertion of the needle into the vein. In general, the closer to the puncture point the more accurate the puncture can be made. When incorporated, the paddle grip can be unitarily formed with the needle hub.

The paddle grip can embody a generally flat structure extending to a side of the needle hub and can have a length that extends in the distal direction. The paddle grip can have a hump-like or curved-like outer contour with a rounded outer edge or can have other shapes. Surface bumps or gripping features can be incorporated with the paddle grip to facilitate gripping.

The paddle grip can be adjustable for a left-handed user or a right-handed user by rotating the needle hub about the lengthwise axis of the needle. In some examples, the paddle grip can be formed with a clip ring and the clip ring can slide onto the needle hub. The clip ring can be adjustable or rotatable about the needle hub to allow the position of the paddle grip to change as desired by the practitioner. Exemplary adjustable paddle grips are disclosed in U.S. Pub. No. 2017/0173304A1, the contents of which are expressly incorporated herein by reference.

A valve and a valve opener can be located inside the catheter hub of an integrated catheter. The valve can embody the valve shown in FIG. 13 and can be held between a distal shoulder and a proximal shoulder. The valve can have more than one slit and two or more flaps, such as three slits and three flaps or four slits and four flaps. The valve can have a valve disc with a constant thickness or with varying thicknesses.

The valve opener can be located proximal of the valve and can include a nose section having an actuating end for pushing into the valve to open the one or more slits of the valve disc to deflect two or more flaps. The valve opener can include at least one plunger element with two spaced apart plunger elements being more preferred, which can have one or more gaps therebetween for fluid flow.

A stabilizing element can connect or attach to the two plunger elements. Two stabilizing elements can connect to the two plunger elements, at opposite side edges of the plunger elements. The two stabilizing elements and the two plunger elements can define an inside opening that is smaller compared to the dimension of the needle guard at the two elbows when biased by a needle, as previously described. Thus, when the needle biases the two arms of the needle guard apart, the needle guard is prevented from moving proximally of the two stabilizing elements due to the size difference.

In an example, the elbows of the needle guard are located distally of the two stabilizing elements, distal of an internal shoulder inside the catheter hub. Thus, in addition to the two stabilizing elements, the needle guard can be held inside the catheter hub by the proximal shoulder in the ready to use position and during retraction of the needle until the needle tip moves proximally of the two distal walls of the two arms, as previously discussed.

A tubing or tubing length can be attached to the side port at a first end of the tubing and to a fluid connector at a second end of the tubing. The fluid connector can embody a number of different devices, such as a plug septum or a needleless valve. In an example, the fluid connector is a needleless valve comprising a housing having a moveable piston located internally thereof. The housing can have an inlet opening having a female Luer for receiving a male Luer tip, such as a syringe tip. The syringe can be used to open the fluid connector without a needle by compressing the piston.

When inserted into the inlet opening of the fluid connector, the male Luer tip of a syringe can compress the piston to open a fluid pathway between the inlet and the outlet of the housing. The outlet of the housing is connected to the tubing. Thus, fluid, such as medication, supplement or medicament, dispensed from the syringe via the male Luer tip can flow through the needleless valve or fluid connector, out the outlet of the housing, into the tubing to then flow through the side port, then into the distal chamber of the catheter hub, and then into the lumen of the catheter tube and into the patient.

In use, the catheter assembly with the side port of an integrated catheter assembly can be gripped using a paddle grip, if incorporated, and then inserted into the vein with the needle tip and the tip of the catheter tube. If there is no paddle grip, then the practitioner can grip the needle hub, and possibly also the catheter hub together. Primary blood flash back can be viewed when blood flows through the needle and into the needle hub. With primary flash back confirmed, the practitioner can then pull the needle in the proximal direction to permit blood to flow between the needle and the catheter tube to check for secondary blood flash back.

If secondary blood flash back is confirmed, the user can then insert the catheter assembly further into the vein by pushing the catheter tube further into the vein for vascular access. The needle and the needle hub can then be completely removed from the catheter tube and the catheter hub. Upon retracting the needle, the needle tip will move proximally of the two distal walls of the needle guard, which allows the two arms of the needle guard to move together and release from the stabilizing elements. As the change in profile engages the opening on the proximal wall of the needle guard, further retraction of the needle will remove the needle guard from the catheter hub. If the needle is pulled straight out of the catheter hub then the change in profile may not engage the opening on the proximal wall of the needle guard.

Following removal of the needle from the integrated catheter, the plurality of valve flaps of the valve can recoil or return to their relaxed state to close the slits and restrict flow in the proximal and distal directions through the valve. In an example, the actuating end at the nose section of the valve actuator or opener can be proximal of the valve in the valve opener proximal position, spaced from the proximally facing surface of the valve and spaced from the securing device, if incorporated.

The tapered surface of the nose section is also spaced from the securing device, if incorporated. This spacing or gap between the nose section and the securing device, if incorporated, allows the valve actuating element to move forward in the distal direction, when pushed by a male Luer tip, before hitting or contacting the securing device. This arrangement provides room for the valve opener to be displaced in the distal direction to open the valve. In an example, distal advancement of the valve opener can be stopped when the male Luer tip abuts the female Luer of the catheter hub in a Luer fit, as described elsewhere herein. The actuating end of the nose section can be spaced from the proximally facing surface of the valve in the ready to use position with the needle tip extending distally of the distal opening of the catheter tube and in the valve opener proximal position. In other examples, the actuating end can contact the proximally facing surface of the valve prior to being advanced in the distal direction by the male Luer tip.

In an example, an IV drip line of an IV administration set can be connected to the catheter hub of the integrated catheter via the proximal opening of the catheter hub. With the catheter hub occupied by an IV administration set, the fluid connector connected to the catheter hub via the tubing and the side port can be used to infuse medication to the patient, such as via a syringe. Alternatively, an IV drip line of an IV administration set can be connected to the fluid connector and the proximal opening of the catheter hub can be used to infuse medication, such as via a syringe.

A valve opener in accordance with further aspects of the invention can include a transition section having a taper formed with several slanted segments. In other examples, the transition section can embody a smooth curve or single slanted taper that increases from the nose section in the proximal direction. The nose section of the valve opener distal of the transition section can be generally frustoconical in shape and has a through opening for fluid flow. The tapered surface of the nose section can allow the valve flaps of the valve to impart a pair of component forces, which can include a proximally directed force, to return the valve opener to its proximal position after removal of the male Luer tip.

In an example, two stabilizing elements are incorporated with the valve opener. Each stabilizing element can connect to two plunger elements. Compared to the stabilizing elements of FIG. 33, at least one of the stabilizing elements of the alternative valve opener can have a width defined between a distal edge and a proximal edge that can vary in width along the length of the bridge defining the stabilizing element. For example, the stabilizing element can have a width between a first end and a second end, or the two ends that attach to the two plunger elements, and wherein the width can be narrow near the two ends but wider near the middle of the length.

The wider part of the stabilizing element can range from 25% to 75% of the length of the stabilizing element. However, like the valve opener of FIG. 33, one or both stabilizing elements can have the same width along the entire length thereof, similar to the bridge defining the stabilizing element of FIG. 33. In an example, the wider part can be centrally positioned between the two ends of the stabilizing element. In some examples, a cut-out or a recess can be incorporated on the proximal edge of one or both stabilizing elements.

In an example, the distal edge of the wider part of the stabilizing element can have a taper edge. The taper of the taper edge should originate at or closer to the exterior surface of the stabilizing element and slant towards the inner surface of the stabilizing element. In other words, the tip of the taper edge should be closer to the exterior surface of the stabilizing element than the interior surface of the stabilizing element. The configuration with the taper edge can facilitate release of a needle guard. Where two stabilizing elements are incorporated, both distal edges of the two stabilizing elements can incorporate the taper edge.

In some examples, each of the two stabilizing elements of the valve opener can have the same width along the length thereof and both stabilizing elements with the constant width can have a distal edge with a taper. For example, the distal edges of the two stabilizing elements can have the taper edge. In some examples, the valve opener can have two stabilizing elements, one with the same width along the length thereof and one with a wider part at a central location along the length thereof. One or the other or both of the stabilizing elements can have a distal edge with a taper. In other examples, one or both distal edges of the two different stabilizing elements can have a typical square or straight up and down edge, which can also allow a needle guard to release.

The two plunger elements can have sections that extend proximally of the proximal edge of the stabilizing element. In some examples, the proximal edge of the two plunger elements and the proximal edge of the stabilizing element, or of both stabilizing elements, can terminate generally along a same vertical plane. In the embodiment where the proximal edges terminate generally along the same plane, the distal edge of the stabilizing element can be extended in the distal direction, such as by increasing the width of the stabilizing element. Variation in the location of the distal edge can be utilized to control the interactions between the needle guard and the stabilizing element.

A needle guard in accordance with further aspects of the invention comprises a proximal wall having a perimeter defining an opening for accommodating a needle and to engage a change in profile formed with the needle. Two arms can extend distally of the proximal wall. Each arm can have a distal wall and an elbow located between the distal wall and the elongated arm portion of the arm.

Ribs or tabs can be incorporated at various portions of the needle guard to provide added rigidity or stiffness. Tabs or ribs can be provided on the edges of the proximal wall, on each of the two elongated arm portions, and on the distal walls. In a preferred embodiment, each distal wall is provided with a curved lip so that the curved lip abuts the side of the needle when the needle is located between the two arms. The curved lips can be incorporated with the needle guard so that the needle does not abut an edge of the distal wall, which can cause scraping, but instead with the flat exterior surfaces of the curved lips. In some examples, tabs or ribs can be omitted from the distal wall, such as from the curved lip, of the first arm or the longer arm.

The two arms of the needle guard intersect one another along the side view shown in both the retracted or needle exposed position and in the needle guarded or protective position. In other examples, the two arms can extend distally of the proximal wall on respective sides of the needle shaft but not cross the needle axis.

When the needle no longer biases the two arms of a needle guard and the two arms are allowed to move closer together, the dimension measured between the two elbows decreases compared to dimension at the two elbows when the two arms are biased by the needle. The needle can retract in the proximal direction until the change in profile abuts the perimeter defining the opening on the proximal wall. The perimeter of the proximal wall can have a smaller dimension than the largest cross-sectional dimension of the change in profile. This allows the needle to move in the proximal direction and engages the perimeter to remove the needle guard with the needle.

The two arms of the needle guard can have two different lengths. Thus, in the protective position, the two distal walls can overlap when looking down the axis of the needle. In an example, the angle between the distal wall and the elongated arm portion of the first arm can be larger than the angle between the distal wall and the elongated arm portion of the second arm.

In an example, each elongated arm portion of the two arms can be generally straight or linear, with possibly some slight bending or flexing when biased by the needle, up to the respective elbow. Then a single radius bend is provided to form the respective elbow and the respective distal wall. Another single radius bend can be provided to form the respective curved lip. At the elbow, the single radius bend can have a simple curve or a complex curve. However, unlike the needle guard of FIGS. 4 and 5, which has at least two bends and two changes in direction between the elongated arm portion of the arm and the distal wall of each arm, the present needle guard can have a single bend and a single change in direction between the elongated arm portion and the distal wall of each arm.

The single bend and the single change in direction produces a smooth or flat profile between the elongated arm portion and the elbow. The flat profile on the arm should be located so that interference with an edge of a stabilizing element of a valve opener, such as getting hung up or stuck, is minimized or reduced. Thus, there can be additional bends or changes in direction on each arm downstream of the first bend forming the elbow provided the transition between the elongated arm portion and the first bend for forming the elbow is generally flat or smooth in order to eliminate potential snag points that can cause sticking or binding, for a typical range of angle that the needle is oriented during removal. In general, use the needle is pulled straight out of the catheter hub along the same axis. In extreme cases the needle can be pulled out at an angle, until the needle contacts the upper proximal opening of the catheter hub. If the needle is pulled out at an angle higher than just touching the proximal opening of the catheter hub then this is abusive use, which could result in the bending of the needle.

The arms of the needle guard can have a smooth or flat profile between the elongated arm portion and the elbow, with only a single bend or change in direction. As shown, each elongated arm section of the first arm and the second arm can have sections with different arm widths. Each arm can also include a cut-out having a lip that resembles a hook. The cut out or cut-outs on the two arms allow the two arms to straddle the needle to provide lateral stability as the needle transitions from the ready to use position, with the needle tip exposed, to the protected position with the needle tip guarded.

The needle guards described herein can each be made from a stamped metal sheet, such as a stamped stainless-steel sheet, and using a stamping and bending method to form the needle guard in the shape shown.

When the needle tip retracts proximally of two distal walls of a needle guard following successful venipuncture, the bias by the needle on the two arms is removed, thus allowing the two arms to move closer together or to touch each other. This in turn reduces the dimension measured at the two elbows, which decreases thus allowing the needle guard to move proximally through the opening defined by the two stabilizing elements and the two plunger elements. However, during retraction of the needle and the needle guard through the opening, the practitioner may inadvertently tilt the needle during the proximal retraction. When this occurs, the needle guard may contact the distal edge of one or both stabilizing elements during retraction, to thereby catch and possibly get hung up by the contact between the needle guard and the stabilizing element. This would in turn hinder removal of the needle guard through the opening.

It is known that when an arm of the needle guard has more than one bends or changes in direction at the transition between an elongated arm portion and an elbow, the multiple changes in direction can catch the distal edge of one stabilizing element during retraction of the needle guard through the opening during removal of the needle. This in turn requires the user to reposition the angle of the needle relative to the lengthwise axis of the catheter hub to a value that is less than a maximum angle A during the retraction of the needle in order to avoid having the needle guard catch and hinder the retraction. In contrast, when the needle guard is used with a valve opener having one or two stabilizing elements, the single bend or change in direction between the elongated arm portion and the elbow produces a smooth or flat profile that does not readily catch against the distal edge of one or both stabilizing elements during retraction of the needle.

Thus, retraction through the opening can be facilitated by utilizing a needle guard having an arm with a single bend or change in direction to produce a smooth or flat profile that does not readily catch against the distal edge. Thus, a user can position the angle of the needle relative to the lengthwise axis of the catheter hub to a maximum angle B during the retraction in order to avoid catching and hindering the retraction, which is visually depicted in FIGS. 47 and 48 for discussion purposes. For two similarly sized catheter assemblies with similarly sized components but with different needle guards, one with one bend or change in direction and another with two or more bends or changes in direction, the angle B is larger than the angle A.

When the stabilizing element that the needle guard abuts or contacts during retraction in the proximal direction incorporates a tapered edge, the likelihood that the transition between the elbow with the elongated arm portion of a needle guard catches the tapered distal edge is reduced. Thus, even if the needle guard has two or more bends at the elbow and the catheter assembly has a stabilizing element with a tapered edge, the user holding the same sized catheter assembly can hold the needle at a higher angle A', which is higher than angle A. Similarly, if the needle guard has only one bend or one change in direction to produce a smooth or flat profile that does not readily catch against the distal edge, the user holding the same sized catheter assembly can hold the needle at a higher angle B', which is higher than angle A. Generally speaking, angle B' involving a needle guard with a single bend or change in direction and a valve opener with a stabilizing element with a tapered edge, is larger than angle A', involving a needle guard with two or more bends or changes in direction and a valve opener with a stabilizing element with a tapered edge. For discussion purposes, angle X can represent any one of angle A, A', B, or B', which is understood to depend on whether the needle guard has one or more bends or change in directions and whether the stabilizing element of the valve opener has a tapered edge.

Aspects of the invention are further understood to include a catheter assembly comprising a catheter tube having a lumen, a distal end opening, and a proximal end attached to a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a valve body comprising at least one slit, a proximally facing surface, and a distally facing surface located in the interior cavity of the catheter hub; a valve actuator disposed in the interior cavity of the catheter hub, said valve actuator having a nose section with a bore and a proximal section with at least one gap for fluid flow therethrough or thereacross and being slideable between a proximal position and a distal position inside the interior cavity when pushed by a male Luer; a needle guard having a protective surface located to a side of the needle in a ready to use position and transitionable to a position distal of the needle tip in a protective position to cover the needle tip from an inadvertent needle stick; wherein said needle guard has an arm with an elbow between an elongated arm portion and a distal wall and wherein the elbow has a single change in direction at a location that can contact a stabilizing element on the valve actuator during retraction of the needle guard without catching, hindering, and/or stopping the needle movement.

A securing device can be in contact with or integral to the valve at the proximally facing surface of the valve body for retaining the valve inside the interior cavity of the catheter hub, said securing device can comprise a retainer body having an interior surface defining a bore comprising a fluid path, a distal end, and a proximal end.

The catheter hub can have a side port attached to a tubing at a first end of the tubing. A fluid connector can connector to a second end of the tubing. The fluid connector can comprise a needleless connector. The catheter assembly can be referred to as an integrated catheter assembly.

The stabilizing element of the valve opener or actuator can have a distal edge. The distal edge can have a tapered edge. The taper of the taper edge should originate at or closer to the exterior surface of the stabilizing element and slant towards the inner surface of the stabilizing element. In other words, the tip of the taper edge should be closer to the exterior surface of the stabilizing element than the interior surface of the stabilizing element.

The needle guard can have an arm with a single change in direction between an elongated arm portion and a distal wall of the arm to produce a smooth or flat profile at the elbow, between the elongated arm portion and the distal wall, that does not readily catch against the distal edge of the stabilizing element of the valve actuator.

Methods of making and of using catheter assemblies and components thereof are within the scope of the present invention.

BRIEF DESCRIPTION OF THE DRAWINGS

These and other features and advantages of the present devices, systems, and methods will become appreciated as the same becomes better understood with reference to the specification, claims and appended drawings wherein:

FIG. 1 is a schematic perspective view of a catheter assembly or needle device in accordance with aspects of the invention.

FIG. 2 is a partial cross-sectional perspective view of the assembly of FIG. 1.

FIG. 4 is an enlarged partial cross-sectional side view of the assembly of FIG. 1.

FIG. 5 is a cross-sectional side view of the assembly of FIG. 4 rotated 90 degrees.

FIG. 6 is a cross-sectional side view of the assembly of FIGS. 1-5 with the needle and needle hub removed, such as following successful venipuncture and with the valve opener in its proximal position.

FIG. 7 is a cross-sectional side view of the assembly of FIG. 6 with the valve opener in its distal position and opening the valve.

FIG. 8 is a cross-sectional side view of an embodiment of a catheter assembly or needle device with the needle and needle hub removed, such as following successful venipuncture and with the valve opener in its proximal position.

FIG. 9 is a cross-sectional side view of the assembly of FIG. 8 with the valve opener in its distal position and opening the valve.

FIG. 12 shows a cross-sectional side view, a front view, and a front perspective view of a securing device in accordance with aspects of the invention.

FIG. 13 shows a cross-sectional side view, a front view, and a front perspective view of a valve and a securing device in accordance with aspects of the invention.

FIG. 14 shows a cross-sectional side view, a front view, and a front perspective view of another securing device in accordance with aspects of the invention.

FIG. 18 is a cross-sectional side view of another embodiment of a catheter assembly or needle device with the needle and needle hub removed, such as following successful venipuncture and with the valve opener in its proximal position.

FIG. 19 is a cross-sectional side view of the assembly of FIG. 18 with the valve opener in its distal position and opening the valve.

FIG. 20 is a cross-sectional side view of another embodiment of a catheter assembly or needle device with the needle and needle hub removed, such as following successful venipuncture and with the valve opener in its proximal position.

FIG. 21 is a cross-sectional side view of the assembly of FIG. 20 with the valve opener in its distal position and opening the valve.

FIG. 22 shows a cross-sectional side view, a front view, and a front perspective view of another securing device in accordance with aspects of the invention.

FIG. 23 is a cross-sectional side view of another embodiment of a catheter assembly or needle device with the needle and needle hub removed, such as following successful venipuncture and with the valve opener in its proximal position.

FIG. 24 is a cross-sectional side view of the assembly of FIG. 23 with the valve opener in its distal position and opening the valve.

FIG. 25 is a perspective view of a securing device that can embody an eyelet.

FIG. 26 is a perspective view of a securing device that can embody an eyelet in accordance to further aspects of the invention.

FIG. 27 is a cross-sectional side view of another embodiment of a catheter assembly or needle device with the needle and needle hub removed, such as following successful venipuncture and with the valve opener in its proximal position.

FIG. 28 is a cross-sectional side view of the assembly of FIG. 27 with the valve opener in its distal position and opening the valve.

FIG. 29 is a cross-sectional side view of another embodiment of a catheter assembly or needle device with the needle and needle hub removed, such as following successful venipuncture and with the valve opener in its proximal position.

FIG. 30 is a cross-sectional side view of the assembly of FIG. 29 with the valve opener in its distal position and opening the valve.

FIG. 31 is a cross-sectional side view of another embodiment of a catheter assembly or needle device with the needle and needle hub removed, such as following successful venipuncture and with the valve opener in its proximal position.

FIG. 32A is a cross-sectional side view of the assembly of FIG. 31 with the valve opener in its distal position and opening the valve and FIG. 32B is the same view rotated 90-degrees.

FIG. 33 is a perspective view of a valve opener provided in accordance with aspects of the invention.

FIG. 34 is a perspective view of a valve comprising a valve disc and a skirt section.

FIG. 35 is a perspective view of a valve comprising a valve disc and a skirt section provided in accordance with further aspects of the invention.

FIG. 36 is a cross-sectional side view of another embodiment of a catheter assembly or needle device with the needle and needle hub removed, such as following successful venipuncture and with the valve opener in its proximal position.

FIG. 37 is a cross-sectional side view of the assembly of FIG. 36 with the valve opener in its distal position and opening the valve.

FIG. 38a is a perspective view of a securing device comprising a plurality of leaf springs and FIG. 38b is a front view thereof.

FIGS. 39-41 are cross-sectional views of an alternative catheter assembly provided in accordance with further aspects of the invention, which can comprise a side port.

FIG. 43 is a perspective view of a valve opener or actuator provided in accordance with further aspects of the invention.

FIG. 44 is an enlarged sectional view of a stabilizing element comprising a tapered distal edge.

DETAILED DESCRIPTION

Figure 3:
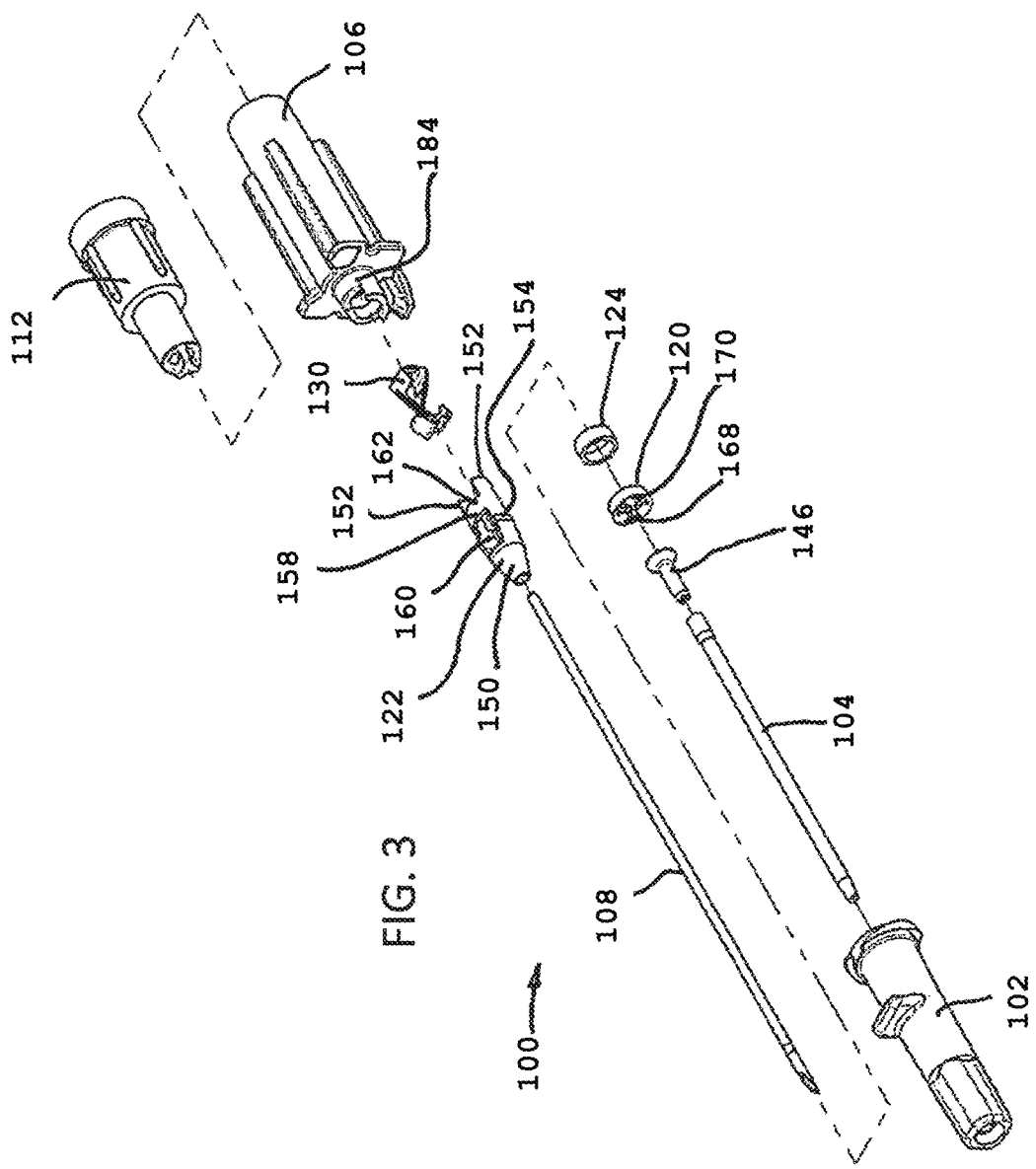
FIG. 3 is an exploded view of the needle device or catheter assembly of FIG. 1.

The present disclosure is generally related to needle devices, and more particularly to catheter assemblies having an improved valve system and related improved methods. The improvements involve a number of individual components and the combination of the components. In an example, the improvements comprise a structure and function of fixing the valve in a standard diameter sized catheter hub, providing a proximally directed axial force for returning the valve opener, also called a valve actuator, from a distal position to a proximal position when a male Luer is disconnected from the catheter hub, incorporating component or components inside a single body catheter hub that can restrict fluid flow, allowing actuation to permit fluid flow, preventing needle injuries, and combinations thereof. The single body catheter hub is understood as a one-piece catheter hub with a catheter tube extending from a distal end of the hub and a proximal opening at a proximal end for receiving a male medical implement, such as a male Luer tip.

FIG. 1 shows a catheter assembly 100, also referred to as a needle device or an over-the-needle catheter assembly, having a catheter hub 102 with a catheter tube 104, a needle hub 106 with a needle 108 attached thereto and the needle projecting through the catheter hub 102 and the lumen of the catheter tube 104. A vent plug 112 is located at a proximal end of the needle hub 106, and more particularly is attached to the proximal opening of the needle hub 106. The needle bevel at the needle tip 114 projects distally of the distal opening or catheter tube opening 116 of the catheter tube 104 in the ready to use position of FIG. 1. The needle hub 106 is coupled to the catheter hub 102 at the proximal opening of the catheter hub, which can have a female threaded Luer or Luer slip. The catheter hub 102 may incorporate a push tab and one or more surface features, such as ribs for pushing the catheter tube 104 into the vein of a patient and over the needle 108. The needle hub 106 can similarly incorporate surface features for a more secure grip when puncturing the vein and pulling out the needle 108 from the catheter tube 104. Unless otherwise indicated, the various components may be made from conventional materials using conventional techniques.

In an example, a pair of wings can be incorporated with the body 126 of the catheter hub 102 and each wing can extend laterally of the lengthwise axis of the catheter hub in opposite directions at the bottom of the catheter hub. The pair of wings can be used by a practitioner to secure the catheter hub to the patient after successful venipuncture, such as with an adhesive tape or adhesive dressing.

FIG. 2 is a partial cross-sectional perspective view of the needle assembly 100 of FIG. 1 with the catheter hub 102 exposed along a lengthwise direction to show a valve 120 and a valve opener 122 located inside the interior or interior cavity 123 of the catheter hub 102. The valve and the valve opener can be incorporated to control fluid flow through the catheter hub, such as to control infusion or aspiration through the catheter hub, as further discussed below. Also shown located inside the interior cavity 123 is a needle guard or tip protector 130, which can have a surface or a wall for preventing inadvertent contact with the needle tip when the needle is removed from the catheter tube and the catheter hub following successful venipuncture.

The needle guard or tip protector 130 can embody a structure with one or more components for preventing inadvertent contact with the needle tip. For example, the needle guard 130 can have a structure or a wall that moves from a position to the side of the needle shaft and proximal of the needle tip to a position distal of the needle tip to cover or block the needle tip from inadvertent contact. In an example, the needle guard 130 can be one of the types described in U.S. Pat. No. 10,166,370, the contents of which are expressly incorporated herein by reference. Aspects of exemplary needle guards are further discussed below.

The catheter hub 102 has a body 126 with an exterior surface and an interior surface defining the interior cavity 123. One or more shoulders or lips 176a, 176b, 176c (FIG. 4) may be incorporated in the interior 123 and can be used for seating the valve opener 122, the valve 120, and/or the needle guard 130 in the ready to use position. The needle guard 130 can be placed into the interior of the catheter hub 102 by a nose section 132 of the needle hub 106, which projects into the proximal opening 136 of the catheter hub 102. As shown, the needle assembly or catheter assembly 100 of FIG. 2 may be provided with a catheter hub 102 comprising an interior 123 having a valve 120, a valve opener 122, and a needle guard 130 located therein in the ready to use position. In an example, the needle guard 130 is optional and can be omitted. In still other examples, the needle guard 130 can be located substantially externally of the catheter hub. For example, a finger or a portion of a finger of the needle guard can be located inside the catheter hub while the remaining structure of the needle guard can be located externally of the catheter hub.

Also shown located inside the interior 123 of the catheter hub 102 of FIG. 2 is a device or structure 124 for securing or retaining the valve 120 inside the catheter hub 102, which can be referred to generically as a securing device, securing ring, or element 124. The securing device, ring or element 124 can have a structure that embodies a retainer, a retention ring, a retaining skirt, an O-ring of various possible cross sections, such as round, oval, square, rectangular, or a canted coil spring, among others. The securing device 124 can be separately formed from the valve 120 or be made part of the valve, such as being used with the valve, being integrated with the valve, or being unitarily formed with the valve. Unless the context indicates otherwise, the term securing device 124 can mean any of the noted structures and their equivalents. In an example, the securing device 124 is located in line with the valve 120, with the valve opener 122, and with the needle guard 130. In a particular example, the securing device 124 has a bore or opening for receiving the needle 108 and is in contact with both the valve and the interior of the catheter hub 102 for limiting proximal movement of the valve 120 inside the interior 123, for assisting in returning the valve opener 122 from a distal position to a proximal position, or for both purposes, as further discussed below. The valve opener or part of the valve opener 122 can be located inside the bore of the securing device 124 in both the ready position of the catheter assembly, as shown in FIG. 1, and in the used position, such as following successful venipuncture, as further discussed below.

As shown, the needle guard 130 can comprise a metallic body having a springing or resilient characteristic, a proximal wall 140, and at least one arm, or two arms (as shown), extending distally of the proximal wall 140. A change in profile 142 formed on the needle shaft, proximal of and near to the needle tip 114, can engage a perimeter defining an opening on the proximal wall 140 to limit distal movement of the needle guard off of the needle but allows the tip 114 to enter the needle guard 130. The change in profile 142 can comprise a crimp, a material buildup, a sleeve or any other increase in diameter, which will be larger than the opening in the proximal wall 140.

FIG. 2 shows the valve 120, the valve opener or valve actuator 122, the securing device 124, and the needle guard 130 being configured, such as being sized and shaped, to be accommodated in the interior 123 of the catheter hub 102, which can have a one-piece hub body, such as a unitarily formed single hub body, with a proximal opening having a female Luer and a distal end having a catheter tube extending therefrom, optionally with exterior threads or lugs (as shown). In other examples, the catheter hub 102 can be made from a multi-part hub body. For example, the catheter hub 102 can have a first hub body attached to a second hub body, such as by bonding or welding, to form the body of the catheter hub 102.

FIG. 3 is an exploded perspective view of the catheter assembly or needle device 100 of FIG. 1, shown with an exemplary valve 120, an exemplary valve opener 122, and an exemplary securing device 124. Also shown in FIG. 3 are a catheter hub 102, a catheter tube 104, a needle 108, a needle guard 130, a needle hub 106, and a vent plug 112, which when combined or assembled can form the needle device 100 of FIGS. 1 and 2. A metal bush or fitting 146 is also shown, which is conventional and can be used to secure the proximal end of the catheter tube 104 to the interior of the catheter hub 102. In other examples, as further discussed below, the valve 120, the valve opener 122, and/or the securing device 124 can vary from the embodiment shown, such as having different specific structural features. In some examples, the needle guard can be located outside of the interior of the catheter hub, or substantially externally of the catheter hub with only a finger or a tab extending partially inside the catheter hub.

In an example, the valve actuator 122 comprises a nose section 150 at the distal end of the actuator body. The nose section 150 can be elongated in structure and can be generally cylindrical or have a draft angle or taper that terminates in an actuation end 180 (FIG. 7) for pushing into the valve 120 to open the slits of the valve, as further discussed below. The actuation end of the nose section 150 can have a blunt distal end surface or has a sharp edge. A flow passage can extend through the nose section 150 for fluid flow. The nose section 150 can have a wall surface with a continuous circumference or a continuous perimeter section defining a lumen or flow passage. The wall of the nose section can be without a gap or a slit, such as a cylinder with a continuous wall. The nose section 150 can define a bore. The bore can have a constant bore diameter or can vary with the taper of the nose section. In some examples, a plurality of spaced apart slits and/or openings can be provided on the nose section, such as through the wall of the nose section, to permit flow or fluid flushing.

Two actuating elements or plunger elements 152 can extend proximally of the nose section 150. For example, the two plunger elements 152 can be unitarily formed with the nose section 150 and can extend from the nose section in the proximal direction. A gap or space can be provided between the two plunger elements 152, which can define a holding space. A needle guard or tip protector 130 can be located in the holding space, or between the two plunger elements 152. In an example, the two plunger elements 152 can each comprise at least two lengthwise edges and the edges are spaced from one another. The lengthwise edges of the plunger elements 152 can align with a lengthwise axis of the valve opener 122. A gap or space can be provided between the two plunger elements to function as a flow channel for fluid to flow therethrough or thereacross when fluid is passed through the catheter hub. In other examples, there can be more than one gap or flow channel formed with the valve opener for fluid flow. In still other examples, the two plunger elements can be connected together by two bridges so that the proximal end of the valve opener is a continuous wall structure, formed by part of the two plunger elements and the two bridges. In some examples, a single plunger element is used with the valve opener.

In an example, a projection 154 extends outwardly from an outer surface of one or both plunger elements 152. As shown, a projection 154 extends from the outer surface of each plunger element 152. Each projection 154 resembles a tab having a generally flat edge for abutting a shoulder or lip formed in the interior of the catheter hub 102. The tab surface of the projection 154 and the direction of the projection allows the valve actuator 122 to be inserted into the interior 123 of the catheter hub 102 and be seated within the catheter hub, as further discussed below. The projections 154 can be sized and shaped to abut or contact a shoulder 176c inside the catheter hub to limit proximal movement of the valve opener or actuator 122.

In an example, a transition section extends from the nose section 150 and widens as the body of the valve opener extends axially in the proximal direction. The two actuating elements 152 can extend from the transition section. The two actuating elements 152 can alternatively extend from the nose section 150 without a transition section. Some embodiments may utilize other shapes for the nose section 150, such as a cuboid, a rectangular, a conical, a pyramidal, a chamfered shape or the like.

In an example, the valve actuator or valve opener 122 has a lengthwise axis, the one or more actuating elements 152 extend axially or parallel to the lengthwise axis. In a particular example, two actuating elements 152 are diametrically opposed to one another along the lengthwise axis. In other examples, the two actuating elements can diverge from one another as they extend in the proximal direction. In still other examples, the two actuating elements can converge towards one another as they extend in the proximal direction. The spacing between the two plunger elements, whether straight, convergent, or divergent, can define the holding space between them. As shown, the two actuating elements 152 define an outer diameter having a dimension that is larger than the diameter of the nose section 150. For example, the diameter defined by the two actuator elements 152 at the proximal end is larger than the diameter defined by any part of the nose section 150, excluding the projections 154. In some examples, the diameter defined by the two actuator elements 152 is only larger than the actuating end at the nose section. In some examples, the nose section of the valve actuator is provided with a shaped contour, such as with distinct lines by forming recesses at the nose section with distinct contour lines or curves. One or more surfaces of the contoured nose section can then be used to press against the valve and the valve recoiling to push the contoured nose section in the proximal direction to return the valve actuator to a proximal position, as further discussed below.

In an example, the actuating elements 152 are flexible and deflectable so that when pushed by a male Luer tip, such as a syringe tip or a male Luer tip adaptor, the actuator elements 152 can defect or flex. The actuating elements 152 can be deflectable by selecting a material that has the requisite resilient properties. In other examples, the actuating elements 152 can be deflectable by incorporating one or more weakened sections, such as by incorporating a structurally thin section, by incorporating cut-outs, by employing a small cross-section compared to other sections of the same elongated actuating element, or combinations thereof. Alternatively, the actuating elements 152 can be flexible and deflectable by selecting a material that has the requisite resilient properties and by incorporating one or more weakened sections.

In still other examples, each actuating element 152 has more than one different cross-sectional profiles or contour along a length section. For example, an elongated plunger element can have a square profile located adjacent a crescent-shaped profile.

In an example, the actuating elements 152 are rigid and not deflectable or deformable when loaded, such as when pushed, by a male Luer tip. Further, one or more stabilizing elements 158 may be incorporated to increase the rigidity of the two actuating elements 152. The two actuator elements 152 may each include a cross-sectional profile, at least at a proximal end, that overlaps a push end of a male tip so that the male tip can push the valve actuator into the valve, as further discussed below. The stabilizing elements 158 can have proximal edges that are located distally of the proximal edges 182 (FIG. 4) of the actuator elements 152 or be flush with the proximal edges of the actuator elements.

The nose section 150 of the valve actuator 122 can be configured to engage the valve 120 to open the valve flaps and the slits formed therebetween when an axial force is applied by a male tip to the plunger elements or actuator elements 152 to move the valve actuator 122 into the valve to deflect the valve flaps, such as during insertion of an male Luer connector of an IV drip line or administration set. Generally, the nose section 150 of the valve opener is rigid relative to the more pliable valve 120, which allows the nose section 150, and more specifically the actuation end 180 (FIG. 7) of the nose section, to actuate the valve 120, such as to deflect the one or more flaps and open the one or more slits on the valve 120. The nose section 150 may be made of a non-compressible material, such as from a metal material, a rigid plastic, or a hard elastomer for pushing against and opening the valve.

The illustrated valve actuator embodiment 122 includes a pair of opposed bands or stabilizers 158 connecting the two actuating elements 152 at a location along the length of the actuating elements that are between the nose section 150 and the proximal end of the actuating elements. In some examples, the stabilizers 158 can be located at the proximal end of the two actuating elements 152 so that proximal edges of the stabilizers 158 are generally flush with the proximal end surfaces of the actuating elements 152. The two stabilizer elements or bands 158 can be referred to as a first or upper stabilizer element and a second or lower stabilizer element, elevation-wise.

In one embodiment, the stabilizers or stabilizer elements 158 have wall surfaces that are arc-shaped, forming an arc that generally follows the interior profile of the catheter hub 102 and connecting one actuating element 152 to another actuating element 152. The stabilizers or stabilizer elements 158 may form a substantially continuous cylindrical section on the body of the valve actuator, which body formed by the two stabilizer elements and the two actuating elements is spaced apart from the nose section 150 of the valve actuator 122. In other words, the valve actuator 122 can be elongated and can have sections that are continuous along a radial direction and sections with reliefs or through passages through the wall of the actuator that are not continuous along the radial direction.

In an example, the stabilizers 158 define a continuous body section along a perimeter or radial direction of the valve actuator that is spaced from a continuous body section of the nose section 150, which is also continuous along a perimeter or radial direction. The two stabilizers or stabilizer elements 158, also referred to as bands, may be joined together with the two plunger elements 152 to form a ring structure. Optionally, the two stabilizers 158 may be slightly offset and angled from each other in the axial direction, along the length of the valve actuator 122. In some embodiments, there may be one, three, or a different number of actuating elements 152 or stabilizers 158. For example, there can be two actuating elements 152 but only one stabilizer or band 158. In an example, the valve actuator 122, with the stabilizers or stabilizer elements 158 and projections 154, is made from plastic, such as by plastic injection molding.

The stabilizers 158 can help the valve actuator 122 remain centered within the catheter hub 102 while the actuator 122 moves, such as when pushed by a male Luer tip to open the slits of the valve. By staying centered, the nose section 150 can be better aligned with the valve disc 121 of the valve, such as with the slits on the valve disc, allowing for smooth actuation of the valve 120. The stabilizers 158 can also provide an engagement, via friction, with the interior of the catheter hub 102 to prevent the actuator 122 from sliding in the proximal direction following removal of the male Luer tip. However, as discussed above, projections 154 can be incorporated with the valve actuator 122 for cooperating with an internal shoulder or lip 176c inside the catheter hub 102 to retain the valve actuator 122 inside the catheter hub.

In one embodiment, the nose section 150 is configured to remain engaged to the valve disc 121 of the valve 120 following actuation of the valve and following removal of the male Luer tip. For example, the nose section 150 can wedge between the one or more slits on the valve disc and be held there by friction. Surface features, such as bumps, grooves, or barbs, can be provided on the valve actuator 122, such as on the nose section 150, to maintain the engagement between the actuator 122 and the valve 120 following actuation and following removal of the male Luer tip. Preferably, the valve actuator 122 does not engage the valve 120 following removal of the male Luer tip. Preferably the valve actuator can move from a distal position pushed against the valve to a proximal position spaced from or only minimally touching the valve but permitting the valve flaps to return or to close up the slits. When the valve opener returns to a proximal position after removal of the male Luer tip, the valve can close to prevent or limit fluid flow across the valve. The valve can open again by displacing the valve opener 122 in the distal direction with a male medical implement, such as a syringe tip or a tip of an administration set.

At least one relief, opening, or through passage 160 is provided between a transition section of the valve actuator 122 and the proximal end of the valve actuator. The transition section can be understood as the section proximal of the actuating distal end, or from the nose section until the two stabilizers. In an example, two reliefs or through passages 160 are incorporated to provide clearance so that the interior or central part of the valve actuator 122 and the interior surface of the catheter hub 102 can be in open communication. In other words, between the continuous section of the nose section and the continuous perimeter section defined by the two stabilizers 158 and the plunger elements 152, call a stabilizing ring 162, are one or two reliefs, through passages, or openings 160 for fluid flow such as flushing. The through openings or reliefs can also be utilized to retain the needle guard, as further discussed below.

The stabilizing ring 162 of the valve actuator 122 can have an inside diameter that is smaller than the diameter defined by the diagonal section or elbows of the two arms of the needle guard 130 when the two arms are biased outwardly by the side of the needle shaft in the ready to use position. Thus, during installation of the needle guard 130 into the holding space of the valve actuator, the diagonal section or elbows of needle guard 130 can deflect to pass through the stabilizing ring 162 and into the open areas defined by the reliefs or through openings 160.

When the tip protector 130 is positioned between the two plunger elements 152, the two distal walls of the needle guard 130, more specifically the two diagonal sections or elbows of the needle guard, can be located in the reliefs 160 as discussed above to engage the guard engagement surface on the interior surface of the catheter hub. This allows the needle guard 130 to project from the holding space of the valve actuator 122 through the two reliefs 160 to engage with the guard engagement surface of the catheter hub. The needle guard can therefore be retained within the interior of the catheter hub in the ready to use position and during retraction of the needle following successful venipuncture until the needle tip moves proximal of the two distal walls on the needle guard, at which time the needle guard can close over the needle tip, the distal end of the needle guard 130 becoming smaller in diameter than the inside diameter of the valve opener at the stabilizing ring 162 and be removed with the needle.

An undercut or recessed section can be provided in the interior cavity of the catheter hub 102 for accommodating the two diagonal sections or elbows of the needle guard. The needle guard 130 can therefore be prevented from sliding in the proximal direction during retraction of the needle following successful venipuncture by a shoulder of the recessed section or by some other surface feature on the interior of the catheter hub, such as a guard engagement surface on the interior of the catheter hub. Optionally or alternatively, the distal edge of one or both stabilizers 158 can provide the restraining surface to prevent the needle guard 130 from early activation during retraction of the needle, prior to the needle tip moving proximally of the two distal walls of the needle guard. In addition to a distal edge, each stabilizer 158 can have a proximal edge. When the needle guard 130 is retained by one or both distal edges of the stabilizers 158, the interior surface of the catheter hub 102 can omit engagement feature or features for accommodating the elbows of the needle guard. In an example, the needle guard 130 can engage with one or both distal edges of the two stabilizers 158 and can engage with engagement feature or features formed inside the catheter hub, such as a groove, lip or shoulder.

In some examples, one or both stabilizer elements 158 can have a slit or a channel, thus dividing the arc-shaped stabilizing or stabilizer element into two segments. Even with a slit on one or both stabilizer elements 158, the stabilizing ring 162, which can be a non-continuous ring, similar to a ring with one or more slots formed through the ring, can still provide the retaining structure to interact with the two elbows to prevent the needle guard 130 from early activation during retraction of the needle, prior to the needle tip moving proximally of the two distal walls.

The retaining surfaces of the stabilizer elements, such as the distal edges, can be referred to as a restrict point, choke gap, or choke point since they provide a rigid structure that prevents the needle guard from moving proximally thereof unless or until the needle guard first activates and collapses radially to reduce its radial profile to then slip proximally of the choke point. In an example, one or two elbows of the needle guard can be restricted by the choke point from moving in the proximal direction until the one or two elbows of the needle guard deflect to reduce the needle guard's radial profile. In an example, when the radial profile of the needle guard is reduced, the needle guard can slip through the bore defined by the stabilizing ring 162, from a distal position of the stabilizing ring to a proximal position of the stabilizing ring.

The valve opener 122 can be made from a metal material or from a plastic material. When made from a metal material, the valve opener 122 can be formed by bending or deep draw methods and the arc shape cross section of the actuating element 152 can provide added rigidity when pushed by the male Luer. Each actuating element 152 can comprise at least two lengthwise edges and a rib can be provided along one or both of the lengthwise edges to further add structural rigidity. One or more gaps can be provided between any two actuating elements 152. The gaps can provide clearance or space for fluid flow flowing thereacross, such as during flushing blood or IV infusion. The gap between the actuating elements 152 can define a holding space to accommodate a tip protector 130.

In some embodiments, a majority or most if not all of the tip protector 130 fits within a holding space formed by the body of the actuator 122, between the two plunger elements 152, in the ready to use position, as further discussed below. This allows the catheter hub 102 to be more compact, as less longitudinal space is needed within the hub to fit both the valve actuator 122 and the tip protector 130 serially lengthwise or when the two only partially overlap in the axial direction.

When the tip protector 130 only engages with the distal edge of the relief or through passage 160 in the actuator 122, then no deformity or change of diameter is required on the inside wall of the catheter hub and the tip protector 130 can be placed further proximally in the female Luer taper section while complying with the international Luer standard for conical fittings and the overall length of the catheter hub 102 can be further reduced.

The exemplary valve 120 shown in accordance with aspects of the present disclosure is usable with the catheter assemblies and hubs with a female Luer described herein. With reference to FIG. 3 and further reference to FIG. 4, which shows the catheter assembly or needle assembly 100 of FIGS. 1-3 along a lengthwise cross-section, the present valve 120 can have a first portion 168 having a first thickness and a second portion 170 having a second thickness less than the first thickness, measured orthogonal to a medial plane passing through the diameter of the valve. The second portion 170 with the second thickness can have a substantially constant thickness but can optionally include varying thicknesses along a cross-section of the valve, at the second portion.

In an example, the second portion 170 is formed by recessing the distally facing surface of the valve, the proximally facing surface of the valve, or both surfaces while the first portion 168 retain substantially the full width or thickness of the valve between the proximally and distally facing surfaces. In an example, the recesses at the second portion 170 can embody undercuts formed into the valve. As shown in FIG. 3, the surface appearance between the first and second portions 168, 170 can resemble a three-leaf clover. The three-leaf clover can be present on the distally facing surface, the proximally facing surface, or both surfaces of the valve 120. In other examples, the surface appearance of the proximally and/or distally facing surfaces can have varying contours so that the three-leaf clover can have contours of varying curves, lines, and edges. In an example, slits are formed through the thinner second portion 170 of the valve to form valve flaps between adjacent valves slits. In some examples, there can be two or more slits forming one or more valve flaps. For example, the first and second portions 168, 170 of the valve 120 can define a four-leaf clover, which can have four slits and four valve flaps. Preferably, the valve can have three slits and three valve flaps. The slits can start from approximately a central location of the valve and extend radially outwardly towards but short of the outer perimeter of the valve. The length of each slit can vary to form valve flaps of different sizes. The lengths of the slits can be selected to provide the desired valve flaps and valve flap deflection when pushed by a nose section 150 of a valve opener 122, such as when pushed by the actuation distal end of the valve opener 122.

The valve 120 may be integrally formed from a single material. Alternatively, the valve 120 may be formed of different materials in various portions of the valve 120 for reasons such as improved rigidity or flexibility. The valve can be made from a medical grade elastomer or a thermoplastic elastomer (TPE). These and other aspects of the valve 120 can be made in accordance to the valve examples disclosed in PCT Appl. No. PCT/EP2017/070934, published as PCT Pub. No. WO2018/033626 A1, the contents of which are expressly incorporated herein by reference as if set forth in full.

In the present embodiment, the securing device 124 is a retention ring, which has an annular wall structure having an exterior surface and an interior surface defining a bore. In other embodiments, the securing device for securing the valve inside the catheter hub can be a retaining skirt, O-ring or a spring. The valve 120, the valve opener or valve actuator 122, and the securing device 124 can vary in shapes, styles, and features but otherwise perform the noted functions described herein. The valve 120 can be a valve disc as described having at least one slit defining at least two flaps. As shown, the valve disc can have three (as shown) or more slits defining three or more flaps and the surface of the disc can have varying surface features and thicknesses along a cross-section of the valve disc. In other examples, the valve can have a valve disc and a skirt extending proximally of the proximally facing surface of the valve disc.

FIG. 4 shows a partial cross-sectional view of a catheter assembly or needle device 100, which can embody the catheter assembly of FIG. 3 in an assembled state. The catheter assembly 100 is shown without part of the needle 108, the catheter tube 104, and the needle hub 106, and without a vent plug typically located at the proximal opening of the needle hub. The catheter hub 102 is shown having a valve 120, a valve opener 122, a securing device 124, and a needle guard 130 located inside the interior cavity 123 of the hub body 126, which can be a single hub body with a distal end having a catheter tube extending therefrom and a proximal opening with a female Luer. As shown, the valve 120 is located distally of the securing device 124, part of the valve opener 122 is located in the bore of the securing device 124, and the needle guard 130 is located in the holding space 174 of the valve opener 122.

In an example, the interior of the catheter hub 102 is provided with one or more shoulders or ledges 176a, 176b, 176c, which can be understood as a structural lip or stop formed on the wall of the interior surface. The one or more shoulders, generically referred to as shoulder(s) 176, can provide engagement points or stop points for the components placed inside the interior cavity 123, to prevent the components from moving or dislodging from the interior of the catheter hub. As shown, the valve 120 can be placed in an annular groove and can abut one of the shoulders 176a to prevent proximal displacement of the valve 120. As shown, the valve 120 is also abutted to a shoulder 173 (FIG. 5) of the catheter hub 102 on the distal side of the valve to prevent distal displacement of the outer perimeter of the valve.

A securing device or retention ring 124 in the form of an annular ring is positioned adjacent the valve 120 and is abutted, at the securing device's proximal end, against another shoulder 176b inside the interior cavity 123 of the catheter hub to prevent proximal displacement of the securing device 124. As shown, the securing device 124 has a cross-section having a ramp shape, triangle shape, or slanted surface with the high part of the ramp at a distal location and tapers as it extends in the proximal direction. The securing device 124 may be made from a medical grade plastic material, such as by plastic injection. In other examples, the securing device may be made from a metal material, such as by stamping and then forging, pressing, or machining. In other examples, the securing device 124 may be made from an elastomeric material, such as an O-ring, to provide a proximally directed force to the valve opener when compressed, deformed, or biased between the valve opener nose section 150 and the inner wall of the catheter hub in the distal position.

The distal end of the securing device 124, the high part of the ramp, abuts the proximally facing surface of the valve 120 and the proximal end of the securing device 124, the narrow part of the ramp, abuts one of the shoulders 176b of the interior cavity 123. This arrangement of the securing device 124 can assist in holding the valve 120 from proximal displacement inside the catheter hub. In some examples, the valve 124 can be secured or supported inside the catheter hub by the securing device without also resorting to a separate shoulder 176 abutting the proximal edge of the valve. In an example, the securing device 124 can have a slight interference when first entering the proximal open end of the catheter hub and can have a size-on-size fit or a slight interference fit with the catheter hub in the final seated position shown. In still other examples, the securing device 124 can be retained within the interior of the catheter hub and can secure the valve 120 from proximal displacement with only interference fit with the catheter hub without a separate shoulder abutting the proximal end of the securing device.

The securing device can be a retention ring 124 having a generally triangular cross section as shown. In other examples, the cross section can have a different shape. As further discussed below, the retention ring 124, or securing device, can also function as a return mechanism for aiding the valve opener 122 to return or move from a distal position to a proximal position. For example, when the valve opener 122 is advanced by a male Luer tip to open the slits of the valve 120, the retention ring 124 can help to return the valve opener to a proximal position after removal of the male Luer tip from the proximal opening of the catheter hub. In some examples, the securing device 124 only secures the valve from proximal movement, while the elasticity of the valve returns the valve opener from a distal position to a proximal position. In some examples, the cross-section of the securing device can be chosen to be other than triangular in shape. In other examples, the shaped cross-section of the retention ring 124 can be formed as a retention skirt and be part of the valve. For example, the valve 120 can be formed with both the valve disc and the retention skirt, such as by integrating or unitarily forming.

In the example shown, the length of the valve opener 122 is selected so that the actuation end or actuating end 180 at the distal end of the nose section 150 just touches the valve disc of the valve and the proximal end edges 182 of the two plunger elements 152 just touch the nose section 184 of the needle hub 106. In other examples, the actuating end 180 can be slightly spaced away from the valve disc or slightly pressed against the valve disc but not materially deflect the valve flaps in order to allow the valve flaps to close the valve slits. Note that the valve flaps of the valve would slightly deflect in the distal direction due to the presence of the needle.

In an example, the holding space 174 of the valve opener 122 is sized and shaped to accommodate the needle guard 130. With reference to both FIGS. 4 and 5, which shows the needle device 100 of FIG. 4 rotated 90 degrees, the needle guard 130 is located between the two plunger elements 152 of the valve opener 122. The needle guard 130, which has a proximal wall 140 and two arms 188, 190 located distally of the proximal wall 140, is located in the holding space 174 of the valve opener 122 with two elbows 188a, 190a of the needle guard 130 located distally of the two stabilizing elements 158. The elbows are located between the distal walls 188b, 190b and the elongated arm portions of the arms. If the needle 108 is retracted in the proximal direction, the two elbow 188a, 190a will be stopped from moving proximally past the two distal edges 158a, 158a of the two stabilizing elements 158, which act as a choke point. As previously described, the radial dimension of the needle guard at the two elbows 188a, 190a is larger than the inside dimension of the stabilizing ring 162 and is therefore physically stopped by the distal edges of the two stabilizer elements 158. Following successful venipuncture, the needle is removed from the catheter tube and the catheter hub and the needle tip moves proximally of the two distal walls 188b, 190b of the needle guard, which then allows the two arms 188, 190 of the needle guard to move inwardly or collapse to decrease the radial dimension at the two elbows. Approximately at the same time, the change in profile 142 (FIG. 2) near the needle tip abuts the perimeter defining the opening 192 on the proximal wall 140 of the needle guard and further retraction of the needle causes the needle guard 130 to be removed with the needle 108.

In an example, the interior of the catheter hub 102 is enlarged at a location proximate the two elbows 188a, 190a. For example, the inside diameter of the catheter hub at the two elbows is larger than the inside diameter of the catheter hub at the proximal wall 140 of the catheter hub. This space can be incorporated to provide relief or added space for the needle guard in the ready position. That is, the relief, when incorporated, provides space for the two arms 188, 190 so that the two arms are not compressed or biased inwardly at the two elbows 188a, 190a in the ready to use position to the same extent compared to when no relief is provided. This can reduce drag between the needle shaft and the two curved ends at the ends of the two distal walls 188b, 190b during retraction of the needle following needle puncture.

With reference again to FIG. 4, the valve opener 122 can be retained in the interior cavity 123 of the catheter hub 102 and restricted from displacing out of the proximal opening 136 by providing at least one side projection 154 on the valve opener to interact with one of the shoulders 176 inside the interior cavity 123. The cross-sectional dimension of the valve opener at the at least one projection 154 is larger than the cross-sectional dimension at the shoulder of the catheter hub 102, thereby presenting a physical stop to prevent proximal displacement of the valve opener 122 out of the proximal opening 136 of the catheter hub. As shown, if the valve opener 122 moves in the proximal direction, such as due to the elbows 188a, 190a of the needle guard pushing in the proximal direction against the distal edges 158a of the two stabilizing elements 158 during retraction of the needle but before the needle tip moves proximally of the two distal walls, the total proximal movement can be restricted by the projection 154 hitting against the shoulder 176c. In an example, two projections 154 can be provided on the valve opener 122, one on each actuating element 158, to interact with the shoulder 176c, which can be annular in configuration.

FIG. 6 is a cross-sectional side view of the needle assembly 100 of FIGS. 4 and 5 with the needle 108, needle guard 130 and the needle hub 106 removed from the catheter tube 104 and the catheter hub 102, such as following successful venipuncture and the catheter tube 104 being located inside a vein of a patient. As shown, the needle guard 130 has been removed with the needle 108 in the manner discussed hereinabove. Following removal of the needle 108, the plurality of valve flaps 194 are permitted to recoil or return to a relaxed state to close the slits 196 and restrict flow in the proximal and distal directions through the valve 120. In the state shown, the actuating end 180 at the nose section 150 of the valve actuator 122 is located within the bore defined by the securing device 124, but spaced from or not contacting the securing device 124. The tapered surface of the nose section 150 is also spaced from the securing device 124. This spacing or gap allows the valve actuating element 122 to move forward in the distal direction, when pushed by a male Luer tip, before hitting or contacting the securing device 124. In some examples, the male Luer tip abuts the female Luer of the catheter hub to stop further distal advancement of the male Luer tip into the catheter hub before the nose section 150 of the valve actuator contacts or presses against the inside of the securing device 124. The actuating end 180 is shown in contact with the proximally facing surface of the valve 120. In other examples, the actuating end 180 can be spaced from the proximally facing surface of the valve 120. The actuating end 180 can be spaced from the valve a distance that is approximately the same as the gap between the projections 154 on the valve opener 122 and the shoulder inside the catheter hub 102.

As shown, the nose section 150 of the valve opener 122 has an increasing taper in the proximal direction, which is spaced from the tapered surface of the ramp cross-section 198 of the securing device 124. The size and shape of the nose section 150 can be arranged to contact the ramp cross-section 198 of the securing device 124 or spaced from the ramp cross-section. In an example, the nose section 150 can incorporate a resilient section or band, such as an elastomeric band, strip, or strips, and can create a slight interference as the valve opener 122 is advanced in the distal direction to open the valve 120 and the nose section abutting the securing device, as further discussed below with reference to FIG. 7. If the lengthwise axis of the catheter hub 102 is considered an X-axis and the Y-axis is orthogonal to the X-axis, the shape of the nose section 150 is selected to both deflect the valve flaps 194 in the distal direction as well to generate force vectors that have both an X component and a Y component. The force vectors acting in the X direction, an X component force vector or proximally directed force vector, can be utilized to facilitate the return of the valve opener 102 from a distal position, where the actuating end 180 is pushed into the valve 120 to deflect the valve flaps 194, to a proximal position as shown. As further discussed below, the valve flaps of the valve 120 or both the valve flaps of the valve and the securing device 124 can generate force vectors against the nose section 150 of the valve opener 122 to return the valve opener from a distal position to a proximal position. In still yet other examples, other part or parts of the valve, aside from the valve flaps, can exert a proximally directed force to move the valve from a distal position to a proximal position.

In an example, the area or section inside the catheter hub 102 adjacent the open proximal end 136 is a female Luer 204, which is understood to have a structure formed in accordance with the ISO Standards for female Luers. The proximal edges 182 of the two plunger element 152, 152 of the valve opener 122 are shown recessed from the proximal open end 136 but are located within the female Luer 204. Thus, when a male Luer tip is inserted into the female Luer, the male Luer tip will push the two plunger elements 152 in the distal direction to cause the valve opener 122 to push into the valve 120 to open the valve, as further discussed below.

FIG. 7 is a cross-sectional side view of the assembly of FIG. 6 with a male Luer tip 200 inserted into the open proximal end 136 and advancing the valve opener 122 into the valve 120 to open the valve flaps 194 and open fluid communication between the male Luer tip 200 and the lumen of the catheter tube 104. In practice, the male Luer tip 200 can be a syringe tip or a male tip of an IV drip line or administration set that is attached to an IV bag. In the FIG. 7 configuration, fluids can be withdrawn or aspirated out the catheter hub 102 in the proximal direction or infused through the catheter tube in the distal direction. Although not shown, the male Luer tip 200 can have a threaded collar for engaging the lugs or external threads 202 on the catheter hub 102 to further maintain the valve actuator 122 in the distal position to open the valve 120.

In an example, the valve opener 122 is configured to move distally when advanced by the male Luer tip 200. The amount or distance that the valve opener 122 moves in the distal direction should be sufficient to allow the actuating end 180 and the nose section 150 to deflect the valve flaps 194 in the distal direction to open the slits of the valve 120 to then open up fluid communication between the male Luer tip 200 and the catheter tube 104. In the example shown, the actuating end 180 of the valve opener 122 moves distal of the valve flaps and the valve flaps are compressed between the interior of the catheter hub 102 and the tapered surface of the nose section 150, or the valve flaps are deflected or deformed in the distal direction by the nose section of the valve opener with or without compression. In other examples, the actuating end 180 moves a distance that is equal to the ends of the valve flaps 194 or short of the ends of the valve flaps, never-the-less still opening the valve flaps to allow free flow in both proximal and distal directions.

Upon withdrawal of the male Luer tip 200, such as when replacing an IV fluid bag attached to the male Luer tip 200, the distally directed force acting on the proximal edges 182 of the two plunger elements 152 by the male Luer tip 200 is removed or ceased and the female Luer 204 is unoccupied by any external object. This allows for the valve opener 122 to return to its proximal position, now vacated by the male Luer tip. In an example, the elasticity of the valve 120 allows the valve flaps 194 to recoil to their more relaxed state, such as to move to the position shown in FIG. 6. This recoiling action of the valve flaps 194 and the shape of the nose section 150 of the valve opener 122 allow the valve flaps to impart force vectors on the nose section 150 to cause the valve opener 122 to move from the distal position shown in FIG. 7 to a proximal position, as shown in FIG. 6. The force vectors generated by each of the valve flaps 194 on the nose section 150 of the valve opener 122 when the valve flaps recoil include a force component that is generally parallel to the lengthwise axis of the catheter hub, also referred to herein as the X-component force vector or proximally directed force vector. Thus, the X-component force vector generated by the valve flaps can cause the valve opener 122 to move from a distal position, where the actuating end 180 and the nose section 150 deflect the valve flaps of the valve in the distal direction to open the valve, to a proximal position, where the actuating end and the nose section no longer deflect the valve flaps. In some examples, the nose section 150 of the valve actuator 122 is provided with a shaped contour, such as with distinct lines or curves by forming recesses at the nose section with distinct contour lines or curves. One or more surfaces of the contoured nose section can then be used to press against the valve 120. The valve can be pressed to generate multiple compression points or biased points. For example, the contoured nose section can be structured to compress the valve flaps, or the valve opener can deflect the valve flaps in the distal direction, so that the valve flaps can in turn generate force vectors against the nose section as the male Luer tip is removed and the valve flaps allowed to return to their relaxed state. The contoured nose section can also axially compress, deform, or bias part or parts of the valve against a distal shoulder so that the valve imparts an opposite axially returning force when the male Luer tip is removed, as further discussed below, such as with reference to FIGS. 31-32B. The valve alone can therefore push the valve opener in the proximal direction upon removal of the male Luer tip when the valve recoils from being compressed, deformed, biased, or deflected by the contoured nose section alone or by multiple points sections of the contoured nose section.

In some examples, the interference between the ramp cross-section 198 of the securing device 124 and the nose section 150 produces force vectors on the nose section 150 of the valve opener 122, which include an X-component force vector. For example, the valve opener can incorporate an elastic band or one or more elastic strips to be compressed or biased by the securing device as the nose section is advanced by the male Luer tip into the securing device. Thus, in addition to return forces generated by the valve flaps of the valve 120 on the nose section 150 of the valve opener 122, the interference between the securing device 124 and the nose section 150 of the valve opener generates a return force and contributes to the proximal movement of the valve opener 122 from a distal position, where the actuating end and the nose section deflect the valve flaps of the valve in the distal direction, to a proximal position, where the actuating end and nose section no longer deflect the valve flaps. In the proximal position, the valve opener 122 is situated inside the catheter hub in the manner generally represented by FIG. 6, which shows the valve flaps generally closing off the slits so as to stop or restrict fluid flow in the proximal direction and/or the distal direction. In some examples, the nose section can be provided with a recess and an elastomeric strip or band is placed in the recess to create a valve opener with a rigid section and a more pliable section. In other examples, the nose section is co-molded or insert-molded with the elastomeric strip or band. The elastomeric strip or band incorporated with the nose section can allow the valve actuator to be pressed against a rigid part or component of the securing device to generate a return force following removal of the male Luer tip.

Aspects of the invention are therefore understood to include a catheter assembly or needle device comprising a catheter hub having a catheter tube extending in a distal direction, said catheter hub comprising a body having an exterior surface and an interior surface defining an interior cavity. A valve and a valve opener can be located inside the interior cavity. In an example, a securing device having a body defining a bore is located proximal of the valve. The valve flaps of the valve can impart a proximally directed return force to return the valve opener from a distal position to a proximal position. Additionally or alternatively, a valve can be compressed or biased axially against a distal shoulder and the valve providing an axially directed force against the nose section to return the valve opener, upon removal of the male Luer tip. In an example, the securing device can provide an interference with the valve opener, such as an elastomeric part of the valve opener, when the valve opener is advanced in the distal direction by a male Luer tip to open the valve flaps of the valve and wherein the interference can provide force vectors that include a force vector that extends generally parallel to the lengthwise axis of the catheter hub to return the valve opener from a distal position to a proximal position, when the male Luer tip is removed from the catheter hub. In other examples, the nose section is spaced from the securing device or does not abut the securing device and the return force is provided by the valve only. The securing device can additionally provide a securing function for securing the valve inside the catheter hub and preventing the valve from inadvertent proximal displacement to dislodge from the catheter hub. The catheter hub can include a needle projecting through the catheter hub, the valve, the valve opener, the securing device and the catheter tube. The needle can attach to a needle hub at the needle's proximal end.

Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of the valve opener into the valve to deflect the valve flaps and movement away from the valve.

With reference now to FIGS. 8 and 9, a catheter assembly or needle assembly 100 provided in accordance with further aspects of the invention is shown, shown with the needle and needle hub removed but can have the same needle and needle hub as described elsewhere herein. The needle assembly 100 can also incorporate a needle guard as described elsewhere herein.

In the present embodiment, the catheter hub 102, catheter tube 104, valve 120, valve opener 122, and securing device 124 can be similar to those shown with reference to FIGS. 6 and 7 with a few exceptions. In the present embodiment, an annular slit or annular channel 206 is provided on the proximally facing surface of the valve 120. As shown, the annular slit 206 is recessed from the outer perimeter of the valve. The annular slit 206 can be provided at the first portion 168 (FIG. 3) of the valve, which is the thicker part of the valve that is thicker than the second portion 170 of the valve. The annular slit 206 can be provided to receive a distal end of a securing device 124, as further discussed below.

In the present embodiment, the securing device 124 is a retention ring having a distal end 210 that projects into the annular slit 206. In an example, the distal end 210 of the securing device 124 is forced into the annular slit 206 and held therein by compression or interference. In other examples, the securing device could be held within the annular slit 206 using adhesive or bonding. In still other examples, the annular slit 206 is an annular channel and does not grip the securing device on both the interior and exterior surfaces of the securing device. For example, the exterior surface of the securing device 124 can press against the annular channel but is spaced from the annular channel on the interior surface of the securing device. This alternative configuration allows the securing device 124 to press the valve 120 outwardly against the catheter hub without also requiring the annular slit to grip both interior and exterior surfaces of the distal end of the securing device.

The retention ring 124 of the present embodiment can have a wall with a length between the proximal and distal ends and with a generally constant wall thickness curved body section at the proximal end of the retention ring. The wall has an interior that defines a bore for accommodating the nose section 150 of the valve opener 122. The wall of the securing device 124 can be generally cylindrical except for the proximal end. In an example, the proximal end 212 of the retention ring 124 can have an outwardly curved lip 214 for securing the retention ring 124 against an internal shoulder 176b of the catheter hub 102. Once located against the internal shoulder 176b, the securing device 124 can help to secure the valve 120 from displacing in the proximal direction. The valve 120 is secured or supported from distal movement by being located against a shoulder 173 (FIG. 5) of the catheter hub 102 on the distally facing surface of the valve.

The securing device 124 and the nose section 150 of the valve opener 122 are spaced from one another in the valve opener proximal position of FIG. 8. The gap or spacing between the two provides clearance for the valve opener 122 to move in the distal direction to open the valve, such as to deflect the valve flaps, before contacting or hitting the securing device 124. In the state shown, the actuating end 180 at the nose section 150 of the valve actuator 122 is located within the bore defined by the securing device 124, but spaced from or not contacting the securing device. The tapered surface of the nose section is also spaced from the securing device. This spacing or gap allows the valve actuating element to move forward in the distal direction before hitting or contacting the securing device. The actuating end 180 is shown in contact with the proximally facing surface of the valve 120. In other examples, the actuating end can be slightly spaced from the proximally facing surface of the valve.

FIG. 9 is a cross-sectional side view of the assembly of FIG. 8 with a male Luer tip 200 inserted into the open proximal end 136 and advancing the valve opener 122 into the valve 120 to open the valve flaps 194 and open fluid communication between the male Luer tip 200 and the lumen of the catheter tube 104, similar to the embodiment of FIG. 7. Although not shown, the male Luer tip 200 can have a threaded collar for engaging the lugs or external threads 202 on the catheter hub 102 to further maintain the valve actuator 122 in the distal position to open the valve 120.

In an example, the valve opener 122 is configured to move distally when advanced by a male Luer tip 200. The amount or distance that the valve opener moves in the distal direction should be sufficient to allow the actuating end 180 and the nose section 150 to deflect the valve flaps 194 in the distal direction to open the slits to then open fluid communication between the male Luer tip 200 and the catheter tube 104. In the example shown, the actuating end 180 of the valve opener 122 moves distal of the valve flaps and the valve flaps are compressed between the interior of the catheter hub 102 and the tapered surface of the nose section 150, or the valve flaps are deflected or deformed in the distal direction by the nose section of the valve opener with or without compression. As shown, the actuating end 180 moves a distance that is equal to the ends of the valve flaps 194 or short of the ends of the valve flaps but still opening the valve sufficiently for free flow in both directions.

In the example shown, the curved lip 214 acts like a biasing member. Thus, when the nose section 150 is pressed against the curved lip 214 at the proximal end of the securing device, the curved lip 214 presses against the nose section, such as against an elastomeric band, strip or section incorporated at the nose section, and imparts a pair of component forces or force vectors on the nose section 150 of the valve opener, which includes a force that acts generally parallel to the lengthwise axis of the catheter hub 102. In other examples, the nose section is spaced from the securing device when the male Luer tip abuts the female Luer of the catheter hub. The valve under that scenario can provide the return force needed to return the valve opener from a distal position to a proximal position.

Upon withdrawal of the male Luer tip 200, such as when replacing an IV fluid bag attached to the male Luer tip 200, the distally directed force acting on the proximal edges 182 of the two plunger elements 152 by the male Luer tip 200 is removed or ceased and the female Luer 204 is unoccupied by an external object. This allows for the valve opener 122 to return to its proximal position, now vacated by the male Luer tip. In an example, the elasticity of the valve 120 allows the valve flaps 194 to recoil to their more relaxed state, such as to move to the position shown in FIG. 8. This recoiling action of the valve flaps 194 and the shape of the nose section 150 of the valve opener allow the valve flaps to impart force vectors on the nose section 150 to cause the valve opener 122 to move from the distal position shown in FIG. 9 to a proximal position, generally as shown in FIG. 8.

Aspects of the invention is therefore understood to include a catheter assembly or needle device comprising a catheter hub having a catheter tube extending in a distal direction, said catheter hub comprising a body having an exterior surface and an interior surface defining an interior cavity. A valve and a valve opener can be located inside the interior cavity. In an example, a securing device having a body defining a bore is located proximal of the valve and secures the valve inside the catheter hub. In an example, the securing device provides an interference with the valve opener when the valve opener is advanced in the distal direction by a male Luer tip. In another example, the male Luer tip abuts the female Luer of the catheter hub before the nose section of the valve opener contacts the securing device. The valve opener is configured to open the valve flaps of the valve. In an example, the interference, deflection, bias, or compression by the valve opener to the valve flaps generate stored energy that provides force vectors that include a force vector that extends generally parallel to the lengthwise axis of the catheter hub to return the valve opener from a distal position to a proximal position, when the male Luer tip is removed from the catheter hub. The securing device can also impart a return force to the nose section, such as to the area of the nose section with a pliable insert, elastic band or material, of the valve opener to provide an additional proximally directed return force. The securing device can additionally provide a securing function for securing the valve inside the catheter hub and preventing the valve from inadvertent proximal displacement to dislodge from the catheter hub. The catheter hub can include a needle projecting through the catheter hub, the valve, the valve opener, the securing device and the catheter tube. The needle can attach to a needle hub at the needle's proximal end.

Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of a valve actuator into the valve to deflect the valve flaps and movement away from the valve.

Figure 10:
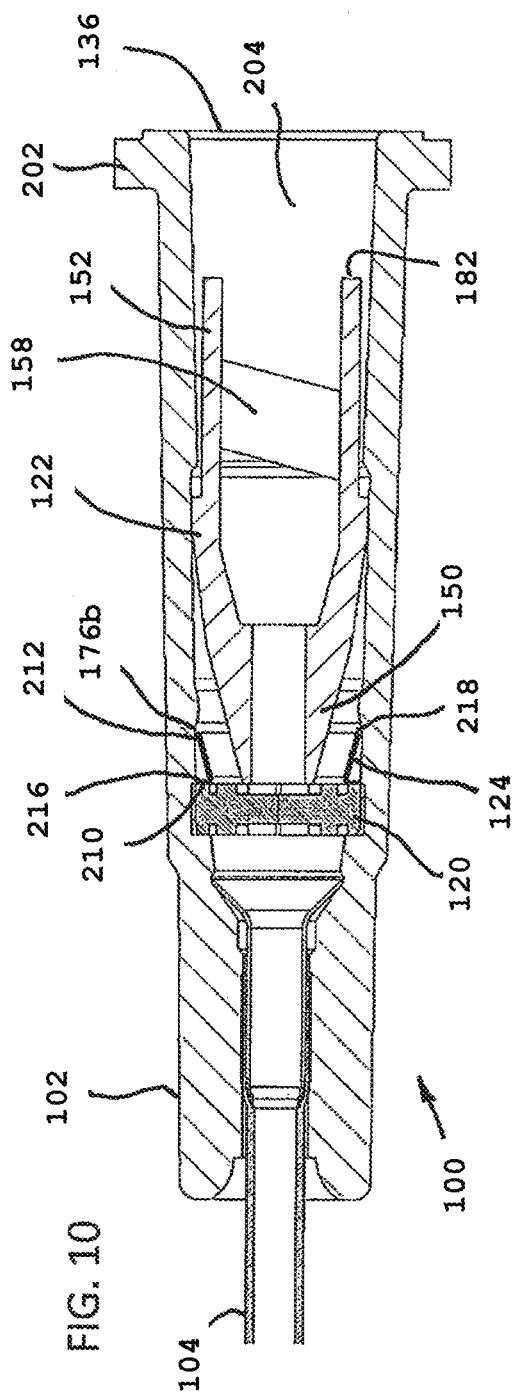
FIG. 10 is a cross-sectional side view of another embodiment of a catheter assembly or needle device with the needle and needle hub removed, such as following successful venipuncture and with the valve opener in its proximal position.
Figure 11:
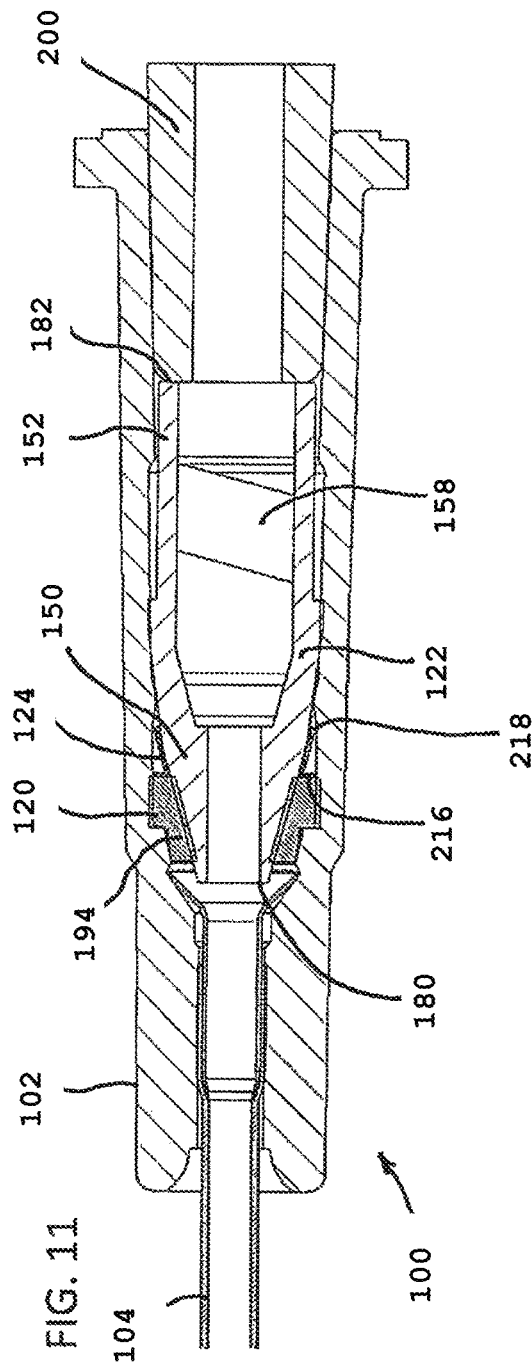
FIG. 11 is a cross-sectional side view of the assembly of FIG. 10 with the valve opener in its distal position and opening the valve.

With reference now to FIGS. 10 and 11, a catheter assembly or needle assembly 100 provided in accordance with further aspects of the invention is shown with the needle and needle hub removed but can have the same needle and needle hub as described elsewhere herein. The needle assembly 100 can also incorporate a needle guard 130 as described elsewhere herein.

In the present embodiment, the catheter hub 102, catheter tube 104, valve 120, valve opener 122, and securing device 124 can be similar to those shown with reference to FIGS. 6-9 with a few exceptions. In the present embodiment, the securing device 124 is a retention ring having a distal end 210 with an outward curved lip forming a flange 216 for abutting or contacting the proximally facing surface of the valve 120 and a wall or body that tapers from a first dimension to a second larger dimension in the proximal direction. Thus, the wall of the present embodiment resembles a ramp with a high part of the ramp at a distal location and tapers as it extends in the proximal direction.

The present securing device 124 has a ramp or a slanted surface similar to that of FIGS. 6 and 7 but without the same solid cross-section.

The proximal end 212 of the securing device comprises a proximal edge 218 that can be dimensioned to abut or press against an internal shoulder 176b of the catheter hub 102. Once located against the internal shoulder 176b, the securing device 124 can help to secure the valve from displacing in the proximal direction. Alternatively, there does not need to be a shoulder to secure the securing device 124 within the interior if there is a slight interference fit between the proximal end 212, and/or distal end of the securing device, and the inside diameter of the catheter hub 102. The valve 120 is secured or supported from distal movement by being located against a shoulder 173 (FIG. 5) on the distally facing surface of the valve.

The securing device 124 and the nose section 150 of the valve opener 122 are spaced from one another in the valve opener proximal position of FIG. 10. The gap or spacing between the two provides clearance for the valve opener 122 to move in the distal direction to open the valve, such as to deflect the valve flaps, before closing the gap, contacting or hitting the securing device 124. In the state shown, the actuating end 180 at the nose section 150 of the valve actuator 122 is located within the bore defined by the securing device 124, but spaced from or not contacting the securing device. The tapered surface of the nose section is also spaced from the securing device. This spacing or gap allows the valve actuating element 122 to move forward in the distal direction before hitting or contacting the securing device 124. The actuating end 180 of the valve actuator is shown in contact with the proximally facing surface of the valve 120. In other examples, the actuating end can be slightly spaced from the proximally facing surface of the valve.

FIG. 11 is a cross-sectional side view of the assembly of FIG. 10 with a male Luer tip 200 inserted into the open proximal end 136 and advancing the valve opener 122 into the valve 120 to open the valve flaps 194 and open fluid communication between the male Luer tip 200 and the lumen of the catheter tube 104, similar to the embodiment of FIGS. 7 and 9. Although not shown, the male Luer tip 200 can have a threaded collar for engaging the lugs or external threads 202 on the catheter hub to maintain the valve actuator in the distal position to open the valve.

In an example, the valve opener 122 is configured to move distally when advanced by the male Luer tip 200. The amount or distance that the valve opener moves in the distal direction should be sufficient to allow the actuating end 180 and the nose section to deflect the valve flaps 194 in the distal direction to open the slits to then open fluid communication between the male Luer tip 200 and the catheter tube 104. In the example shown, the actuating end 180 of the valve opener 122 moves distal of the valve flaps and the valve flaps are compressed between the interior of the catheter hub and the tapered surface of the nose section 150, or the valve flaps are deflected or deformed in the distal direction by the nose section of the valve opener with or without compression. In some examples, the nose section of the valve actuator is provided with a shaped contour, such as with distinct lines by forming recesses at the nose section with distinct contour lines or curves. One or more surfaces of the contoured nose section can then be used to press against the valve and the valve recoiling to push the contoured nose section in the proximal direction to return the valve actuator to a proximal position. For example, one or more of the contoured surfaces can axially compress, deform, or bias the valve against a distal shoulder so that the valve provides an axially directed return force upon removal of the male Luer tip. In some examples, the actuating end 180 moves a distance that is equal to the ends of the valve flaps 194 or short of the ends of the valve flaps, but still opening the valve sufficiently for free flow in both directions.

In the example shown, the ramp acts like a biasing member. For example, when the nose section 150 is pushed against the ramp structure of the securing device 124 by the male Luer tip, the securing device exerts an opposite biasing force against the nose section 150 of the actuator, such as against a pliable section located at the nose section. Thus, when the nose section 150 is pressed against the ramp in an interference, the ramp of the securing device 124 imparts a pair of component forces or force vectors on the nose section, which includes a force that acts generally parallel to the lengthwise axis of the catheter hub. In some examples, the nose section is spaced from the securing device when the male Luer tip abuts the female Luer of the catheter hub.

Upon withdrawal of the male Luer tip 200, such as when replacing an IV fluid bag attached to the male Luer tip 200, the distally directed force acting on the proximal edges 182 of the two plunger elements 152 by the male Luer tip 200 is removed or ceased and the female Luer 204 is unoccupied by any external object. This allows for the valve opener 122 to return to its proximal position, now vacated by the male Luer tip. In an example, the elasticity of the valve 120 allows the valve flaps 194 to recoil to their more relaxed state, such as to move to the position shown in FIG. 10. This recoiling action of the valve flaps 194 and the shape of the nose section 150 of the valve opener allow the valve flaps to impart force vectors on the nose section 150 to cause the valve opener 122 to move from the distal position shown in FIG. 11 to a proximal position, generally as shown in FIG. 10. Additionally, and as discussed above, the ramp structure of the securing device 124 exerts a returning force against the nose section, such as to a pliable section located at the nose section, to move the valve opener 122 in the proximal direction to return the valve opener essentially to the position shown in FIG. 10.

Aspects of the invention is therefore understood to include a catheter assembly or needle device comprising a catheter hub having a catheter tube extending in a distal direction, a needle attached to a needle hub and the needle extending through the catheter hub and the catheter tube. The catheter hub comprising a body having an exterior surface and an interior surface defining an interior cavity. A valve and a valve opener can be located inside the interior cavity. In an example, a securing device having a body defining a bore is located proximal of the valve and secures the valve in the catheter hub. The securing device can provide an interference with the valve opener when the valve opener is advanced in the distal direction by a male Luer tip to open the valve flaps of the valve and wherein the interference fit provides force vectors that include a vector that extends generally parallel to the lengthwise axis of the catheter hub to return the valve opener from a distal position to a proximal position, when the male Luer tip is removed from the catheter hub. The securing device can additionally provide a securing function for securing the valve inside the catheter hub and preventing the valve from inadvertent proximal displacement to dislodge from the catheter hub and not provide any return force to the valve opener.

Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of a valve actuator into the valve to deflect the valve flaps and movement away from the valve.

FIG. 12, FIG. 13, and FIG. 14 show side cross-sectional views, front views, and isometric views of three different securing devices 124, which can embody retention rings. These retention rings 124 can be used with catheter assemblies described elsewhere herein. FIG. 13 also shows a valve 120 with the retention ring 124. With reference initially to the retention ring or securing device 124 of FIG. 12, the retention ring has a ring body 220 with a first end or distal end 210 and a second end or proximal end 212. The ring body 220 has a generally constant outside dimension along the length of the ring body, which is generally cylindrical. Internally, the ring body 220 has a smaller inside diameter at the distal end than the inside diameter at the proximal end and a wall thickness that decreases in dimension from a distal end to a proximal end. The inside surface of the ring body 220 defines a bore and wherein the bore is configured to accommodate a valve opener and compress or bias the nose section of the valve opener to impart a pair of component forces, as previously discussed. In another example, the securing device is sized and shaped to be spaced from the nose section when the male Luer tip abuts the female Luer of the catheter hub. In an example, the securing device 124 is formed from a medical grade plastic material. In other examples, the securing device can be formed from a medical grade elastomeric material or a thermoplastic elastomer material (TPE). The securing device may alternatively be made from a metal material, such as by stamping and bending or machining.

As shown in FIG. 12, the cross-section of the ring body 220 has a ramp shape or a slanted surface on the interior surface of the ring body. Further, the slanted surface has a constant slope. In other examples, the slope of the slanted surface is not constant. For example, there can be one or more bumps or inflection points to produce a contour that is not straight. The contour, whether with a constant slope or not, can be selected to generate a compression, bias or interference with the nose section of a valve opener 122, such as to pliable section or sections of the nose section, when the valve opener is pushed against the securing device 124. The compression, bias or interference fit with the valve opener 122 is configured to generate force vectors, which include a force that is generally parallel to the lengthwise axis of the valve opener. This in turn helps the valve opener to move from a distal position to a proximal position. The securing device 124 of FIG. 12 is similar to the securing device 124 shown in FIGS. 4-7.

FIG. 13 shows a valve 120 and a securing device 124. The securing device 124 can be similar to the securing device described with reference to FIGS. 8 and 9 and the valve 120 can be similar to valves described elsewhere herein, such as with reference to FIGS. 3-7. As shown in the different views of FIG. 13, the valve 120 has a valve body 224 with an outer perimeter 226, a proximally facing surface 228, and a distally facing surface 230. The proximally facing surface 228, the distally facing surface 230, or both surfaces 228, 230 have a first valve portion 168 and a second valve portion 170, as previously discussed.

The first and second valve portions 168, 170 define regions or sections of different thicknesses. Further, the two regions can be shaped to form contours for where to incorporate slits 234 to form valve flaps 194. As shown, the valve 120 has three slits 234 that converge to a central point and extend outwardly toward the outer perimeter 226, but short of the outer perimeter. In an example, the slits 234 are formed through the thinner second portion 170 of the valve body 224 only. In some examples, there can be more or less than three slits forming more or less than three valve flaps.

As previously discussed, the proximally facing surface 228 has an annular slit or annular slot 206 for receiving the distal end 210 of the securing device 214. In some example, the annular slot is an annular channel with a gap that does not grip both interior and exterior surfaces of the distal end of the securing device. The securing device 124 can be made from a thin-walled cylinder, such as from a metal material or from a plastic material, and wherein the proximal end 212 is curved outwardly to terminate in a curved lip 214, similar to a radiused corner. The inside surface of the ring body 220 of the securing device 124 defines a bore and wherein the bore is configured to accommodate a valve opener and compress or bias the nose section 150 of the valve opener 122, such as to pliable section or sections of the nose section, to impart a pair of component forces, as previously discussed. More particularly, the radiused corner of the curved lip 214 is configured to compress or bias the nose section of the actuator and impart a pair of component forces. In another example, the securing device is sized and shaped to be spaced from the nose section when the male Luer tip abuts the female Luer of the catheter hub. As shown, the curved lip 214 has an outside diameter and wherein the outside diameter of the curved lip is smaller than the outside diameter of the valve 120. Depending upon the structure of the interior of the catheter hub, the size of the curved lip 214 can be adjusted so that when installed inside the catheter hub, the curved lip abuts or contacts a shoulder to secure the retaining ring within the interior cavity of the catheter hub.

FIG. 14 shows a securing device 124 that is similar to the securing device described with reference to FIGS. 10 and 11. As shown, the ring body 220 has a distal end 210 with a curved lip defining a flange 216, which has a generally planar wall surface for abutting a surface of a valve. The ring body 220 of the securing device has a generally constant wall thickness that tapers outwardly from a first diameter at the distal end, just proximal of the flange 216, to a second larger diameter at the proximal end 212, which has a proximal edge 218 for abutting or contacting a shoulder inside a catheter hub 102 to retain the securing device 214 within the catheter hub. The wall surface has a slanted surface that resembles a ramp. The inside surface of the ring body 220 of the securing device 124 defines a bore and wherein the bore is configured to accommodate a valve opener and compress or bias the nose section of the valve opener, such as to a section or sections of the nose section that incorporate an elastomeric strip, band or material, to impart a pair of component forces, as previously discussed. In another example, the securing device is sized and shaped to be spaced from the nose section when the male Luer tip abuts the female Luer of the catheter hub.

Figure 15:
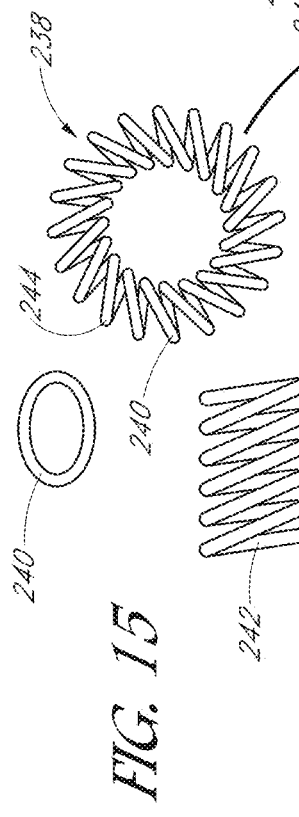
FIG. 15 shows different views of a securing device in the form of a spring.

FIG. 15 shows different views of a canted coil spring 238, which has a plurality of interconnected coils 240 that are all canted generally along the same direction. The spring 238 can be made from a metal material. FIG. 15 shows a canted coil spring 238 in a length 242 configuration, a canted coil spring in a ring 244 configuration with two ends of the spring length connected, and a side view of a single canted coil 240, which is generally elliptical in shape. Canted coil springs are well known in the spring art and the coils of the canted coil spring are understood to be deflectable or compressible in the radial direction relative to the ring centerline, which is understood to project in and out of the page at the center of the spring ring 244.

Figure 16:
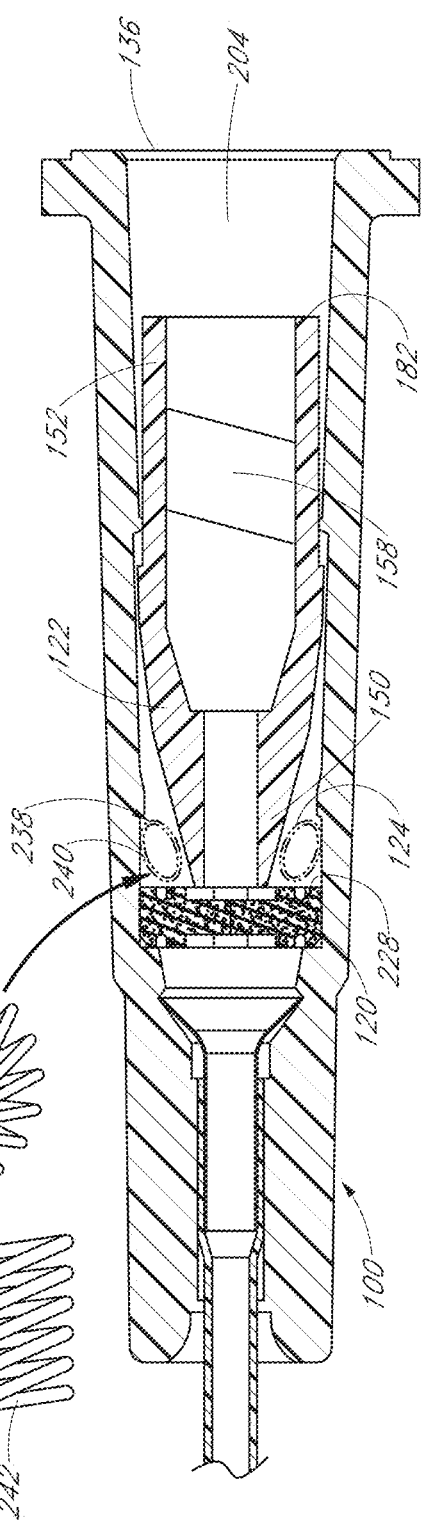
FIG. 16 is a cross-sectional side view of another embodiment of a catheter assembly or needle device with the needle and needle hub removed and with the securing device of FIG. 15.

With reference now to FIG. 16 in addition to FIG. 15, the catheter assembly 100 of the present embodiment is shown, which is similar to the catheter assemblies of FIGS. 4-11 with a few exceptions. In the present embodiment, a canted coil spring 238 in a spring ring 244 configuration is incorporated as a securing device 124. The canted coil spring 238, as a securing device 124, is abutted against the proximally facing surface 228 of the valve 120 and can be abutted against a shoulder 176 inside the interior 123 of the catheter hub 102 to secure the spring ring within the interior of the hub. The proximally facing surface 228 of the valve 120 may have a mating depression to mate with or support the distal arc of the canted coil spring. In the valve opener proximal position of FIG. 16, the coils 240 of the canted coil spring 238 contact both the interior surface of the catheter hub 102 and/or the valve 120 and against the nose section 150 of the valve opener 122. In other examples, the coils can be spaced from the surface of the nose section 150, such as not contacting the nose section, in the valve opener proximal position.

Figure 17:
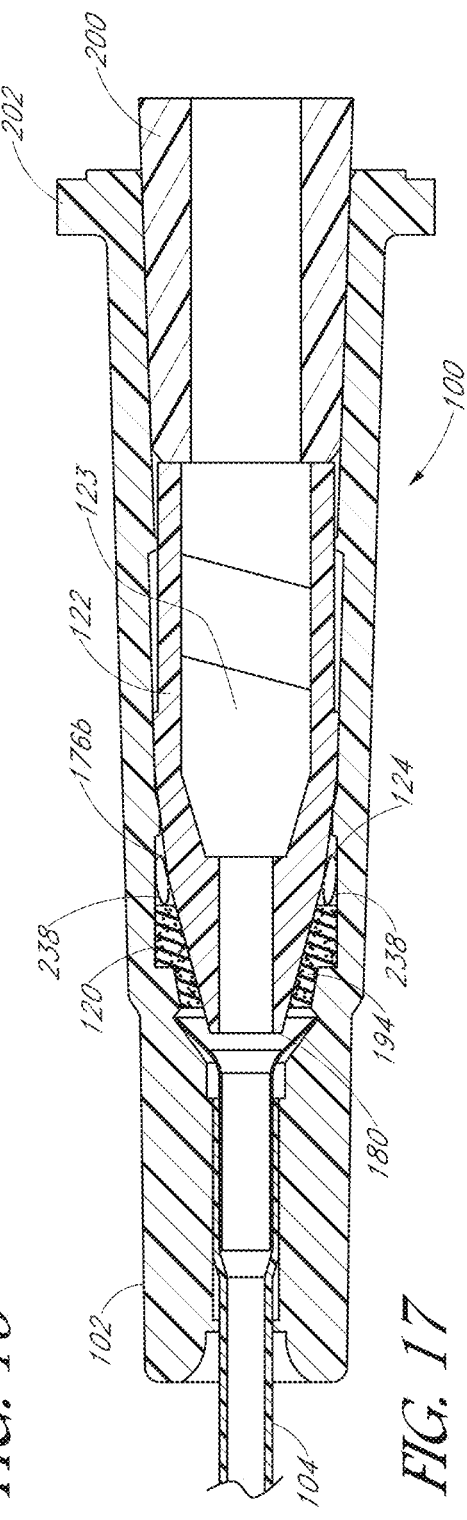
FIG. 17 is a cross-sectional side view of the assembly of FIG. 16 with the valve opener in its distal position and opening the valve.

FIG. 17 shows the valve opener or actuator 122 pushed in the distal direction by a male Luer tip 200 of a medical implement to open or deflect the valve flaps of the valve 120, similar to FIGS. 7, 9, and 11. The canted coil spring 238 is shown compressed by the nose section 150 of the valve opener 122. More specifically, each coil 240 of the plurality of coils of the canted coil spring 238 is compressed by the nose section 150 of the valve opener 122, since coils of a canted coil spring compress when squeezed in the radial direction of the spring ring centerline. The compression of the coils generates force vectors on the nose section 150 since the coils tend to un-compress or recoil. The force vectors generated against the nose section include a force that is generally parallel to the lengthwise axis of the valve opener. The distally directed axial force vector is against the proximal valve surface of the valve 120, if the coils are compressed along one side by the valve, or by the interior of the catheter hub 102, if the coils are compressed along one side by the catheter hub, and the proximally directed force vector is against the valve opener 122.

When the male tip 200 is removed, the coils 240 of the spring 238 expand and push against the nose section 150 to impart a pair of component forces, including a proximally directed axial force vector. This in turn assists in pushing the valve opener 122 in the proximal direction to return the valve opener 122 to its proximal position and to allow the valve 120 to return to its closed position, such as shown in FIG. 16. The forces generated by the spring ring 244 to move the valve opener 122 following removal of the male Luer tip 200 is in addition to the forces generated by the valve flaps of the valve 120 returning to the relaxed or closed state to close the valve slits following removal of the male Luer tip. The proximally directed forces can move the valve opener 122 from a distal position back to a proximal position inside the catheter hub 123, after the male medical implement is disconnected from the catheter hub 102.

Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of a valve actuator into the valve to deflect the valve flaps and movement away from the valve.

FIGS. 18 and 19 show yet another embodiment of a catheter assembly 100, which is similar to the catheter assemblies of FIGS. 4-11 and 16-17 with a few exceptions. In the present embodiment, the valve 120 is provided with an integrated or unitarily formed securing device 124. In the present embodiment, the integrated or unitarily formed securing device 124 can be a retaining skirt section 250 having a generally cylindrical length having an open proximal end with a triangular cross-section, similar to the triangular cross-section of the securing device 124 of FIGS. 4-7. The additional surface area of the external surface of the skirt section 250, or the securing device, assists in further retaining the valve 120 in the catheter hub 102 as the needle is removed and as the valve opener 122 is pushed by a male Luer tip 200 (FIG. 19) to open the valve 120.

The skirt section 250 is sized so that when the valve opener 122 is pushed in the distal direction by the male Luer tip 200, the triangular cross-section of the skirt can be compressed, deformed, or biased by the tapered nose section 150 and the interior of the catheter hub 102 to generate stored energy. Consequently, when the male tip 200, such as a male Luer of a syringe or a tip of an administration set, is removed, the triangular skirt 250 expands to impart a pair of component forces on the nose section 150, which includes a proximally directed axial force vector. This in turn assists in pushing the valve opener 122 in the proximal direction to return the valve opener 122 to its proximal position from the distal position and to allow the valve 120 to return to its closed position, such as shown in FIG. 18.

Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of a valve actuator into the valve to deflect the valve flaps and movement away from the valve.

FIGS. 20 and 21 show yet another embodiment of a catheter assembly 100, which is similar to the catheter assemblies of FIGS. 4-11 and 16-19 with a few exceptions. In the present embodiment, the securing device 124 is a retention ring and the retention ring is provided with integrated or unitarily formed flexible flaps or leaf springs 256. With reference to FIG. 22, the securing device 124 is similar to the securing device described with reference to FIGS. 10, 11 and 14. As shown, securing device has a ring body 220 with a distal end 210 with a curved lip defining a flange 216, which has a generally planar wall surface for abutting a surface of a valve. The ring body 220 has a generally constant wall thickness that tapers outwardly from a first diameter at the distal end, just proximal of the flange 216, to a second larger diameter at the proximal end 212, which has a proximal edge 218 which can abut or contact a shoulder inside a catheter hub to retain the securing device 214 within the catheter hub. Alternatively, the shoulder can be eliminated and the proximal edge 218 can form an interference fit with the inside edge of the catheter hub. The wall surface has a slanted surface that resembles a ramp. The inside surface of the ring body 220 of the securing device 124 defines a bore and wherein the bore is configured to accommodate a valve opener and compress or bias the nose section of the valve opener to impart a pair of component forces, as previously discussed.

In the present embodiment, two or more leaf springs 256, for example, three to eight leaf springs 256, can be provided as part of the retention ring 124 for retaining the valve 120. In another example, there can be only one leaf spring incorporated. The leaf springs 256 can be formed by forming a symmetrical three-sided cut-out on the ring body 220 and bending the cut-out inwardly to form the leaf spring. However, cut-outs can be other than a three-sided cut-out, such as a partial circle cut-out or a multi-sided cut-out greater than three sides. Any number of cut-outs can be utilized to form leaf springs on a securing device to generate force vectors on a valve opener with three-sided cut-outs being preferred. After forming the one or more cut-outs, the direction of bending of the cut-outs to form the leaf spring(s) is the direction that allows the one or more leaf springs to contact the nose section of the valve actuator.

The leaf springs 256 can be sized so that when the valve opener 122 is pushed in the distal direction by a male Luer tip 200, as shown in FIG. 21, the leaf springs 256 are expanded outwardly, deflected outwardly, or biased outwardly from the centerline of the retention ring by the tapered nose section 150 of the valve opener 122. Consequently, when the male tip 200 is removed, the leaf springs 256 compress or un-bias, such as return to their un-biased state, to impart a pair of component forces on the nose section 150, which includes an axial force vector in the proximal direction. The biasing forces of the leaf springs assist in pushing the valve opener 122 in the proximal direction to return the valve opener 122 from a distal position to its proximal position and to allow the valve 120 to return to its closed position, such as shown in FIG. 20. The forces of the leaf springs 256 are in addition to the forces generated by the valve flaps of the valve returning to their relaxed or closed position to close the valve slits following removal of the male Luer tip 200. In the embodiment with one or more leaf springs, the nose section can be rigid without any pliable section or sections, which can optionally be included.

Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement into the valve to deflect the valve flaps and movement away from the valve.

FIGS. 23 and 24 show yet another embodiment of a catheter assembly 100, which is similar to the catheter assemblies of FIGS. 4-11 and 16-21 with a few exceptions. For example, the present catheter assembly can have a needle and a needle hub that have been removed but can be the same as described elsewhere herein. The catheter hub 102 of FIG. 23 can also have a pair of wings 260 extending laterally of the lengthwise axis of the catheter hub 102 in opposite directions at the bottom of the catheter hub. The FIG. 23 view is shown as a top cross-sectional plan view. The pair of wings 260 can be used by a practitioner to secure the catheter hub to the patient after successful venipuncture, such as with an adhesive tape or adhesive dressing. FIG. 24 shows the catheter assembly of FIG. 23 without the wings. The needle assembly 100 can also incorporate a needle guard 130 (FIG. 5) as described elsewhere herein.

In the present embodiment, the securing device 124 is a retention ring and the retention ring is provided with integrated or unitarily formed flexible flaps or leaf springs 256, similar to the embodiment of FIGS. 20-22. However and as further discussed below, the securing device 124 is an eyelet in which one or more leaf springs 256 extend from a flange.

With reference to FIG. 25, the securing device 124 has an eyelet configuration and can be used in the catheter embodiment of FIGS. 23 and 24. As shown, securing device 124 has a flange 216 for a ring body 220, which has an outside diameter (OD) and an inside diameter (ID) defining an opening. The flange 216 can have a thickness, which can be the thickness of the metal sheet used to form the eyelet. The thickness of the flange and the thickness of the leaf springs can be the same or approximately the same. If the flange and the leaf springs are unitarily formed from a single metal sheet, then a thickness at the flange and a thickness at each of the leaf springs can be the same, to within fabrication tolerance of the thickness of the metal sheet.

In the example shown, no cylindrical or elongated hollow body extends from the flange 216. Instead, two or more leaf springs 256, for example, three to eight leaf springs 256 or at least one leaf spring, can extend directly from the flange 216. As shown, four leaf springs 256 are incorporated with the flange 216 and each leaf spring is approximately 90 degrees from an adjacent leaf spring. The leaf springs can be equally spaced along the contour of the flange. The leaf springs 256 can extend from the flange ID, in the proximal direction, and can terminate with a proximal end edge 270. The proximal end edge of the leaf springs 256 can be flat or radiused. The leaf springs 256 can be equally spaced or approximately equally spaced apart along the flange ID. Each leaf spring can have a width and a length that are sufficient to generate a component force on the nose section 150 of the valve opener 122 and collectively all of the leaf springs 256 can generate a proximally directed force that can move the valve opener 122 from a distal position to a proximal position following removal of the male Luer tip, as further discussed below.

In the embodiment shown, a pair of interior notches or slits 262 are provided at the flange ID and on either side edge of each leaf spring 256 to permit each leaf spring to have a bend 266 with a bent radius that is recessed from the flange ID. In other examples, the pair of interior notches 262 can be omitted and the bend in the proximal direction at each bend 266 can be square shape or right angle. Alternatively, the bent radius can extend somewhat inwardly of the flange ID when no interior notches or insufficient interior notches are incorporated.

With reference again to FIG. 23, the securing ring 124 can be configured to secure the valve 120 within the interior 123 of the catheter hub, like other securing rings discussed elsewhere herein. In the present embodiment, the valve 120 is supported on the distally facing surface by an internal shoulder 173 and on the proximally facing surface by the flange 216 of the securing ring 124, which can be supported by an internal shoulder 176b on the proximal side of the flange 216 (FIG. 5). In the position shown, the valve 120 is therefore secured or supported inside the interior of the catheter hub.

In the valve opener proximal position shown, the actuation end 180 of the valve opener 122 can touch the proximally facing surface of the valve 120 or can be spaced from the proximally facing surface of the valve. Whether there is touching or no touching between the valve opener 122 and the valve 120 in the valve opener proximal position, the nose section 150 is located within the boundary defined by the leaf springs 256, but does not touch the leaf springs 256. For example, in the valve opener 122 proximal position, the nose section 150 is spaced from both the leaf springs 256 and the flange 216. The spacing allows the valve opener 122 to move distally into the valve 120 to open the valve flaps 194 before the nose section 150 contacts the leaf springs 256.

In an example, the flange 216 incorporates one or more reliefs or cut-outs 268 on the flange OD. The reliefs can decrease the interference between the flange OD and the interior bore of the catheter hub during installation of the securing device 124 into the catheter hub. Each cut-out 268 can be formed as a straight line cut across two points on the arc of the flange OD. In some examples, each cut-out can have a curve shape, a curve and at least one straight line cut, or a complex curve cut. In an example, a cut-out 268 can be provided at each leaf spring 256, on the flange OD. In other examples, the cut-outs can be located out of alignment with the locations of the leaf springs 256, such as not directly on the OD part of the same ID location as a leaf spring. In still other examples, there can be more cut-outs or fewer cut-outs than the number of leaf springs.

FIG. 24 shows the male Luer tip 200 advanced distally into the interior of the catheter hub to push the valve opener 122 from the proximal position of FIG. 23 to a distal position to open the valve flaps 194 of the valve 120 and the slits formed therebetween, such as during insertion of a male Luer connector of an IV drip line or administration set. In the distal position, the nose section 150 projects through the valve slits to deflect the valve flaps 194 in the distal direction and can compress the valve flaps between the nose section and the interior surface of the catheter hub, or the valve flaps can deflect or deform distally by the nose section of the valve opener with or without compression.

The actuation end 180 is shown distal of the distally deflected valve flaps 194. In other examples, the actuation end can be located at about the same axial position as the deflected valve flaps or proximal of the valve flaps but still allowing fluid to flow across the valve 120, in the proximal direction or distal direction.

The leaf springs 256 can be located on the flange 216 such that when the valve opener 122 is pushed in the distal direction by a male Luer tip 200, as shown in FIG. 24, the leaf springs 256 are deflected radially outwardly by the tapered nose section 150 of the valve opener 122. In an example, the proximal edge 270 of each leaf spring 256 is spaced from the interior of the catheter hub when deflected by the nose section 150 of the valve opener 122. In another example, the proximal edge 270 can contact the interior surface of the catheter hub. The deflected leaf springs 256 and the deflected valve flaps 194 give rise to stored energy that can then push against the nose section 150 of the valve opener to move the valve opener in the proximal direction, upon removal of the male Luer tip.

Consequently, when the male tip 200 is removed, the leaf springs 256 can contract or un-bias to impart a pair of component forces on the nose section 150, which includes an axial force vector in the proximal direction. The biasing forces of the leaf springs assist in pushing the valve opener 122 in the proximal direction to return the valve opener 122 from a distal position to its proximal position and to allow the valve 120 to return to its closed position, such as shown in FIG. 23. The forces of the leaf springs 256 are in addition to the forces generated by the valve flaps 194 of the valve 120 returning to their relaxed or closed position to close the valve slits following removal of the male Luer tip 200. In the embodiment with one or more leaf springs, the nose section 150 can be rigid without any pliable section or sections, which can optionally be included.

Because the valve opener 122 can move to a distal position into the valve 120, such as when pushed by a male Luer tip 200, to open the two or more valve flaps 194 and can return to a proximal position when the male Luer tip 200 is removed to enable the valve flaps to relax or close the slits, the valve 120 can undergo multiple actuating cycles. In an example, the valve can undergo two or more actuation cycles. For example, the valve 120 can undergo at least three cycles, at least four cycles, at least five cycles, or more. Each actuation cycle can comprise movement into the valve by the valve opener to deflect the valve flaps and movement away from the valve.

With reference now to FIG. 26, a securing device, ring or element 124 in accordance with further aspects of the invention is shown. The present securing device 124 can embody an eyelet, similar to the securing device 124 of FIG. 25 and can be used in a similar manner with a catheter assembly as the securing device of FIG. 25. Thus, the present eyelet has a flange 216, at least one leaf spring 256, with four shown, and one or more reliefs 268 at the flange OD, with four shown.

In the present eyelet embodiment, the flange 216 can be shaped to have an arc or curved cross-section. That is, the distally facing surface and the proximally facing surface of the flange 216 are arc-shaped or curved. In an example, the distally facing surface of the flange 216 has a convex shape and the proximally facing surface of the flange 216 has a concave shape. The shaped flange 216 can facilitate installation as the direction of insertion of the securement device 124 and the arc-shaped flange 216 along the cross-section allows the flange OD to smoothly ride against the interior surface during installation. The curved cross section also strengthens the flange against deformation during installation.

The reliefs or cut-outs 268 at the flange OD of the present eyelet are not aligned with the leaf springs 256. Using the hour hand of a clock, the leaf springs 256 can be located at the 2, 4, 8, and 10 o'clock positions along the flange ID while the cut-outs 268 can be located at the 3, 6, 9, and 12 o'clock positions along the flange OD. In other examples, the locations of the leaf springs 256 along the flange ID and the locations of the cut-outs 268 along the flange OD can change. Also, the number of leaf springs and cut-outs can vary, such as having two leaf springs and three cut-outs or three leaf springs and two cut-outs.

As shown and due to the curved or arc-shaped cross-section, the leaf springs 256 of FIG. 26 can be bent without having to include cut-outs or slits 262, as shown with the embodiment of FIG. 25. However, slits or cut-outs may be incorporated to enable bending of the tabs to form the leaf springs.

With reference now to FIGS. 27 and 28, a catheter assembly or needle assembly 100 provided in accordance with further aspects of the invention is shown with the needle and needle hub removed but can have the same needle and needle hub as described elsewhere herein. The needle assembly 100 can also incorporate a needle guard 130 as described elsewhere herein.

In the present embodiment, the catheter hub 102, catheter tube 104, valve 120, valve opener 122, and securing device 124 can be similar to those shown with reference to FIGS.

18-19 with a few exceptions. In the present embodiment, the securing device 124 is a retention ring made from an elastomeric material. For example, the securing device 124 may be made from an elastomeric material, such as an O-ring, to provide a proximally directed force to the valve opener when compressed or deformed between the valve opener nose section 150 and the inner wall of the catheter hub 102 in the distal position of the valve opener. The securing device 124 can have a structure that embodies an O-ring of various possible cross sections, such as round, oval, square, rectangular. As shown, the securing device 124 is an elastomeric ring with a round cross-section. The securing device 124 can be separately formed from the valve 120 and used with the valve 120 to secure the valve inside the interior of the catheter hub.

As shown, the valve 120 is secured or supported on the distal side by an internal shoulder 173, which prevents or limits axial distal displacement of the outer perimeter of the valve, but still allows the valve flaps 194 to deflect in the distal direction when pushed by a valve opener 122. The valve 120 is secured or supported on the proximal side by the securing ring 124, or elastomeric ring of the present embodiment. The elastomeric ring can abut an internal shoulder 176b to secure the elastomeric ring, and hence the valve, from displacing in the proximal direction.

The securing device 124 and the nose section 150 of the valve opener 122 are spaced from one another in the valve opener proximal position of FIG. 27. The gap or spacing between the two provides clearance for the valve opener 122 to move in the distal direction to open the valve, such as to deflect the valve flaps 194, before closing the gap, contacting or hitting the securing device 124 with the valve opener. In the state shown in FIG. 27, the actuating end 180 at the nose section 150 of the valve actuator 122 is located within the bore defined by the securing device 124, but spaced from or not contacting the securing device. The tapered surface of the nose section is also spaced from the securing device. This spacing or gap allows the valve actuating element 122 to move forward in the distal direction before hitting or contacting the securing device 124. The actuating end 180 of the valve actuator is shown in contact with the proximally facing surface of the valve 120. In other examples, the actuating end 180 can be slightly spaced from the proximally facing surface of the valve.

FIG. 28 is a cross-sectional side view of the assembly of FIG. 27 with a male Luer tip 200 inserted into the open proximal end 136 and advancing the valve opener 122 into the valve 120 to open the valve flaps 194 and open fluid communication between the male Luer tip 200 and the lumen of the catheter tube 104, similar to other embodiments described elsewhere herein. Although not shown, the male Luer tip 200 can have a threaded collar for engaging the lugs or external threads 202 on the catheter hub to maintain the valve actuator in the distal position to open the valve.

In an example, the valve opener 122 is configured to move distally when advanced by the male Luer tip 200. The amount or distance that the valve opener moves in the distal direction should be sufficient to allow the actuating end 180 and the nose section 150 to deflect the valve flaps 194 in the distal direction to open the slits to then open fluid communication between the male Luer tip 200 and the catheter tube 104. In the example shown, the actuating end 180 of the valve opener 122 moves distal of the valve flaps and the valve flaps are compressed between the interior of the catheter hub 102 and the tapered surface of the nose section 150, or the valve flaps are deflected or deformed in the distal direction by the nose section of the valve opener with or without compression. In some examples, the actuating end 180 moves a distance that is equal to the ends of the valve flaps 194 or short of the ends of the valve flaps, but still opening the valve sufficiently for free flow in both directions.

In the example shown, the elastomeric ring of the securing device 124 acts like a biasing member. For example, when the nose section 150 is pushed against the securing device 124 and compressing or biasing the securing device between the nose section and the interior surface of the catheter hub, stored energy is imparted to the elastomeric material, which enables the elastomeric material to exert an opposite biasing force against the nose section 150 of the actuator. Thus, when the nose section 150 is pressed against the elastomeric ring, the elastomeric ring imparts a pair of component forces or force vectors on the nose section 150, which includes a force that acts generally parallel to the lengthwise axis of the catheter hub in a proximal direction.

Upon withdrawal of the male Luer tip 200, such as when replacing an IV fluid bag attached to the male Luer tip 200, the distally directed force acting on the proximal edges 182 of the two plunger elements 152 by the male Luer tip 200 is removed or ceased and the female Luer 204 is unoccupied by any external object. This allows for the valve opener 122 to return to its proximal position of FIG. 27, now vacated by the male Luer tip. In an example, the elasticity of the valve 120 allows the valve flaps 194 to recoil to their more relaxed state, such as to move to the position shown in FIG. 27. This recoiling action of the valve flaps 194 and the shape of the nose section 150 of the valve opener allow the valve flaps to impart force vectors on the nose section 150 to cause the valve opener 122 to move from the distal position shown in FIG. 11 to a proximal position, generally as shown in FIG. 10. Additionally, and as discussed above, the elasticity of the securing device 124 exerts a returning force against the nose section 150 to move the valve opener 122 in the proximal direction to return the valve opener essentially to the position shown in FIG. 27.

Aspects of the invention is therefore understood to include a catheter assembly or needle device comprising a catheter hub having a catheter tube extending in a distal direction, a needle attached to a needle hub and the needle extending through the catheter hub and the catheter tube. The catheter hub comprising a body having an exterior surface and an interior surface defining an interior cavity. A valve and a valve opener can be located inside the interior cavity. In an example, a securing device having a body defining a bore is located proximal of the valve and secures the valve in the catheter hub. The securing device can provide an interference with the valve opener when the valve opener is advanced in the distal direction by a male Luer tip to open the valve flaps of the valve and wherein the interference fit provides force vectors that include a vector that extends generally parallel to the lengthwise axis of the catheter hub to return the valve opener from a distal position to a proximal position, when the male Luer tip is removed from the catheter hub. The securing device can additionally provide a securing function for securing the valve inside the catheter hub and preventing the valve from inadvertent proximal displacement to dislodge from the catheter hub and not provide any return force to the valve opener. The securing device can be an elastomeric material. The material preferably ranges between 30 and 70 Shore A hardness. It can also have a shore A hardness below 30 or above 70. In an example, the elastomeric material is an O-ring. In a particular example, the O-ring can have a round cross-section.

Because the valve opener can move to a distal position into the valve, such as when pushed by a male Luer tip, to open the two or more valve flaps and can return to a proximal position when the male Luer tip is removed to enable the valve flaps to relax or close up to close in the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of the valve opener into the valve to deflect the valve flaps and movement away from the valve to allow the flaps to close.

With reference now to FIGS. 29 and 30, a catheter assembly or needle assembly 100 provided in accordance with still further aspects of the invention is shown with the needle and needle hub removed but can have the same needle and needle hub as described elsewhere herein. The needle assembly 100 can also incorporate a needle guard 130 as described elsewhere herein. The present catheter assembly is particularly similar to the catheter assembly of FIGS. 27 and 28, discussed immediately above. For example, the present securing device 124 can embody an elastomeric material, similar to the embodiment of FIGS. 27 and 28. However, in the present embodiment, the elastomeric material, which can be an O-ring, can have a generally square or polygonal cross-section.

With reference now to FIGS. 31, 32A and 32B, yet another embodiment of a catheter assembly or needle assembly 100 is shown, which is similar to the catheter assemblies of FIGS. 4-11 and 16-21 with a few exceptions. FIG. 31 shows the catheter assembly with the needle and needle hub removed but can have the same needle and needle hub as described elsewhere herein. The needle assembly 100 can also incorporate a needle guard 130 as described elsewhere herein. FIG. 32A shows a male Luer tip 200 inserted into the female Luer 204 (FIG. 31) and advancing the valve opener 122 to open the valve 120, as further discussed below. FIG. 32B shows the same view as FIG. 32A but rotated 90 degrees along the lengthwise axis of the catheter hub. In the present embodiment, the valve 120 is provided with an integrated or unitarily formed securing device 124. In the present embodiment, the integrated or unitarily formed securing device 124 can be a retaining skirt section 250 formed with the valve disc 121 (FIGS. 34 and 35). The skirt section 250 can have a generally constant thickness and a proximal end surface 290, which is sized to abut or contact an internal shoulder 176b of the catheter hub to secure the valve 120 inside the catheter hub 102, from proximal movement. The proximal end surface 290 of the skirt section 250 has a sufficient thickness so that part of the skirt section is exposed radially of the internal shoulder 176b. This exposed portion of the skirt section allows or provides a target for the valve opener 122 to push against to compress, deform, or bias the skirt section 250, as further discussed below.

With reference to FIG. 34 in addition to FIG. 31, the valve 120 of the present embodiment can have a valve disc 121 and an integrated skirt 250. In the example shown, the valve disc 121 and the skirt section 250 are unitarily formed. The skirt section 250 can be viewed as a generally cylindrical length having an open proximal end. The valve disc 121 is shown with a plurality of slits or valve disc slit portions 234 defining a plurality of valve flaps 194. In the present embodiment, the wall thickness of the valve disc 121, in the axial direction, is generally constant, without distinct first portions 168 and second portions 170 as shown in FIG. 13 and elsewhere in this description. However, distinct first portions 168 and second portions 170 can be incorporated with a valve having a valve disc 121 and a skirt section 250, as shown in FIG. 35.

In an embodiment, rather than incorporating a generally constant thickness along the length of the skirt section 250, the skirt section can incorporate a ramped surface along a cross-section, similar to that shown in FIGS. 18 and 19. For example, the valve 120 with the valve disc 121 having distinct first and second portions 168, 170, as shown in FIG. 35, can have a skirt section 250 with a ramped cross-section. The valve 120 of FIG. 35 is understood to be useable with the catheter assembly of FIGS. 31, 32A and 32B, similar to the valve 120 of FIG. 34.

In the present embodiment, the valve opener 122 has a body comprising a nose section 150 and a proximal section 157 comprising two plunger elements 152, two projections 154, and two stabilizing elements 158, like other valve openers described elsewhere herein. The plunger elements 152 can be spaced from one another and having at least one flow channel located therebetween. Each plunger element can include ribs, bumps, projections, or sections of varying thicknesses to control the rigidity of the plunger element. The ribs or bumps can also help to stir flow for flushing purposes as fluid passes between the plunger elements. The valve opener 122 of the present embodiment is shown in perspective view in FIG. 33 and in cross-section in FIGS. 31, 32A and 32B. In some examples, the valve opener 122 of FIG. 33 can be unitarily formed. In other examples, the valve opener can be co-molded or insert molded with one or more different materials or components. For example, the two stabilizing elements 158 can be made from a metal material that can be molded with the remaining parts of the valve opener 122.

In some examples, the distal and proximal edges of the stabilizing elements 158 can be parallel to one another. The distal edge of the stabilizing element 158 can be generally orthogonal to the lengthwise axis of the valve opener 122 or be angled to the lengthwise axis. Each of the two stabilizing elements 158, when two are utilized, can have a length and a constant width along the length. However, the width can vary along the length of the stabilizing element 158, as shown in FIG. 43. In yet other examples, one or both stabilizing elements can be non-continuous, such as having a gap.

In the present embodiment, a transition section 296 is provided proximal of the nose section 150. As shown in FIG. 33, the transition section 296 includes a pair of opener shoulders 294 and each having an abutting edge 298. The two opener shoulders 294 can be spaced from one another and the two abutting edges 298 can be located approximately at a same axial point or location on the valve opener, on different sides of the nose section 150, to push into the valve 120 at about the same time when the valve opener is advanced by the male Luer tip 200. Each opener shoulder 294 can include a slanted or sloped surface extending proximally of the abutting edge 298. The two opener shoulders 294 are located proximate a landing section 300 at the transition section 296 of the valve opener. Raised lips or ribs can be provided sparingly thoroughly the body of the valve opener to increase stability and/or strength.

In some examples, the two opener shoulders 294 with tapered surfaces and abutting edges 298 may be omitted or modified from the shapes shown. For example, the nose section 150 can extend directly to the stepped shoulder 293 at the transition section 296 without the tapered shoulder 294. Without the tapered shoulders 294, abutting surfaces 295 on the stepped shoulders 293 can compress the skirt section. In other examples, the tapered shoulders 294 can have different shapes, such as be generally square or have square surfaces without any tapered surface so that the abutting edges 298 are approximately the same height as the shoulders 294 themselves. In other words, the abutting edges 298 can be provided with the valve actuator, on two sides of the nose section 150, without the tapered shoulders 294. In using the alternative valve opener 122 without the tapered shoulders 294, the abutting edges 295 of the two stepped shoulders 293 can push against the proximal end surface 290 of the valve 120 directly.

As shown in FIG. 33, the outside diameter (OD) at the landing section 300 is generally constant. In an example, a length of the landing section 300 has the same OD along the length thereof. In still other examples, there can be a slight increasing slope or a slight decreasing slope. The sloped surface at the landing section 300 can be practiced so long as the landing section does not abut or interfere with the skirt section 250, as shown in FIGS. 32A and 32B, and/or does not weakened the transition section thus rendering it operable as a valve opener. As shown, the bore at the nose section 150 and the landing section 250 has a generally constant inside diameter (ID).

Distal of the landing section 300, on the exterior, the nose section 150 can be described as a generally frustoconical shaped structure. The tapered surface of the nose section 150 allows the valve flaps 194 to impart a pair of component forces, which include a proximally directed force, to return the valve opener 122 to its proximal position after removal of the male Luer tip.

FIG. 32A shows the two abutting edges 298 of the two opener shoulders 294 (FIG. 33) pushing against the proximal surface 290 of the skirt section 250 of the valve 120 due to the male Luer tip 200 pushing the valve opener 122 in the distal direction into the valve. Overlapping surfaces of the skirt section 250 and the opener shoulders 294 indicate interference or compression of the skirt section 250 between the distal shoulder 173 and the abutting edges 298 of the valve opener. Thus, when the valve 120 is opened by the valve opener 122, the valve flaps 194 are compressed between the nose section 150 of the valve opener and the interior surface of the catheter hub, or the valve flaps are deflected or deformed in the distal direction by the nose section of the valve opener, and the skirt section 250 is compressed or deformed between the distal shoulder 173 and the two abutting edges 298 of the valve opener. Where the abutting edges 298 and the shoulders 294 with the tapered surfaces are omitted, the end surfaces 295 of the two stepped shoulders 293 (FIG. 33) can compress the skirt section 250. The size and shape of the stepped shoulder 293 and the nose section 150 can be adjusted to compress the skirt section 250 when the tapered shoulders 294 are omitted.

The compression, deflection, deformation or bias of the various surfaces or sections of the valve 120 when activated by the valve opener 122 creates stored energy in the valve. When the male Luer tip 200 is removed from the female Luer 204 of the catheter hub 102, the stored energy is released in the form of the valve flaps 194 and the skirt section 250 returning to their more relaxed state. Consequently, the valve flaps 194 exert a proximally directed force against the nose section 150 and the skirt section 250 exerts a proximally directed force against the two abutting edges 298 to move the valve opener 122 from the distal position shown in FIGS. 32A and 32B to a proximal position shown in FIG. 31.

Because the valve opener 122 can move to a distal position into the valve 120, such as when pushed by a male Luer tip 200, to open the two or more valve flaps 194 and the valve opener can return to a proximal position when the male Luer tip is removed to enable the valve flaps 194 and the skirt section 250 to relax or close up the slits 234 (FIGS. 34 and 35), the valve can undergo multiple actuating cycles. In an example, the valve 120 can undergo two or more actuation cycles. For example, the valve can undergo at least three cycles, at least four cycles, at least five cycles, or more. Each actuation cycle can comprise movement of a valve actuator into the valve to deflect the valve flaps and movement away from the valve.

The valve, such as the valve flaps or the skirt section of the valve can be deflected, biased, or deformed by a first structure, such as the valve opener, moving into the valve without requiring a second structure to be located distal of the first structure, although optionally the second structure can be incorporated. For example, the valve flaps can deflect distally by the valve opener when the valve opener moves in the distal direction. The distal deflection of the valve flaps can occur with or without the presence of a shoulder or a rigid surface located on the distal side of the valve flaps. However, when there is a shoulder or a rigid surface on the distal side of the valve flaps, the valve flaps can both deflect distally and can compress between the valve opener and the shoulder or rigid structure on the distal side. Other objects can be deflected, biased, or deformed without an opposing structure, such as a leaf spring being deflected, biased, or deformed by the nose section of a valve opener or a spring C-ring or helix being expanded by insertion of a tapered section of the nose section.

Aspects of the invention are therefore understood to include a catheter assembly or needle device comprising a catheter hub having a catheter tube extending in a distal direction, said catheter hub comprising a body having an exterior surface and an interior surface defining an interior cavity. A valve and a valve opener can be located inside the interior cavity. In an example, a securing device having a body defining a bore is located proximal of the valve. In an example, the securing device can be unitarily formed with the valve and can be a skirt section. For example, a valve disc can be unitarily formed with a valve skirt or skirt section and wherein the valve skirt can act as a securing device to retain the valve disc within the interior of the catheter hub.

The valve flaps of the valve can impart a proximally directed return force to return the valve opener from a distal position to a proximal position. Additionally, the valve opener can include one or more abutting edges to compress, deform, or bias the skirt section axially against a distal shoulder of the catheter hub. In other words, the valve skirt or skirt section can have a length and wherein the valve opener can compress or deform the valve skirt during actuation of the valve opener to a distal position to open the valve and decrease the length of the valve skirt from a first length to a shorter second length. When the skirt section decreases in length due to the valve actuator, the skirt section receives stored energy. The skirt section can therefore provide an axially directed force against the valve opener when the stored energy is released, such as to the one or more abutting edges of the valve opener, to return the valve opener to a proximal position, upon removal of the male Luer tip.

In an example, the securing device can provide an interference with the valve opener, such as an elastomeric part of the valve opener, when the valve opener is advanced in the distal direction by a male Luer tip to open the valve flaps of the valve, such as to deflect the valve flaps in the distal direction by the nose section, and wherein the deflection can provide force vectors that include a force vector that extends generally parallel to the lengthwise axis of the catheter hub to return the valve opener from a distal position to a proximal position, when the male Luer tip is removed from the catheter hub. In an example, the interference, bias, deflection, or compression provides stored energy to a skirt section of the valve. The stored energy can release to push against one or more abutting surfaces of the valve opener in the proximal axial direction.

The valve opener therefore can have multiple surfaces, such as a nose section and one or more abutting edges, for deforming a valve at multiple distinct locations of the valve to provide stored energy to the valve. The deformed surfaces of the valve can include the valve flaps and other surfaces of the valve, different from the valve flaps. For example, in addition to the valve flaps, the skirt section can compress axially by the valve opener. The catheter hub can include a needle projecting through the catheter hub, the valve, the valve opener, the securing device and the catheter tube. The needle can attach to a needle hub at the needle's proximal end.

With reference now to FIGS. 36 and 37, yet another catheter assembly or needle assembly 100 in accordance with aspects of the invention are shown. The catheter assembly 100 is shown with the needle and needle hub removed but can have the same needle and needle hub as described elsewhere herein. The needle assembly 100 can also incorporate a needle guard as described elsewhere herein.

In the present embodiment, the catheter hub 102, catheter tube 104, valve 120, valve opener 122, and securing device 124 can be similar to those shown with reference to FIGS. 8 and 9 with a few exceptions. In the present embodiment, the annular slit or annular channel 206 is provided on the proximally facing surface of the valve 120 and has been enlarged to receive the distal end of the securing device 124. That is, the enlarged gap of the annular channel 206 of the present embodiment can contact the outside surface of the ring body of the securing ring 124 but not the inside surface of the ring body, due to the enlarged gap. The ring body can also contact the end surface or distal surface of the annular channel to control or set the depth of the annular channel 206 relative to the ring body. This configuration allows the securing device 124 to retain the valve 120 within the interior of the catheter hub, as described with reference to FIGS. 8 and 9, while relaxing tolerance or simplify manufacturing requirements for forming or creating the annular channel 206 since the inside surface of the ring body does not have to be gripped by the annular channel. A channel is also easier to form by standard molding techniques than partially slitting the valve disc.

FIG. 38a, shows the retention ring 124 used in connection with the catheter assembly 100 of FIGS. 36 and 37. As shown, ring body 220 of the retention ring 124 of the present embodiment can have a wall with a length between the proximal end 212 and the distal end 210 with a generally constant wall thickness and a curved body section 214 at the proximal end of the retention ring. The wall has an interior that defines a bore for accommodating the nose section 150 of the valve opener 122. The wall of the securing device 124 can be generally cylindrical except for the curved body section 214 at the proximal end 212. In an example, the proximal end 212 of the retention ring 124 can have an outwardly curved lip 214 for securing the retention ring 124 against an optional internal shoulder 176b of the catheter hub 102. Once located against the internal shoulder 176b, the securing device 124 can help to secure the valve 120 from displacing in the proximal direction. The valve 120 is secured or supported from distal movement by being located against a shoulder 173 of the catheter hub 102 on the distally facing surface of the valve. In some examples, the curved lip 214 of the retention ring 124 has an interference fit with the interior of the catheter hub without a shoulder.

One or more leaf springs 256 can be provided with the present securing device 124. As shown, four leaf springs 256 are provided with the securing device and equally spaced from one another, at approximately the 2, 6, 8, and 10 o'clock positions. However, the leaf springs can be located at different arc positions of the ring body 220. In an example, a leaf spring 256 can be formed by making at least two cuts through the proximal edge 312 of the ring body 220. As shown, the leaf spring 256 is formed from two generally parallel cuts through the curved lip 214 to enable the metal to be bent to form the leaf spring 256 and the cuts forming two side edges of each leaf spring 256.

In one example, all leaf springs 256 incorporated with the present securing device 124 can be formed in the same manner, such as by utilizing two generally parallel cuts for each leaf spring. In other examples, the cuts can be non-parallel. In still other examples, a combination of different leaf springs can be practiced. For example, the ring body 220 can have two proximally located leaf springs 256 with cuts formed through the proximal edge 312 as shown in FIG. 38a and two leaf springs formed between the distal end 210 and the proximal end 212, similar to the leaf springs of FIG. 22. In still other examples, fewer than four leaf springs, such as three, two, or one, or greater than four leaf springs, can be practiced, such as five, six, or seven leaf springs. Additionally, spacing between the cuts can vary to change the width of or size of the leaf springs, which can change the spring force or biasing force generated by the leaf springs. The cuts through the proximal edge 312 to form the leaf springs 256 have the advantage of creating proximal sections 255 between two adjacent leaf springs 256. The proximal sections 255 can deflect or flex when sliding the securing device 124 into the catheter hub to secure the valve. The ability of the proximal sections 255 to deflect or flex can decrease the insertion force for installing the securing device. As with the embodiment described above and shown in FIG. 25 there can be a cut out instead of a slit between the leaf spring 256 and the proximal edge 312 of the ring body 220. This would increase the flexibility of both the leaf spring 256 and the proximal edge 312.

FIG. 38b is an end view of the securing device 124 of FIG. 38a. In the view shown, the four leaf springs 256 are equally spaced along the proximal end 212 of the securing device. Further, the securing device is oriented so that the four leaf springs are located at the 3, 6, 9, and 12 o'clock positions.

As shown in FIG. 36, the securing device 124 and the nose section 150 of the valve opener 122 are spaced from one another in the valve opener proximal position. The gap or spacing between the two provides clearance for the valve opener 122 to move in the distal direction to open the valve, such as to deflect the valve flaps 194, before contacting or hitting the securing device 124. In the state shown, the actuating end 180 at the nose section 150 of the valve actuator 122 is located within the bore defined by the securing device 124, but spaced from or not contacting the securing device. The actuating end 180 and the nose section 150 are also spaced from a cylinder defined by the plurality of leaf springs 256. This spacing or gap allows the valve actuating element to move forward in the distal direction before hitting or contacting the securing device, such as before hitting the leaf springs. The actuating end 180 is shown in contact with the proximally facing surface of the valve 120. In other examples, the actuating end 180 can be slightly spaced from the proximally facing surface of the valve 120.

FIG. 37 is a cross-sectional side view of the assembly of FIG. 36 with a male Luer tip 200 inserted into the open proximal end 136 and advancing the valve opener 122 into the valve 120 to open the valve flaps 194 and open fluid communication between the male Luer tip 200 and the lumen of the catheter tube 104, similar to the embodiment of FIGS. 20 and 21. Although not shown, the male Luer tip 200 can have a threaded collar for engaging the lugs or external threads 202 on the catheter hub 102 to further maintain the valve actuator 122 in the distal position to open the valve 120.

In an example, the valve opener 122 is configured to move distally when advanced by a male Luer tip 200. The amount or distance that the valve opener moves in the distal direction should be sufficient to allow the actuating end 180 and the nose section 150 to deflect the valve flaps 194 in the distal direction to open the slits to then open fluid communication between the male Luer tip 200 and the catheter tube 104. In the example shown, the actuating end 180 of the valve opener 122 moves distal of the valve flaps and the valve flaps can be compressed between the interior of the catheter hub 102 and the tapered surface of the nose section 150, or the valve flaps 194 can be deflected or deformed distally by the nose section 150 of the valve opener 122 without or without compression. As shown, the actuating end 180 moves a distance that is equal to the ends of the valve flaps 194 or short of the ends of the valve flaps but still opening the valve sufficiently for free flow in both directions.

In the example shown, tapered surface of the nose section 150 deflects or biases the plurality of leaf springs 256 of the securing ring 124 radially outwardly to provide the leaf springs with stored energy. The curved lip 214 can act like a biasing member. Thus, upon release of the leaf springs 256, the leaf springs impart a pair of component forces or force vectors on the nose section 150 of the valve opener 122, which include a force that acts generally parallel to the lengthwise axis of the catheter hub 102 in a proximal direction.

Upon withdrawal of the male Luer tip 200, such as when replacing an IV fluid bag attached to the male Luer tip 200, the distally directed force acting on the proximal edges 182 of the two plunger elements 152 by the male Luer tip 200 is removed or ceased and the female Luer 204 is unoccupied by an external object. This allows for the valve opener 122 to return to its proximal position, now vacated by the male Luer tip. In an example, the elasticity of the valve 120 allows the valve flaps 194 to recoil, by releasing its stored energy, to their more relaxed state, such as to move to the position shown in FIG. 36. This recoiling action of the valve flaps 194 and the shape of the nose section 150 of the valve opener allow the valve flaps 194 to impart force vectors on the nose section 150 to cause the valve opener 122 to move from the distal position shown in FIG. 37 to a proximal position, generally as shown in FIG. 36. Additionally, the leaf spring 256 acting on the nose section 150 also exert a proximally directed force to further aid in returning the valve opener to its proximal position.

Because the valve opener 122 can move to a distal position into the valve 120, such as when pushed by a male Luer tip 200, to open the two or more valve flaps 194 and the valve opener can return to a proximal position when the male Luer tip is removed to enable the valve flaps 194 to relax or close up to close in the slits, the valve can undergo multiple actuating cycles. In an example, the valve can undergo two or more actuation cycles. For example, the valve can undergo at least three cycles, at least four cycles, at least five cycles, or more. Each actuation cycle can comprise movement of a valve actuator into the valve to deflect the valve flaps and movement away from the valve to allow the valve flaps to close.

Exemplary methods of making and of using the catheter assemblies and components thereof in accordance with aspects of the invention will now be described with other process steps contemplated. The securing devices 124 disclosed herein can be molded from a suitable thermoplastic or formed from a sheet metal, such as stainless steel. The valve 120 itself can be formed of an elastic polymer, silicone, synthetic or natural rubber. Thus, when the securing device 124 is a unitarily formed retention or retaining skirt 250 (FIGS. 18 and 19) with the valve 120, the retaining skirt 250 can also be made from an elastic polymer, silicone, synthetic or natural rubber. When forming the securing device 124 from a metal material, metal has the advantage of avoiding elastic creep during the shelf life of the device, which can be up to 5 years.

The order of assembling a catheter assembly in accordance with aspects of the invention can be as follows with other steps contemplated: attach a catheter tube to a metal bush, attach the metal bush/catheter tube in the catheter hub, assemble the valve and securing device into a groove between a distal and proximal shoulder on the inner surface of the catheter hub. The securing device can abut or press against a shoulder at the proximal side or end of the securing device. The securing device can be any one of the securing devices described elsewhere herein, including a unitarily formed skirt, O-ring or a spring ring.

Next, insert the valve opener into the catheter hub, insert the butt end of a needle through a needle guard, attach the butt end of the needle to a needle hub, and open the valve by pushing on the proximal end of the valve opener with an opening tool. In an example, the opening tool can resemble a male Luer tip but with a horizontal split line to enable placement of the tool around the needle shaft or to remove the tool from the needle shaft. Next, insert the needle tip first through the open valve, release the pushing force on the valve opener by removing the opening tool from the catheter hub, moving the two halves of the opening tool away from each other, proceed to insert the needle completely through the catheter tubing until the needle tip extends completely from the catheter tube and the needle guard is located in its ready to protect position and the distal most end of the needle hub is projecting into the catheter hub, attach the vent plug to the proximal end of the needle hub. Other variations of the above steps are possible, for instance changing the sequence of the steps or deleting one or more of the steps. When an additional housing is used as part of the needle guard then it may not be necessary to insert the needle guard into the catheter hub or only a small portion of the needle guard may be inserted into the catheter hub.

In use the needle tip penetrates the patient's skin and vein, blood flashes back through the needle into the needle hub, the catheter tip is slid over the needle tip into the vein, a secondary blood flashback is seen rising up the catheter tubing, the rest of the catheter tube is inserted into the vein as the needle is removed until the catheter hub is near the insertion site of the skin. Either upon removal of the needle from the catheter hub or as an activation step is undertaken, the needle guard activates to protect the user from inadvertent needle stick. The valve flaps of the valve close as the needle tip is moved proximally of the valve. Thus, the user is protected from both inadvertent needle stick injury and blood contamination leaking out of the catheter hub. The valve continues to protect the user from blood contamination upon subsequent disconnections of any male implements attached to the catheter hub female Luer.

Either a blood collection instrument, extension line or administration set, all with a male Luer connector could be attached to the female Luer of the catheter hub. When the male Luer connector is inserted into the catheter hub, the tip pushes on the valve opener to open the valve to allow either infusion or withdraw of blood. When the male Luer is to be disconnected, the valve would close as described above and the user would continue to be protected against blood leakage out of the catheter hub. The valve opener can move from a distal position to a proximal position by aid of proximally directed forces from the valve flaps closing and from the securing ring described elsewhere herein. Connections and disconnections could be repeated and still no blood would leak out of the catheter hub. Normally after blood is collected from the patient, then a flush syringe filled with flushing fluid can be attach to the catheter hub to flush out residual blood from the catheter hub and the catheter tube. The catheter hub, valve, securing device or securing ring, and valve opener would be configured to minimize any residual blood after flushing. Adding openings in between the two plunger elements 152 help to minimize residual blood by adding flow paths.

With reference now to FIG. 39, a schematic cross-sectional side view of a catheter assembly 100 provided in accordance with further aspects of the invention is shown. The present catheter assembly 100 is similar to other catheter assemblies described elsewhere herein with a few exceptions. Like other embodiments, the catheter assembly 100 can have a needle 108 and a needle hub 106, a catheter tube 104 attached to a catheter hub 102 having a valve 120 and a valve opener 122 located inside the interior 123 of the hub body 126. A securing device can also be incorporated for securing the valve 120 inside the catheter hub, similar to the embodiments of FIGS. 4, 5, 8, 9, 20, 21 and 36-38, and elsewhere.

Optionally, the valve 120 can be provided with an integrated or unitarily formed securing device. The integrated or unitarily formed securing device can be a retaining skirt section having a triangular cross-section or other shaped skirt cross-section, similar to that shown in FIGS. 18, 19, 31, 32A, and 32B. Further, a needle guard may be incorporated for guarding the needle tip upon retraction of the needle following successful venipuncture, similar to the needle guard 130 shown in FIGS. 4 and 5 and elsewhere. In other examples, a needle guard as shown in FIGS. 45A-46B may be used with the catheter assembly of FIG. 39.

In the present embodiment, the hub body 126 of the catheter hub 102 is provided with a side port 360 pointing in the proximal direction and having an elongated body 362 that is formed at an acute angle to the lengthwise axis of the hub body 126. The side port 360 can be unitarily formed with the hub body 126 of the catheter hub. The side port 360 can be used with a tubing, which tubing is then connected at the opposite end with a fluid connector. Optionally, a vent plug, such as the vent plug 112 attached to the needle hub 106, can be placed at the opening of the side port 360 if used without a tubing.

Figure 41:
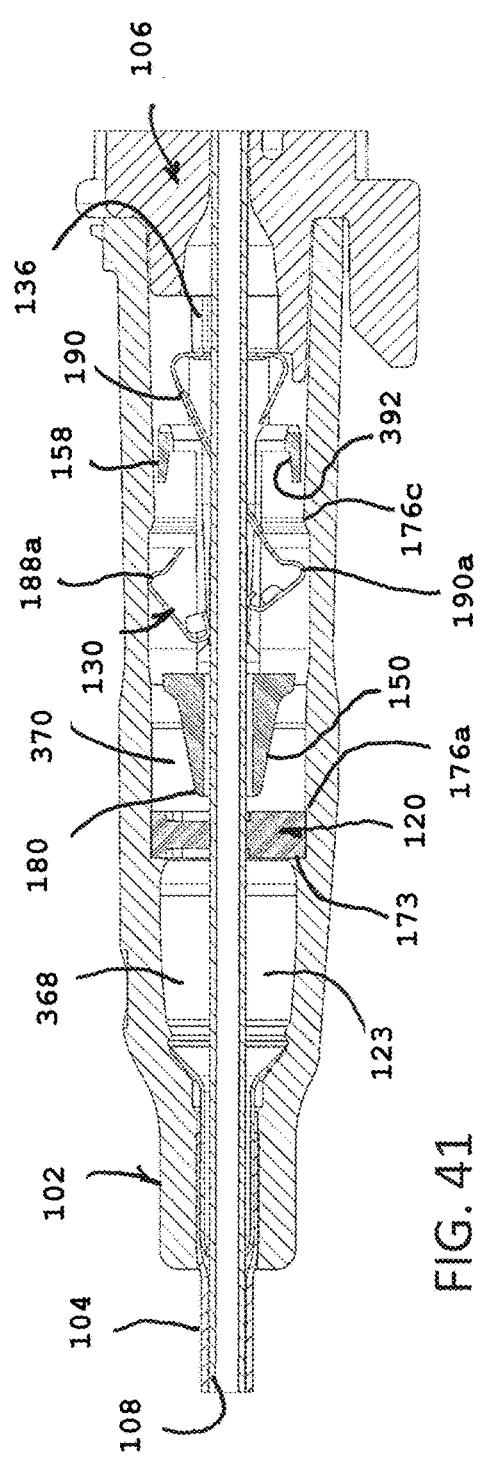

The side port 360 can have a bore 364 with an inlet opening. The bore 364 of the side port 360 can be in fluid communication with the interior cavity 123 of the catheter hub and with the lumen of the catheter tube 104. In an example, the bore 364 of the side port is in fluid communication with the interior chamber or interior cavity 123 distal of the valve 120 and the catheter lumen. Following removal of the needle 108 and the needle hub 106 after successful venipuncture from the catheter hub, the one or more flaps of the valve 120 can close to isolate the interior cavity into a distal chamber 368 distal of the valve and a proximal chamber 370 proximal of the valve (FIG. 41). The side port 360 can be isolated from the proximal chamber 370 (FIG. 40) of the interior cavity due to the valve 120. However, when the needle is located in the catheter tube and the needle deflects one or more of the valve flaps, there may be fluid communication with the proximal chamber 370. A tubing 376 (FIG. 42) can connect to the side port 360 and a fluid connector 378 (FIG. 42) can connect to the opposite end of the tubing, as further discussed below. The catheter hub 102 with the side port 360 and tubing can be called or referred to as an integrated catheter 100a.

Also shown in FIG. 39 is a vent plug 112 connected to the proximal opening of the needle hub 106, similar to other vent plugs described herein, and an optional paddle grip 372. When incorporated, the paddle grip 372 can provide a grip, which is closer to the puncture point during insertion of the needle 108 into the vein. In general, the closer to the puncture point the more accurate the puncture can be made. When incorporated, the paddle grip 372 can be unitarily formed with the needle hub 106. The paddle grip 372 can embody a generally flat structure extending to a side of the needle hub and can have a length that extends in the distal direction. The paddle grip 372 can have a hump-like or curved-like outer contour with a rounded outer edge or can have other shapes. Surface bumps or gripping features can be incorporated with the paddle grip. The paddle grip 372 can be adjustable for a left-handed user or a right-handed user by rotating the needle hub 102 about the lengthwise axis of the needle 108. In some examples, the paddle grip 372 can be formed with a clip ring and the clip ring can slide onto the needle hub. The clip ring can be adjustable or rotatable about the needle hub 106 to allow the position of the paddle grip 372 to change as desired by the practitioner. Exemplary adjustable paddle grips are disclosed in U.S. Pub. No. 2017/0173304A1, the contents of which are expressly incorporated herein by reference.

FIG. 40 shows a cross-sectional side view of the catheter assembly 100 of FIG. 39 rotated 90 degrees along the axis of the needle. The various components are more clearly shown, including the valve 120, the valve opener 122, and the needle guard 130. Although a separately formed securing device or a unitarily formed securing device is not shown, one can be used to secure the valve 120 within the interior cavity 123 of the catheter hub 102 as previously described elsewhere herein.

FIG. 41 is a partial blown-up view of the catheter assembly of FIG. 40 to more clearly show the various components incorporated with the assembly. As shown, the valve 120 can embody the valve 120 shown in FIG. 13 and can be held between a distal shoulder 173 and a proximal shoulder 176a. The valve opener 122 located proximal of the valve 120 can include a nose section 150 having an actuating end for pushing into the valve 120 to open the one or more slits of the valve disc to deflect two or more flaps, such as three slits and three flaps or four slits and four flaps. The valve opener 122 can include at least one plunger element 152 with two spaced apart plunger elements 152 being more preferred, which can have one or more gaps therebetween for fluid flow. A stabilizing element 158 can connect or attach to the two plunger elements 152. In the example shown, two stabilizing elements 158 connect to the two plunger elements 152, at opposite side edges of the plunger elements. The two stabilizing elements 158 and the two plunger elements 152 define an inside opening 400 (FIG. 47) that is smaller compared to the dimension of the needle guard 130 at the two elbows 188a, 190a, as previously described. Thus, when the needle 108 biases the two arms 188, 190 of the needle guard 130 apart, the needle guard is prevented from moving proximally of the two stabilizing elements 158 due to the size difference. As shown, the elbows 188a, 190a are located distally of the two stabilizing elements 158, distal of an internal shoulder 176c inside the catheter hub. Thus, in addition to the two stabilizing elements 158, the needle guard 130 can be held inside the catheter hub by the proximal shoulder 176c in the ready to use position and during retraction of the needle until the needle tip moves proximally of the two distal walls of the two arms and collapses together, as previously discussed.

Figure 42:
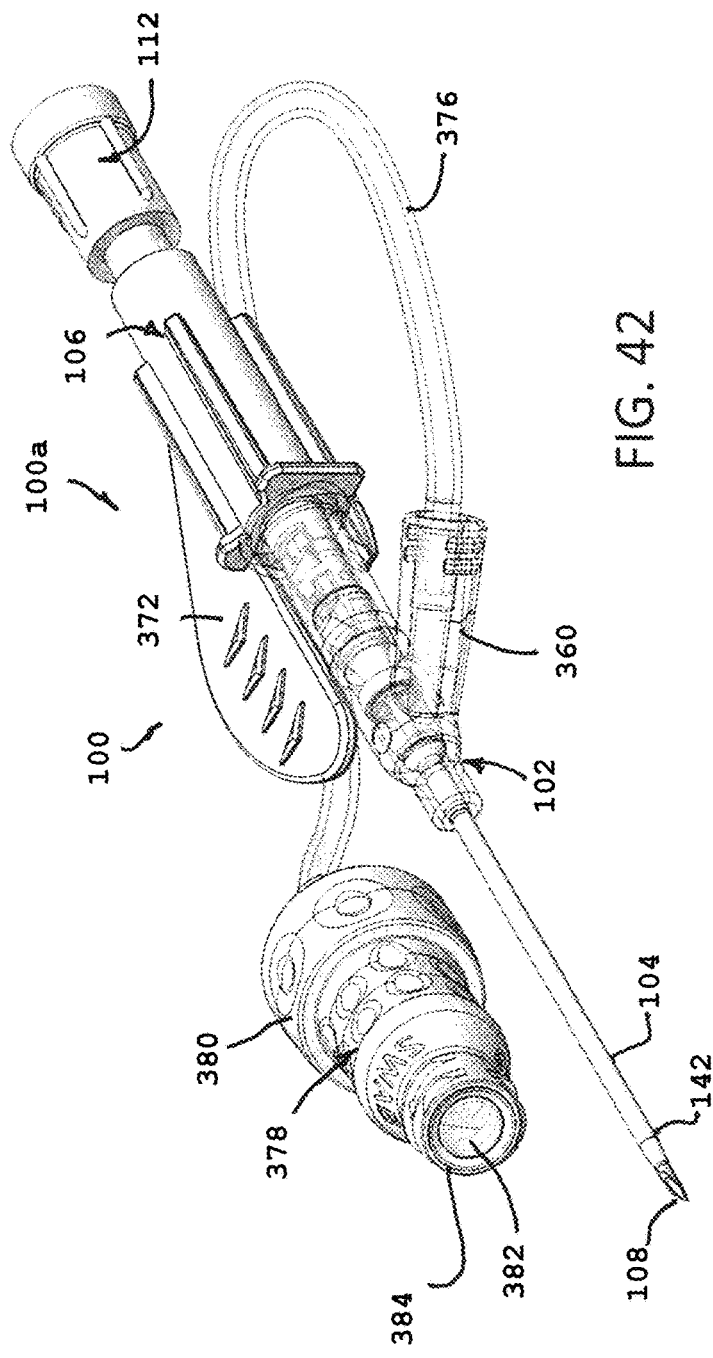
FIG. 42 is a perspective view of an integrated catheter assembly comprising a side port connected to a tubing, which is further connected to a fluid connector.

FIG. 42 is a perspective view of the catheter assembly 100 with a side port 360, also called an integrated catheter assembly 100a, of FIGS. 39-41. As previously discussed, a tubing or tubing length 376 can be attached to the side port 160 at a first end of the tubing and to a fluid connector 378 at a second end of the tubing 376. The fluid connector 378 can embody a number of different devices, such as a plug septum or a needleless valve. As shown, the fluid connector is a needleless valve 378 comprising a housing 380 having a moveable piston 382 located internally thereof. The housing 380 can have an inlet opening 384 having a female Luer for receiving a male Luer tip, such as a syringe tip. The syringe can be used to open the fluid connector 378 without a needle by compressing the piston 382.

When inserted into the inlet opening 384, the male Luer tip of the syringe compresses the piston 382 to open a fluid pathway between the inlet 384 and the outlet of the housing 380. The outlet of the housing 380 is connected to the tubing 376. Thus, fluid, such as medication, supplement or medicament, dispensed from the syringe via the male Luer tip can flow through the needleless valve 378, out the outlet of the housing 380, into the tubing 376 to then flow through the side port 360, then into the distal chamber 368 of the catheter hub 102, and then into the lumen of the catheter tube 104 and into the patient.

In use, the present catheter assembly 100 with the side port 360 can be gripped using the paddle grip 372, if incorporated, and then inserted into the vein with the needle tip and the tip of the catheter tube. Primary blood flash back can be viewed when blood flows through the needle and into the needle hub. With primary flash back confirmed, the practitioner can then pull the needle in the proximal direction to permit blood to flow between the needle and the catheter tube to check for secondary blood flash back. If secondary blood flash back is confirmed, the user can then insert the catheter assembly further into the vein by pushing the catheter tube further into the vein for vascular access. The needle and the needle hub can then be completely removed from the catheter tube and the catheter hub. Upon retracting the needle, the needle tip will move proximally of the two distal walls of the needle guard, which allows the two arms of the needle guard to move together and release from the stabilizing elements. As the change in profile 142 engages the opening on the proximal wall of the needle guard 130, further retraction of the needle will remove the needle guard from the catheter hub, as previously discussed.

Following removal of the needle 108 and the needle hub 106 and with the catheter tube 104 located in the vein of a patient, the assembly of FIGS. 39-42 resembles the device shown in FIGS. 6, 8, 10, 16, 18, 20, 27, 29, 31, and 36. Following removal of the needle 108, the plurality of valve flaps of the valve 120 are recoiled or return to their relaxed state to close the slits and restrict flow in the proximal and distal directions through the valve 120. In an example, the actuating end 180 at the nose section 150 of the valve actuator or opener 122 is proximal of the valve in the valve opener proximal position, spaced from the proximally facing surface of the valve and spaced from the securing device, if incorporated. The tapered surface of the nose section 150 is also spaced from the securing device, if incorporated. This spacing or gap between the nose section and the securing device, if incorporated, allows the valve actuating element 122 to move forward in the distal direction, when pushed by a male Luer tip, before hitting or contacting the securing device. This arrangement provides room for the valve opener to be displaced in the distal direction to open the valve. In an example, distal advancement of the valve opener is stopped when the male Luer tip abuts the female Luer of the catheter hub 102 in a Luer fit, as described elsewhere herein. As shown in FIG. 41, the actuating end 180 of the nose section 150 can be spaced from the proximally facing surface of the valve 120 in the ready to use position with the needle tip extending distally of the distal opening of the catheter tube and in the valve opener proximal position. In other examples, the actuating end 180 can contact the proximally facing surface of the valve 120 prior to being advanced in the distal direction by the male Luer tip. In an example, the valve 120 and the valve opener 122 of FIGS. 31-35 may be used with the catheter hub of the present embodiment.

In an example, an IV drip line of an IV administration set can be connected to the catheter hub 102 via the proximal opening 136 of the catheter hub. With the catheter hub occupied by an IV administration set, the fluid connector 378 connected to the catheter hub via the tubing and the side port can be used to infuse medication to the patient, such as via a syringe. Alternatively, an IV drip line of an IV administration set can be connected to the fluid connector 378 and the proximal opening 136 of the catheter hub 102 can be used to infuse medication, such as via a syringe.

With reference now to FIG. 43, a perspective view of a valve opener or actuator 122 provided in accordance with further aspects of the invention is shown. The present valve opener 122 is similar to other valve openers described herein, such as the valve openers of FIGS. 4, 5, 15, 20, and 33, with a few exceptions. As shown, the valve opener 122 comprises a nose section 150 with an actuating end 180, a transition section 296 that increases in cross-sectional dimension from the nose section 150 to a larger cross-section in the proximal direction. Two plunger elements 152 can extend from the transition section 296, in the proximal direction. The present valve opener 122 may be used with any of the catheter assemblies described herein, such as those with a securing device.

As shown, the transition section 296 is tapered with several slanted segments. In other examples, the transition section 296 can embody a smooth curve or single slanted taper that increases from the nose section 150 in the proximal direction. The nose section 150 distal of the transition section 296 is generally frustoconical in shape and has a through opening for fluid flow. The tapered surface of the nose section 150 allows the valve flaps 194 of the valve to impart a pair of component forces, which include a proximally directed force, to return the valve opener 122 to its proximal position after removal of the male Luer tip.

In the example shown, two stabilizing elements 158 are incorporated with the valve opener 122. Each stabilizing element 158 connects to the two plunger elements 152. Compared to the stabilizing elements 158 of FIG. 33, at least one of the stabilizing elements 158 of the present valve opener 122 has a width defined between a distal edge 158a and a proximal edge 158b that can vary in width along the length of the bridge defining the stabilizing element. For example, the stabilizing element 158 can have a width between a first end and a second end, or the two ends that attach to the two plunger elements, and wherein the width can be narrow near the two ends but wider near the middle of the length. The wider part 388 of the stabilizing element 158 can range from 25% to 75% of the length of the stabilizing element 158. However, like the valve opener of FIG. 33, one or both stabilizing elements 158 can have the same width along the entire length thereof, similar to the bridge defining the stabilizing element of FIG. 33. In an example, the wider part 388 can be centrally positioned between the two ends of the stabilizing element 158. In some examples, a cut-out or a recess 390 can be incorporated on the proximal edge 158b of one or both stabilizing elements 158.

In an example and with reference to FIG. 44, the distal edge 158a of the wider part 388 of the stabilizing element 158 can have a taper edge 392. The taper of the taper edge 392 should originate at or closer to the exterior surface of the stabilizing element 158 and slant towards the inner surface of the stabilizing element 158. In other words, the tip of the taper edge 392 should be closer to the exterior surface of the stabilizing element 158 than the interior surface of the stabilizing element 158. As further discussed below, the configuration with the taper edge 392 can facilitate release of a needle guard. Where two stabilizing elements 158 are incorporated, both distal edges of the two stabilizing elements can incorporate the taper edge 392 shown in FIG. 44.

In some examples, each of the two stabilizing elements 158 of the valve opener 122 can have the same width along the length thereof and both stabilizing elements 158 with the constant width can have a distal edge 158a with a taper 392 as shown in FIG. 44. For example, the distal edges of the two stabilizing elements 158 of FIG. 33 can have the taper edge 392 shown in FIG. 44. In some examples, the valve opener 122 can have two stabilizing elements 158, one with the same width along the length thereof and one with a wider part 388 at a central location along the length thereof. One or the other or both of the stabilizing elements 158 can have a distal edge 158a with a taper 392. In other examples, one or both distal edges of the two different stabilizing elements 158 can have a typical square or straight up and down edge, which can also allow a needle guard to release, as further discussed below.

As shown, the two plunger elements 152 can have sections that extend proximally of the proximal edge 158b of the stabilizing element 158. In some examples, the proximal edge 182 of the two plunger elements 152 and the proximal edge 158b of the stabilizing element 158, or of both stabilizing elements, can terminate generally along a same vertical plane. In the embodiment where the proximal edges terminate generally along the same plane, the distal edge 158a of the stabilizing element can be extended in the distal direction, such as by increasing the width of the stabilizing element 158. Variation in the location of the distal edge 158a can be utilized to control the interactions between the needle guard 130 and the stabilizing element 158.

Figure 45A:
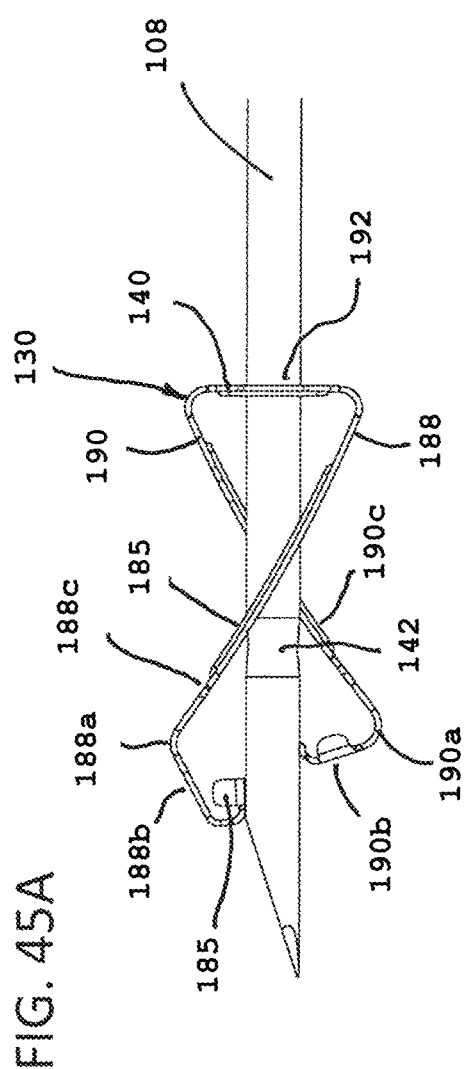
FIGS. 45A and 45B depict a needle guard mounted on a needle, the needle guard having an arm with a single bend or a single change in direction.
Figure 45B:
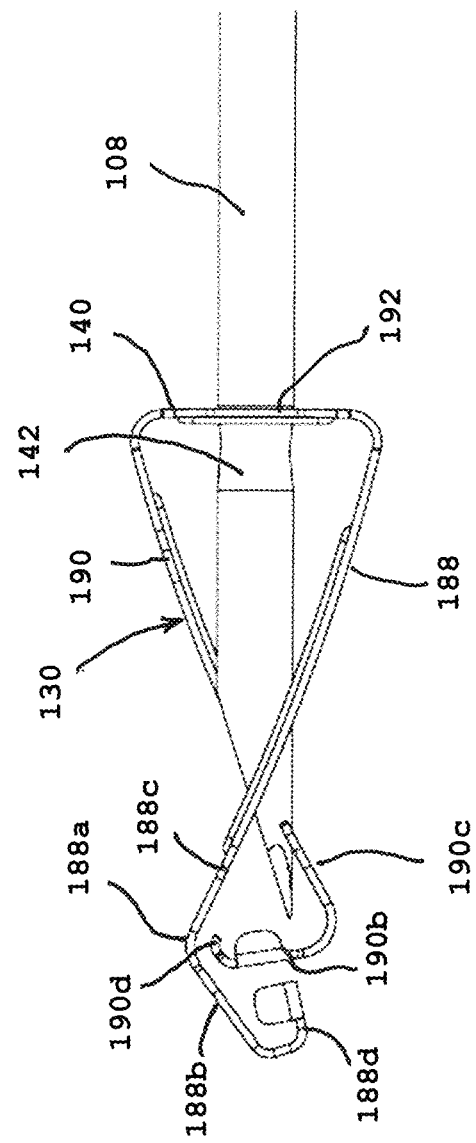

With reference now to FIGS. 45A and 45B, a needle guard 130 provided in accordance with further aspects of the invention are shown mounted onto a needle and activated to guard the needle tip are shown, respectively. The needle guard 130 can be used with various catheter assemblies described herein.

The present needle guard 130 is similar to other needle guards 130 described elsewhere herein and comprises a proximal wall 140 having a perimeter 192 defining an opening for accommodating the needle 108 and to engage a change in profile 142 formed with the needle. Two arms 188, 190 extend distally of the proximal wall 140. Each arm has a distal wall 188b, 190b and an elbow 188a, 190a located between the distal wall and the elongated arm portion 188c, 190c of the arm. Ribs or tabs 185 can be incorporated at various portions of the needle guard 130 to provide added rigidity or stiffness. As shown, tabs or ribs can be provided on the edges of the proximal wall 140, on each of the two elongated arm portions 188c, 190c, and on the distal walls 188b, 190b. In a preferred embodiment, each distal wall 188b, 190b is provided with a curved lip 188d, 190d (FIG. 45B) so that the curved lip abuts the side of the needle when the needle is located between the two arms, as shown in FIG. 45A. The curved lips can be incorporated with the needle guard so that the needle does not abut an edge of the distal wall, which can cause scraping, but instead with the flat exterior surfaces of the curved lips. In some examples, tabs or ribs can be omitted from the distal wall 188b, such as from the curved lip 188d, of the first arm 188.

The two arms 188, 190 intersect one another along the side view shown in both the retracted or needle exposed position of FIG. 45A and in the needle guarded or protective position of FIG. 45B. In other examples, the two arms can extend distally of the proximal wall 140 on respective sides of the needle shaft but not cross the needle axis.

FIG. 45B shows the needle tip retracted in the proximal direction to move proximally of the two distal walls 188b, 190b. When so moved, the needle no longer biases the two arms and the two arms are allowed to move closer together, which in turn allows the dimension measured between the two elbows 188a, 190a to decrease compared to when the two arms are biased by the needle in FIG. 45A. The needle 108 is retracted in the proximal direction until the change in profile 142 abuts the perimeter 192 defining the opening on the proximal wall 140. As previously discussed, the perimeter 192 has a smaller dimension than the largest cross-sectional dimension of the change in profile 142. This allows the needle 108 to move in the proximal direction to remove the needle guard 130 with the needle, as previously discussed.

FIG. 45B shows the two arms 188, 190 of the needle guard 130 having two different lengths. Thus, in the protective position, the two distal walls 188b, 190b overlap when looking down the axis of the needle. In an example, the angle between the distal wall 188b and the elongated arm portion 188c of the first arm 188 is larger than the angle between the distal wall 190b and the elongated arm portion 190c of the second arm 190. From the needle tip exposed position of FIG. 45A to the protective position of FIG. 45B, the needle guard has a surface located to a side of the needle in the ready to use position and transitional to a position distal of the needle tip in a protective position to cover the needle tip from inadvertent needlestick.

In an example, each elongated arm portion 188c, 190c of the two arms 188, 190 is generally straight or linear, with possibly some slight bending or flexing when biased by the needle, up to the respective elbow 188a, 190a. Then a single radius bend is made to form the respective elbow 188a, 190a and the respective distal wall 188b, 190b. Another single radius bend is made to form the respective curved lip 188d, 190d. At the elbow, the single radius bend can have a simple curve or a complex curve. However, unlike the needle guard 130 of FIGS. 4 and 5, which has at least two bends and two changes in direction between the elongated arm portion of the arm and the distal wall of each arm, the present needle guard 130 has a single bend and a single change in direction between the elongated arm portion 188c, 190c and the distal wall 188b, 190b of each arm.

The single bend and the single change in direction produces a smooth or flat profile between the elongated arm portion and the elbow. The flat profile on the arm should be located so that interference with an edge of a stabilizing element, such as getting hung up or stuck, is minimized, as further discussed below. Thus, there can be additional bends or changes in direction on each arm downstream of the first bend forming the elbow providing the transition between the elongated arm portion 188c, 190c and the first bend for forming the elbow 188a, 190a is generally flat or smooth as shown in order to eliminate potential snag points that can cause sticking or binding for a typical range of angle that the needle is oriented during removal, as further discussed below. In general, use the needle is pulled straight out of the catheter hub along the same axis. In extreme cases the needle can be pulled out at an angle, until the needle contacts the upper proximal opening of the catheter hub. If the needle is pulled out at an angle higher than just touching the proximal opening of the catheter hub then this is abusive use, which could result in the bending of the needle.

Figure 46B:
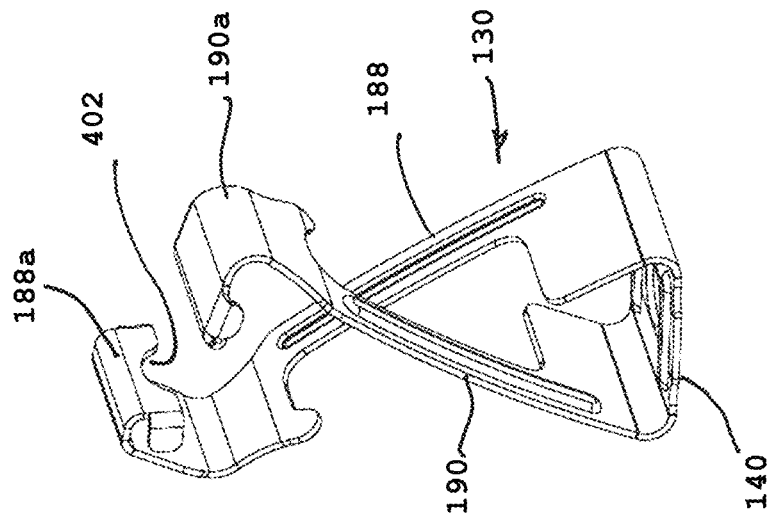
FIGS. 46A and 46B depict different perspective views of a needle guard in the open state as if a needle (not shown for clarity purposes) was opening the arms to show features of the needle guard.
Figure 46A:
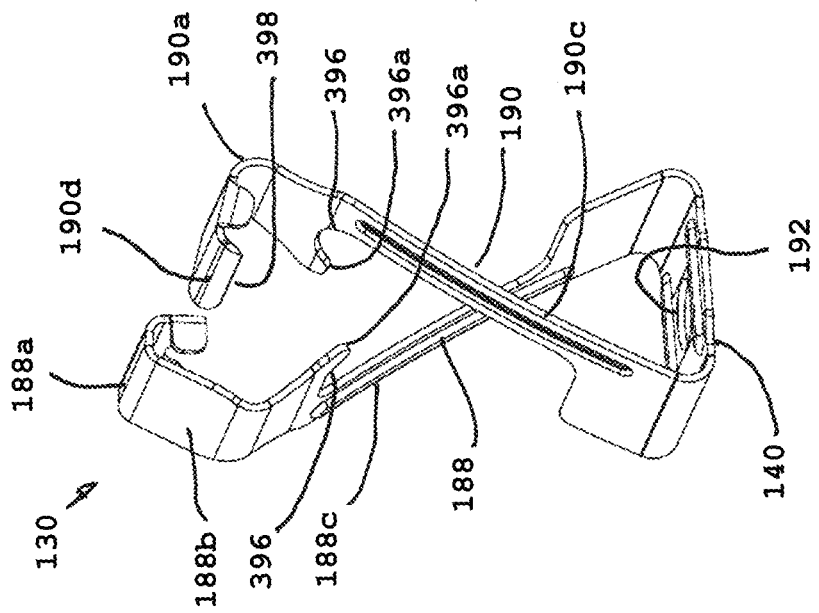

With reference now to FIGS. 46A and 46B, two different perspective views of a needle guard 130 are shown. The needle guard of the present embodiment is similar to the needle guard shown with respect to FIGS. 45A and 45B and can be used with various catheter assemblies described herein. The two arms 188, 190 are shown biased apart without the needle that normally biases the arms apart to show features of the distal walls and the curved lips, as further discussed below. The arms 188, 190 of the needle guard are shown with a smooth or flat profile between the elongated arm portion 188c, 190c and the elbow 188a, 190a, with only a single bend or change in direction. As shown, each elongated arm section 188c, 190c of the first arm 188 and the second arm 190 has sections with different arm widths. Each arm 188, 190 also includes a cut-out 396 having a lip 396a that resembles a hook. The cut-out or cut-outs 396 on the two arms allow the two arms 188, 190 to straddle the needle to provide lateral stability as the needle transitions from the ready to use position, with the needle tip exposed, to the protective position, with the needle tip guarded.

FIG. 46A shows the curved lip 190d on the second arm 190 with a straight edge 398. However, the curved lip 190d is configured to abut the needle at the flat surface adjacent the edge when in the ready to use position, as shown in FIG. 45A. FIG. 46B shows the curved lip 188a on the first arm with a cut-out 402 resembling an arc. The cut-out 402 can be utilized to change the location where the surface of the curved lip, not the edge, contacts the needle, as shown in FIG. 45A. In some examples, the cut-out 402 can be omitted.

The needle guard 130 of FIGS. 46A and 46B, as well as other needle guards described herein, can each be made from a stamped metal sheet, such as a stamped stainless-steel sheet, and using a stamping and bending method to form the needle guard in the shape shown.

Figure 47:
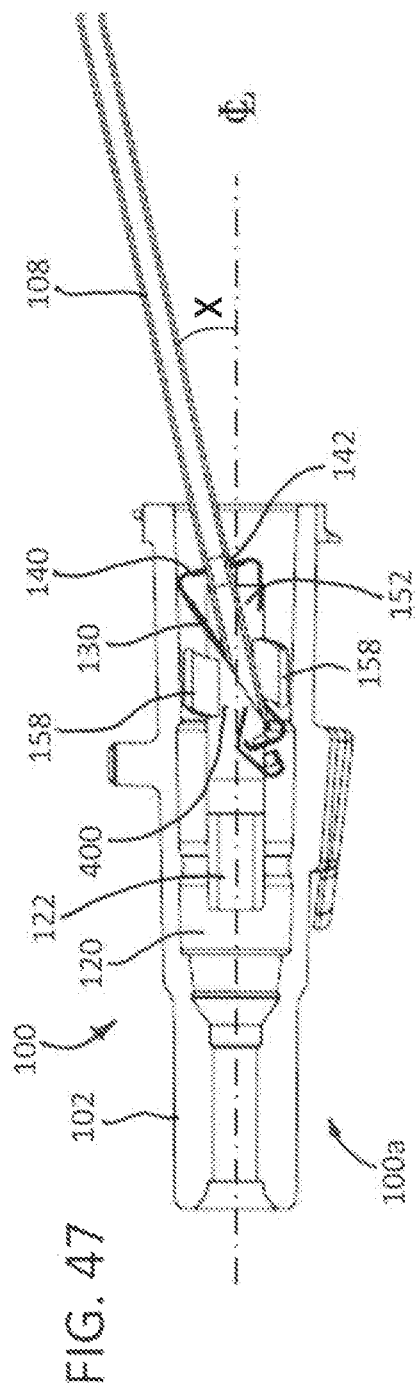
FIG. 47 depicts a state of withdraw of a needle from a catheter hub. A catheter tube is not shown protruding from the distal end of the catheter hub for simplicity.

With reference now to FIG. 47 in combination with FIGS. 43 and 44, a schematic view showing the needle 108 retracted proximally at an angle above the center line following successful venipuncture is shown. For example, the catheter assembly 100 of FIG. 47 can resemble the catheter assemblies of FIGS. 5 and 39-42 and is shown following successful venipuncture, when the needle is retracted at an angle above the center line in the proximal direction to remove from the catheter hub 102. Also shown in FIG. 47 is a valve 120, a valve opener 122, and a needle guard 130 activated to cover the tip of the needle 108. The valve and the valve opener can be similar to those discussed elsewhere herein. A separately formed securing device or a unitarily formed device may be incorporated to secure the valve within the catheter hub. The needle guard 130 can be the same needle guard shown and discussed with reference to FIGS. 45A-46B. FIG. 47 is shown without a catheter tube, but one is understood to be usable with the catheter hub 102 via a metal bushing.

When the needle tip retracts proximally of the two distal walls 188b, 190b (FIGS. 45A-46B) of the needle guard 130, the bias by the needle on the two arms 188, 190 is removed, thus allowing the two arms to move closer together or to touch each other. This in turn reduces the dimension measured at the two elbows 188a, 190a, which decreases thus allowing the needle guard 130 to move proximally through the opening 400 defined by the two stabilizing elements 158 and the two plunger elements 152. However, during retraction of the needle 108 and the needle guard 130 through the opening 400, the practitioner may inadvertently tilt the needle 108 during the proximal retraction. When this occurs, the needle guard 130 may contact the distal edge 158a of one or both stabilizing elements 158 during retraction to thereby catch and possibly get hung up by the contact between the needle guard and the stabilizing element. This would in turn hinder removal of the needle guard 130 through the opening 400.

When an arm of the needle guard 130 has more than one bend or changes in direction at the transition between an elongated arm portion 188c, 190c and an elbow 188a, 190a, such as the needle guard of FIG. 5, the multiple changes in direction can catch the distal edge 158a of a stabilizing element 158 during retraction of the needle guard through the opening 400 during removal of the needle. This in turn requires the user to reposition the angle of the needle 108 relative to the lengthwise axis of the catheter hub 102 to a value that is less than a maximum angle A, during the retraction of the needle in order to avoid having the needle guard catch and hinder the retraction. In contrast, when the needle guard of FIGS. 45A-46B is used with a valve opener 122 having one or two stabilizing elements 158, the single bend or change in direction between the elongated arm portion and the elbow produces a smooth or flat profile that does not readily catch against the distal edge 158a of one or both stabilizing elements 158 during retraction of the needle. Thus, retraction through the opening 400 is facilitated by utilizing a needle guard having an arm with a single bend or change in direction to produce a smooth or flat profile that does not readily catch against the distal edge 158a. Thus, a user can position the angle of the needle 108 relative to the lengthwise axis of the catheter hub 102 to a maximum angle B during the retraction in order to avoid catching and hindering the retraction. For two similarly sized catheter assemblies with similarly sized components but with different needle guards, one with one bend or change in direction and another with two or more bends or changes in direction, the angle B is larger than the angle A.

With reference to FIG. 44 in addition to FIG. 47, when the stabilizing element 158 that the needle guard 130 abuts or contacts during retraction in the proximal direction incorporates a tapered edge 392, the likelihood that the transition between the elbow with the elongated arm portion of a needle guard catches the tapered distal edge 392 is reduced. Thus, even if the needle guard has two or more bends at the elbow and the catheter assembly has a stabilizing element with a tapered edge 392, the user holding the same sized catheter assembly can hold the needle at a higher angle A', which is higher than angle A. Similarly, if the needle guard has only one bend or one change in direction to produce a smooth or flat profile that does not readily catch against the distal edge 158a, the user holding the same sized catheter assembly can hold the needle at a higher angle B', which is higher than angle A. Generally speaking, angle B' involving a needle guard with a single bend or change in direction and a valve opener with a stabilizing element with a tapered edge, is larger than angle A', involving a needle guard with two or more bends or changes in direction and a valve opener with a stabilizing element with a tapered edge. For discussion purposes, angle X can represent any one of angle A, A', B, or B', which is understood to depend on whether the needle guard has one or more bends or change in directions and whether the stabilizing element of the valve opener has a tapered edge.

Figure 48:
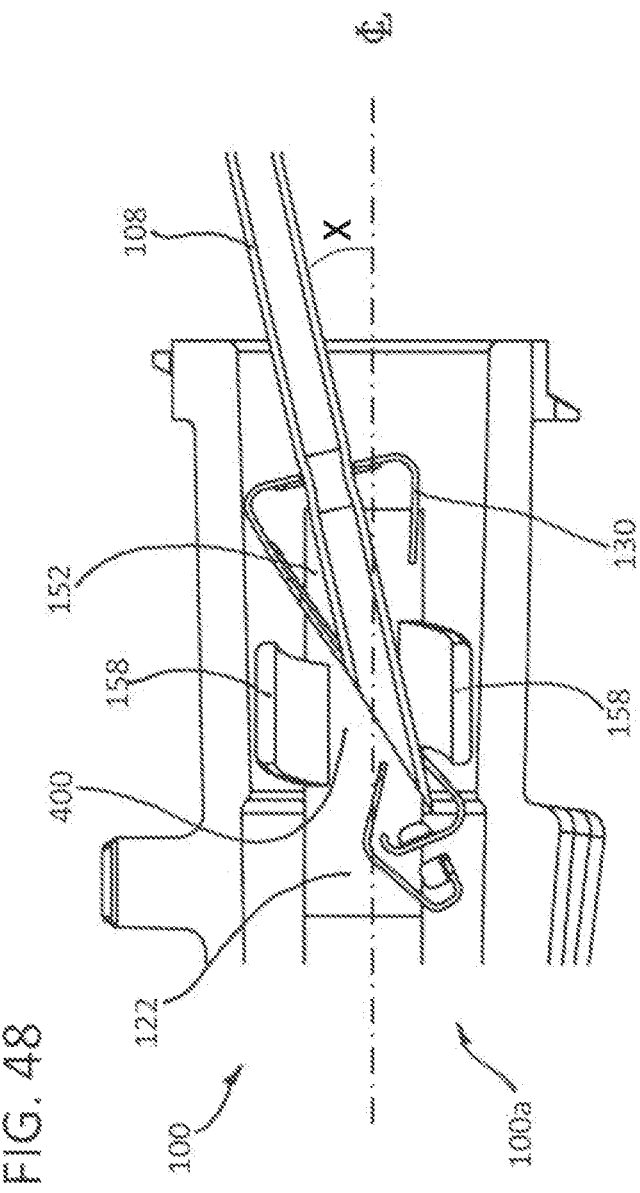
FIG. 48 is an enlarged view of a portion of FIG. 47.

FIG. 48 is an enlarged view of the assembly of FIG. 47.

Aspects of the invention are further understood to include a catheter assembly comprising a catheter tube having a lumen, a distal end opening, and a proximal end attached to a catheter hub, said catheter hub comprising a catheter body with an exterior surface and an interior surface defining an interior cavity having at least one shoulder; a needle having a needle tip at a distal end and having a proximal end attached to a needle hub; said needle projecting through the catheter hub and through the catheter tube and having the needle tip projecting distally of the distal end opening in a ready to use position; a valve having a valve body comprising at least one slit, a proximally facing surface, and a distally facing surface located in the interior cavity of the catheter hub; a valve actuator disposed in the interior cavity of the catheter hub, said valve actuator having a nose section with a bore and a proximal section with at least one gap for fluid flow therethrough or thereacross and being slideable between a proximal position and a distal position inside the interior cavity when pushed by a male Luer; a needle guard having a protective surface located to a side of the needle in a ready to use position and transitionable to a position distal of the needle tip in a protective position to cover the needle tip from an inadvertent needle stick; wherein said needle guard has an arm with an elbow between an elongated arm portion and a distal wall and wherein the elbow has a single change in direction at a location that can contact a stabilizing element on the valve actuator during retraction of the needle guard without catching, hindering, and/or stopping the needle movement.

A securing device can be in contact with or integral to the valve at the proximally facing surface of the valve body for retaining the valve inside the interior cavity of the catheter hub, said securing device can comprise a retainer body having an interior surface defining a bore comprising a fluid path, a distal end, and a proximal end.

The catheter hub can have a side port attached to a tubing at a first end of the tubing. A fluid connector can connect to a second end of the tubing. The fluid connector can comprise a needleless connector. The catheter assembly can be referred to as an integrated catheter assembly.

The stabilizing element of the valve opener or actuator can have a distal edge. The distal edge can have a tapered edge. The taper of the taper edge should originate at or closer to the exterior surface of the stabilizing element and slant towards the inner surface of the stabilizing element. In other words, the tip of the taper edge should be closer to the exterior surface of the stabilizing element than the interior surface of the stabilizing element.

The needle guard can have an arm with a single change in direction between an elongated arm portion and a distal wall of the arm to produce a smooth or flat profile at the elbow, between the elongated arm portion and the distal wall, that does not readily catch against the distal edge of the stabilizing element of the valve actuator.

Methods of making and of using catheter assemblies and components thereof are within the scope of the present invention.

When modifiers such as first, second, third, left, right, etc. are used to distinguish similar components or structures, they are understood as reference nomenclatures to track the similar components only but do not structurally distinguish between or among them unless the context indicates otherwise.

Although limited embodiments of the catheter assemblies and their components have been specifically described and illustrated herein, many modifications and variations will be apparent to those skilled in the art. For example, ported or integrated extension line intravenous catheters would benefit from the invention. Accordingly, it is to be understood that the catheter assemblies and their components constructed according to principles of the disclosed device, system, and method may be embodied other than as specifically described herein. The disclosure is also defined in the following claims.

What is claimed is:

1. A catheter assembly comprising:
    a catheter tube having a lumen, a distal end opening, and a proximal end attached to a distal end of a catheter hub, said catheter hub comprising a catheter body with an exterior surface and an interior surface defining an interior cavity having at least one shoulder;
    a needle having a needle tip at a distal end and having a proximal end attached to a needle hub; said needle projecting through the catheter hub and through the catheter tube and having the needle tip projecting distally of the distal end opening in a ready to use position;
    a valve having a valve disc located in the interior cavity of the catheter hub, the valve disc comprising at least one slit and at least two flaps, a proximally facing surface, and a distally facing surface, wherein said distally facing surface is in contact with the at least one shoulder;
    (i) a skirt section extending from the valve disc, the skirt section comprising a wall with an exterior surface and an interior surface defining a skirt interior and a skirt proximal end surface, said skirt section being in contact with the interior surface of the catheter hub; or (ii) a securing device located proximally of the valve disc, the securing device comprising a metallic ring body comprising a fluid path, a distal end, a proximal end, and at least one leaf spring having a free end extending proximally inward of the proximal end of the metallic ring body, the securing device securing the valve from proximal displacement;
    a valve actuator located in the interior cavity of the catheter hub, said valve actuator having a nose section at a distal end of the valve actuator and a proximal section proximally of the nose section; the nose section comprising a bore for fluid flow and an actuation end at a distal most end of the nose section, the proximal section comprising at least one gap for fluid flow therethrough or thereacross, a first plunger element, and a second plunger element, the valve actuator being located in a proximal position within the interior cavity and slidable to a distal position within the interior cavity when pushed by a medical implement, wherein:
(a) when the skirt section is present, the nose section is located at least in part inside the skirt interior when the needle is in the ready to use position; or
(b) when the securing device is present, the nose section is located inward of the metallic ring body when the needle is in the ready to use position; and
wherein when the skirt section is present, two spaced apart abutting surfaces are aligned with and located distally of the first plunger element and the second plunger element, each of the two spaced apart abutting surfaces are located proximally of the actuation end of the valve actuator and proximally of the skirt proximal end surface when the needle is in the ready to use position, the two spaced apart abutting surfaces are sized and shaped to compress the skirt proximal end surface when said valve actuator is in the distal position to create stored energy in the valve skirt to then exert a proximally directed force against the two spaced apart abutting surfaces or, when the securing device is present, the at least one leaf spring is spaced from the nose section and biasing against the nose section when the valve actuator is in the distal position.

2. The catheter assembly of claim 1, further comprising a needle guard having a protective surface located to a side of the needle when the needle is in the ready to use position and transitional to a position distal of the needle tip in a protective position to cover the needle tip from inadvertent needlestick.

3. The catheter assembly of claim 2, wherein at least one stabilizing element comprising a first end connected to the first plunger element and a second end connected to the second plunger element, said at least one stabilizing element further comprising a distal edge and a proximal edge.

4. The catheter assembly of claim 3, wherein the needle guard comprises a proximal wall comprising a perimeter defining an opening and at least one arm extending distally of the proximal wall, said at least one arm comprising an elongated arm portion, a distal wall, and an elbow located between the elongated arm portion and the distal wall, and wherein a single bend is located between the elongated arm portion and the distal wall to define a smooth or flat profile at the elbow where the needle guard contacts the distal edge of the at least one stabilizing element.

5. The catheter assembly of claim 4, wherein the catheter hub comprises a side port having an elongated body with a bore, said elongated body extending at an angle to the catheter body.

6. The catheter assembly of claim 3, wherein the distal edge of the at least one stabilizing element comprises a taper edge that originates closer to an exterior surface of the at least one stabilizing element and slants toward an inner surface of the at least one stabilizing element.

7. The catheter assembly of claim 1, wherein the skirt section comprises a ramp-shape cross-section and wherein said skirt proximal end surface is located at a proximal end of said ramp-shape cross-section.

8. The catheter assembly of claim 1, wherein the nose section of the valve actuator has a first slope extending into a transition section and wherein the transition section has a second slope and wherein the second slope and the first slope have different slope values.

9. The catheter assembly of claim 1, wherein the valve disc has a first portion with a first thickness and a second portion with a second thickness and wherein the first thickness is greater than the second thickness.

10. The catheter assembly of claim 9, wherein the at least one slit is formed through the second portion of the valve disc.

11. The catheter assembly of claim 1, further comprising a grip paddle having a body extending laterally of an axis defined by the needle.

12. The catheter assembly of claim 1, wherein each of the two spaced apart abutting surfaces are located at a distal end of a shoulder of the at least one shoulder.

13. The catheter assembly of claim 12, further comprising a slanted surface extending proximally of each abutting surface of the two spaced apart abutting surfaces.

14. The catheter assembly of claim 12, wherein each of the two spaced apart abutting surfaces has an edge to define two edges and the two edges are parallel to one another.

15. The catheter assembly of claim 1, wherein each of the two spaced apart abutting surfaces are angled to a surface of the nose section to define a radially outward projection.

16. The catheter assembly of claim 15, wherein the two spaced apart abutting surfaces are generally parallel to one another.

17. A method of manufacturing a catheter assembly comprising:
attaching a catheter tube having a lumen, a distal end opening, and a proximal end to a distal end of a catheter hub, said catheter hub comprising a catheter body with an exterior surface and an interior surface defining an interior cavity having at least one shoulder;
attaching a needle to a needle hub; said needle having a needle tip at a distal end and having a proximal end, said needle projecting through the catheter hub and through the catheter tube and having the needle tip projecting distally of the distal end opening in a ready to use position;
placing a valve having a valve disc in the interior cavity of the catheter hub, the valve disc comprising at least one slit and at least two flaps, a proximally facing surface, and a distally facing surface, wherein said distally facing surface contacting the at least one shoulder;
(i) extending a skirt section from the valve disc, the skirt section comprising a wall with an exterior surface and an interior surface defining a skirt interior and a skirt proximal end surface, said skirt section being in contact with the interior surface of the catheter hub; or
(ii) placing a securing device in the interior cavity of the catheter hub and proximally of the valve disc, the securing device comprising a metallic ring body comprising a fluid path, a distal end, a proximal end, and at least one leaf spring having a free end extending proximally inward of the proximal end of the metallic ring body, the securing device securing the valve from proximal displacement;
placing a valve actuator in the interior cavity of the catheter hub, said valve actuator having a nose section at a distal end of the valve actuator and a proximal section proximally of the nose section; the nose section comprising a bore for fluid flow and an actuation end at a distal most end of the nose section, the proximal section comprising at least one gap for fluid flow therethrough or thereacross, a first plunger element, and a second plunger element, the valve actuator having a proximal position within the interior cavity and slidable to a distal position within the interior cavity when pushed by a medical implement, wherein:

(a) when the skirt section is present, the nose section is located at least in part inside the skirt interior when the needle is in the ready to use position; or (b) when the securing device is present, the nose section is located inward of the metallic ring body when the needle is in the ready to use position; and wherein when the skirt section is present, two spaced apart abutting surfaces are aligned with and located distally of the first plunger element and the second plunger element, the two spaced apart abutting surfaces are located proximally of the actuation end of the valve actuator and proximally of the skirt proximal end surface when the needle is in the ready to use position, the two spaced apart abutting surfaces are sized and shaped to compress the skirt proximal end surface when said valve actuator is in the distal position to create stored energy in the valve skirt to then exert a proximally directed force against the two spaced apart abutting surfaces or, when the securing device is present, the at least one leaf spring is spaced from the nose section and biasing against the nose section when the valve actuator is in the distal position.

18. The method of claim 17, further comprising placing a needle guard in the interior cavity of the catheter hub, the needle guard having a protective surface located to a side of the needle when the needle is in the ready to use position and transitional to a position distal of the needle tip in a protective position to cover the needle tip from inadvertent needlestick.

19. The method of claim 18, further comprising extending a side port having an elongated body with a bore at an angle to the catheter body.

20. The method of claim 18, wherein the needle guard comprises a proximal wall comprising a perimeter defining an opening and at least one arm extending distally of the proximal wall, said at least one arm comprising an elongated arm portion, a distal wall, and an elbow located between the elongated arm portion and the distal wall, and wherein a single bend is located between the elongated arm portion and the distal wall to define a smooth or flat profile at the elbow where the needle guard contacts a distal edge of at least one stabilizing element.

21. The method of claim 17, further comprising pushing the skirt proximal end surface in a distal direction with the two spaced apart abutting surfaces.

22. The method of claim 21, wherein each of the two spaced apart abutting surfaces are angled to a surface of the nose section to define a radially outward projection.

23. The method of claim 22, wherein the two spaced apart abutting surfaces are generally parallel to one another.

24. A catheter assembly comprising:
a needle attached to a needle hub;
a catheter tube attached to a catheter hub;
a valve and a valve actuator located inside an interior of the catheter hub, said valve comprising a valve disc having a plurality of valve flaps, a proximally facing surface, and a distally facing surface; and
a securement device comprising a body and separately formed from the catheter hub, the securement device is in contact with the interior of the catheter hub and the body is in contact with a proximal-most surface of the valve to retain the valve inside the interior of the catheter hub;

wherein the valve actuator is movable into contact with the securement device and the valve when pushed by a medical implement to deflect the plurality of valve flaps in a valve opened position and movable away from the valve and away from the securement device to enable the plurality of valve flaps to return to a valve closed position;

wherein the needle projects through the valve, the valve actuator, the catheter hub, and the catheter tube in a ready to use position; and wherein the securement device comprises one of a leaf spring, a canted coil spring comprising a plurality of coils, or an O-ring.

25. The catheter assembly of claim 24, wherein the securement device has a ring body with an annular space and the leaf spring extends from the ring body.

26. The catheter assembly of claim 24, further comprising a needle guard having a protective surface located to a side of the needle when the needle is in the ready to use position and transitional to a position distal of a needle tip in a protective position to cover the needle tip from inadvertent needlestick.

27. The catheter assembly of claim 26, wherein the needle guard comprises a proximal wall comprising a perimeter defining an opening and at least one arm extending distally of the proximal wall, said at least one arm comprising an elongated arm portion, a distal wall, and an elbow located between the elongated arm portion and the distal wall, and wherein a single bend is located between the elongated arm portion and the distal wall to define a smooth or flat profile at the elbow where the needle guard contacts a distal edge of at least one stabilizing element.

28. The catheter assembly of claim 24, wherein the valve comprises a skirt section and a skirt proximal end surface, the skirt section comprising a ramp-shape cross-section and wherein the skirt proximal end surface is located at a proximal end of said ramp-shape cross-section.

29. The catheter assembly of claim 24, wherein the valve actuator comprises a nose section having a first slope extending into a transition section and wherein the transition section has a second slope and wherein the second slope and the first slope have different slope values.

30. The catheter assembly of claim 24, wherein the valve disc has a first portion with a first thickness and a second portion with a second thickness and wherein the first thickness is greater than the second thickness.

31. The catheter assembly of claim 30, wherein at least one slit is formed through the second portion of the valve disc.

32. The catheter assembly of claim 24, wherein at least one stabilizing element comprising a first end connected to a first plunger element of the valve actuator and a second end connected to a second plunger element, said at least one stabilizing element further comprising a distal edge and a proximal edge.

33. The catheter assembly of claim 32, wherein the distal edge of the at least one stabilizing element comprises a taper edge that originates closer to an exterior surface of the at least one stabilizing element and slants toward an inner surface of the at least one stabilizing element.

34. The catheter assembly of claim 24, wherein the catheter hub comprises a side port having an elongated body with a bore, said elongated body extending at an angle to a catheter body of the catheter hub.

35. The catheter assembly of claim 24, further comprising a grip paddle having a body extending laterally of an axis defined by the needle.

36. A catheter assembly comprising:
a needle attached to a needle hub;
a catheter tube attached to a catheter hub;
a valve and a valve actuator located inside an interior of the catheter hub, said valve comprising a valve disc having a plurality of valve flaps, a proximally facing surface, and a distally facing surface; and
a securement device comprising a body and separately formed from the catheter hub, the securement device is in contact with the interior of the catheter hub and the body is in contact with a proximal-most surface of the valve to retain the valve inside the interior of the catheter hub;
wherein the valve actuator is movable into contact with the securement device and the valve when pushed by a medical implement to deflect the plurality of valve flaps in a valve opened position and movable away from the valve and away from the securement device to enable the plurality of valve flaps to return to a valve closed position;
wherein the needle projects through the valve, the valve actuator, the catheter hub, and the catheter tube in a ready to use position; and
wherein the valve actuator has a nose section and wherein the nose section is located in a skirt interior of a valve skirt when the needle is in the ready to use position and a plurality of abutting edges on the valve actuator are located proximally of the valve skirt for compressing the valve skirt.

37. The catheter assembly of claim 36, wherein the securement device comprises one of a leaf spring, a canted coil spring comprising a plurality of coils, or an O-ring.

38. The catheter assembly of claim 36, wherein the valve skirt of the valve comprises a ramp-shape cross-section and wherein a skirt proximal end surface is located at a proximal end of said ramp-shape cross-section.

39. The catheter assembly of claim 36, further comprising a needle guard having a protective surface located to a side of the needle when the needle is in the ready to use position and transitional to a position distal of a needle tip in a protective position to cover the needle tip from inadvertent needlestick.

40. The catheter assembly of claim 39, wherein the needle guard comprises a proximal wall comprising a perimeter defining an opening and at least one arm extending distally of the proximal wall, said at least one arm comprising an elongated arm portion, a distal wall, and an elbow located between the elongated arm portion and the distal wall, and wherein a single bend is located between the elongated arm portion and the distal wall to define a smooth or flat profile at the elbow where the needle guard contacts a distal edge of at least one stabilizing element.

41. The catheter assembly of claim 36, wherein the nose section has a first slope extending into a transition section and wherein the transition section has a second slope and wherein the second slope and the first slope have different slope values.

42. The catheter assembly of claim 36, wherein the valve disc has a first portion with a first thickness and a second portion with a second thickness and wherein the first thickness is greater than the second thickness.

43. The catheter assembly of claim 42, wherein at least one slit is formed through the second portion of the valve disc.

44. The catheter assembly of claim 36, wherein at least one stabilizing element comprising a first end connected to a first plunger element of the valve actuator and a second end connected to a second plunger element, said at least one stabilizing element further comprising a distal edge and a proximal edge.

45. The catheter assembly of claim 44, wherein the distal edge of the at least one stabilizing element comprises a taper edge that originates closer to an exterior surface of the at least one stabilizing element and slants toward an inner surface of the at least one stabilizing element.

46. The catheter assembly of claim 36, wherein the catheter hub comprises a side port having an elongated body with a bore, said elongated body extending at an angle to a catheter body of the catheter hub.

47. The catheter assembly of claim 36, further comprising a grip paddle having a body extending laterally of an axis defined by the needle.

* * * * *